(12) United States Patent
Johnston et al.

(10) Patent No.: US 11,142,794 B2
(45) Date of Patent: Oct. 12, 2021

(54) MOLECULAR SIGNATURES FOR USE IN DIAGNOSIS AND RESPONSE TO TREATMENT ANALYSIS OF AUTOIMMUNE DISEASES

(71) Applicants: UCB BIOPHARMA SRL, Brussels (BE); BIOGEN MA INC., Cambridge, MA (US)

(72) Inventors: Geoffrey Johnston, Slough (GB); Carrie G. Wager, Watertown, MA (US); Huo Li, Allston, MA (US); Ann Ranger, Northborough, MA (US)

(73) Assignees: UCB BIOPHARMA SRL, Brussels (BE); BIOGEN MA INC., Cambridge, MA (US)

( * ) Notice: Subject to any disclaimer, the term of this patent is extended or adjusted under 35 U.S.C. 154(b) by 74 days.

(21) Appl. No.: 15/763,890

(22) PCT Filed: Oct. 4, 2016

(86) PCT No.: PCT/EP2016/073677
§ 371 (c)(1),
(2) Date: Mar. 28, 2018

(87) PCT Pub. No.: WO2017/060242
PCT Pub. Date: Apr. 13, 2017

(65) Prior Publication Data
US 2018/0265925 A1  Sep. 20, 2018

Related U.S. Application Data

(60) Provisional application No. 62/237,148, filed on Oct. 5, 2015.

(51) Int. Cl.
C12Q 1/68 (2018.01)
C12Q 1/6883 (2018.01)

(52) U.S. Cl.
CPC ..... *C12Q 1/6883* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2012/0088678 A1   4/2012   Albani

FOREIGN PATENT DOCUMENTS

| WO | WO 2006/125117 | 11/2006 |
|----|----------------|---------|
| WO | WO 2006/125143 | 11/2006 |
| WO | WO 2009/062125 | 5/2009 |
| WO | WO 2011/154139 | 12/2011 |
| WO | WO 2014/113804 | 7/2014 |

OTHER PUBLICATIONS

Written Opinion in International Application No. PCT/EP2016/073677, dated Feb. 3, 2017, pp. 1-7.

*Primary Examiner* — Jehanne S Sitton
(74) *Attorney, Agent, or Firm* — Saliwanchik, Lloyd & Eisenschenk

(57) ABSTRACT

The present invention relates to molecular signatures that can be used to identify patients diagnosed with an autoimmune disease, in particular with systemic lupus erythematosus for treatment with a CD40 or CD40L antagonist such as anti-CD40 antibody, anti-CD40L antibody or a binding fragment thereof. The signatures can also be used to monitor target engagement and response to treatment.

Figure 2:
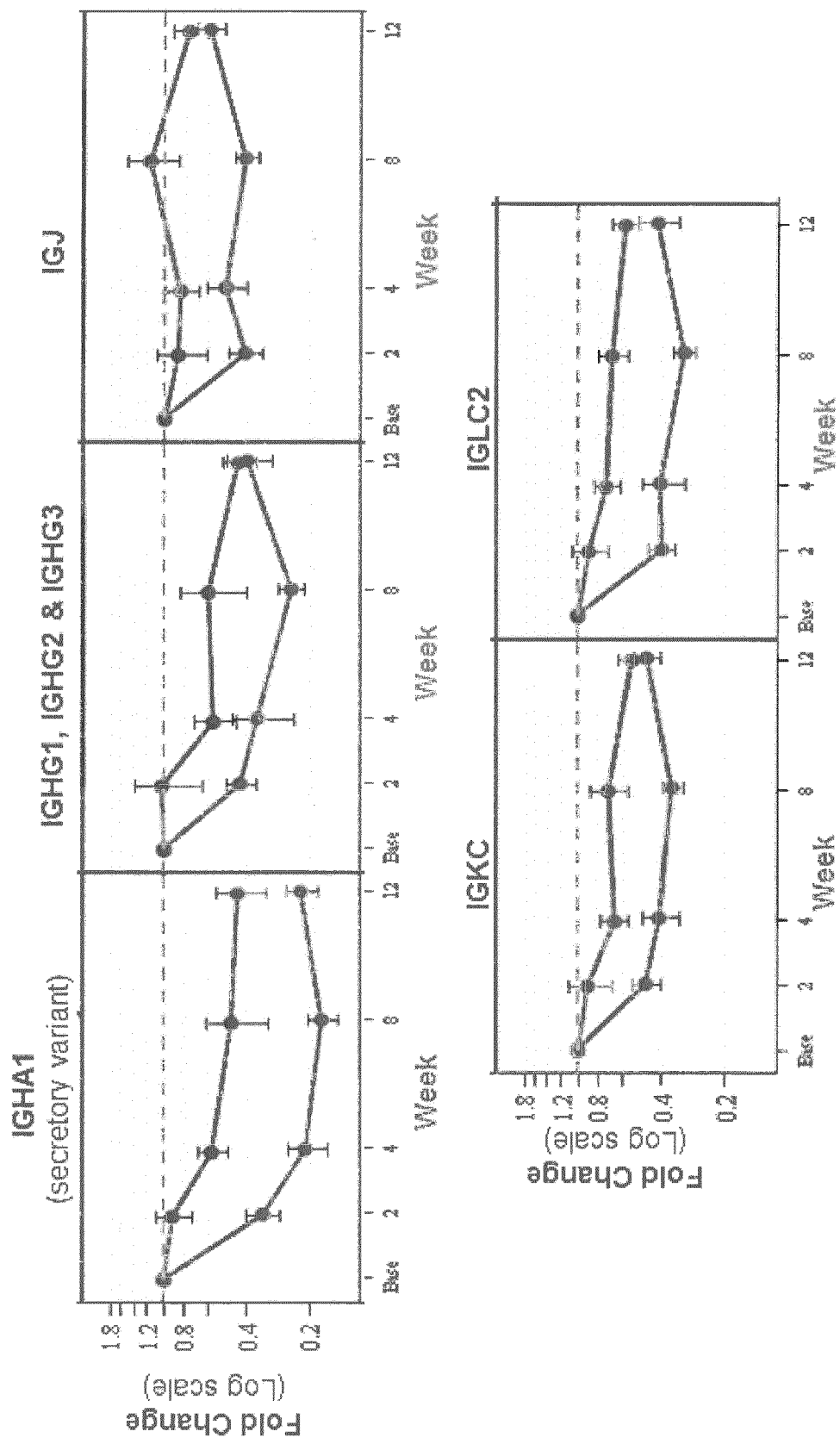

18 Claims, 12 Drawing Sheets
Specification includes a Sequence Listing.

Figure 1

| Functional Group | Gene | Week 2 pvalue | Week 4 pvalue | Week 8 pvalue | Week 12 pvalue |
|---|---|---|---|---|---|
| B Cells | AICDA | 0.9568 | 0.5156 | 0.1797 | 0.3282 |
| B Cells | CD19 | 0.0146 | 0.1395 | 0.0056 | 0.148 |
| B Cells | IGHA1 (Membrane) | 0.3393 | 0.8871 | 0.8272 | 0.0674 |
| B Cells | IGHD | 0.0413 | 0.3274 | 0.1037 | 0.4864 |
| B Cells | IGHG1 | 0.1758 | 0.6556 | 0.2063 | 0.3781 |
| B Cells | IGHM (Membrane) | 0.0076 | 0.2267 | 0.0469 | 0.2246 |
| B Cells | MS4A1/CD20 | 0.0303 | 0.162 | 0.0887 | 0.0209 |
| B Cells | RAG1 | 0.1248 | 0.5456 | 0.8476 | 0.7045 |
| B Cells | SERPINA9 | 0.3146 | 0.8524 | 0.9254 | 0.4682 |
| B Cells | SP140 | 0.3251 | 0.4161 | 0.6792 | 0.7735 |
| B Cells | TCL1A | 0.0077 | 0.0765 | 0.0207 | 0.0762 |
| Plasma Cells | CD38 | 0.9054 | 0.4046 | 0.3925 | 0.9097 |
| Plasma Cells | IGHA1, IGHA2 (Secretory) | 0.0049 | 0.0089 | 0.0534 | 0.0476 |
| Plasma Cells | IGHG1, IGHG2, IGHG3 (Total) | 0.0336 | 0.0682 | 0.0915 | 0.3528 |
| Plasma Cells | IGHG1, IGHG2 (Secretory) | 0.0617 | 0.1114 | 0.2886 | 0.7866 |
| Plasma Cells | IGHM | 0.4783 | 0.9886 | 0.956 | 0.4025 |
| Plasma Cells | IGJ | 0.0598 | 0.0707 | 0.0072 | 0.423 |
| Plasma Cells | IGKC | 0.0627 | 0.0503 | 0.0363 | 0.5083 |
| Plasma Cells | IGLC2 | 0.0052 | 0.0181 | 0.0054 | 0.0602 |
| Plasma Cells | TNFRSF17 | 0.5246 | 0.5025 | 0.1575 | 0.8857 |
| Plasma Cells | TXNDC5 | 0.1776 | 0.2369 | 0.1833 | 0.7982 |
| Interferon | G1P2 | 0.2546 | 0.009 | 0.0188 | 0.0661 |
| Interferon | IFITM3 | 0.8746 | 0.1154 | 0.1802 | 0.5503 |
| Interferon | MX1 | 0.4152 | 0.0149 | 0.2214 | 0.1825 |
| Interferon | OAS1 | 0.6747 | 0.0508 | 0.1732 | 0.2375 |
| Interferon | PLSCR1 | 0.9542 | 0.8888 | 0.9892 | 0.7107 |
| Interferon | SP100 | 0.6631 | 0.3259 | 0.1272 | 0.6232 |

SEQUENCE LISTING

<160> NUMBER OF SEQ ID NOS: 66

<210> SEQ ID NO 1
<211> LENGTH: 7959
<212> TYPE: DNA
<213> ORGANISM: Homo sapiens

<400> SEQUENCE: 1

| | | | | | |
|---|---|---|---|---|---|
| gcacttctcg | cgaggttgca | ggcagtgccg | ggccagacat | ggcggaagag | gaggtggcca | 60 |
| agttggagaa | gcacttgatg | cttctgcggc | aggagtatgt | caagctgcag | aagaagctgg | 120 |
| cggagacaga | gaagcgctgc | gctctcttgg | ctgcgcaggc | aaacaaggag | agcagcagcg | 180 |
| agtccttcat | cagccgtctg | ctggccatcg | tggcagacct | ctacgagcag | gagcagtaca | 240 |
| gcgatctgaa | gataaaggtt | ggggacaggc | acatcagtgc | tcacaagttt | gtcctggcag | 300 |
| cccgcagtga | cagctggagt | ctggctaact | tgtcttccac | taaagagttg | gacctgtcag | 360 |
| atgctaatcc | tgaggtgacg | atgacaatgc | ttcgctggat | ctatacagat | gagctggagt | 420 |
| tcagagagga | tgatgtgttc | ctgactgaac | tgatgaaact | agcaaatcgg | tttcagctac | 480 |
| agctcctcag | ggagagatgt | gagaagggtg | ttatgtctct | agtgaatgtc | aggaactgta | 540 |
| ttcgcttcta | ccagacggca | gaggagctga | tgccagcac | actgatgaac | tactgtgcag | 600 |
| aaattattgc | aagtcattgg | gacgacctga | ggaaggagga | tttcagcagc | atgagcgctc | 660 |
| agttgttata | caaaatgatc | aaatccaaga | cagagtaccc | gctacataaa | gccatcaaag | 720 |
| tggagagaga | agacgtggtc | ttcctgtatc | tgattgaaat | ggattcccag | ctccctggga | 780 |
| agctgaatga | agcggatcat | aacggagatc | tggcattaga | tctagccctc | tcacgacgac | 840 |
| tggagagtat | tgccaccacg | ctggttagtc | acaaagctga | tgtggacatg | gtggacaaga | 900 |
| gtggctggag | cttgttacac | aaaggaatcc | aaagaggaga | tctctttgct | gccactttcc | 960 |
| tcattaagaa | tggggccttt | gtcaacgctg | ctacactggg | tgcccaggag | acaccactgc | 1020 |
| accttgtggc | cttgtacagt | tcaaagaaac | actcagcaga | tgtgatgtct | gagatggcgc | 1080 |
| agattgcaga | ggcccttctg | caggctggtg | ccaaccccaa | catgcaggac | agcaagggga | 1140 |
| ggactccttt | acatgtgtcc | atcatggccg | ggaatgaata | tgtgttcagt | cagctgctgc | 1200 |
| agtgcaaaca | actagattta | gaactcaaag | accacgaggg | cagcacggct | ctgtggctgg | 1260 |
| cagtgcagca | tatcacagtg | tcttctgacc | agtctgtgaa | ccccttcgaa | gatgtccccg | 1320 |
| tggtaaatgg | gacttcattt | gatgagaaca | gctttgcagc | cagactcatc | cagcgcggca | 1380 |
| gccacacaga | cgcacctgac | acggcgacag | gaaactgttt | actacagcgg | gcagctggag | 1440 |
| caggaaacga | ggcagcagct | cttttcctgg | caaccaacgg | tgcccatgtc | aaccacagaa | 1500 |
| acaagtgggg | agaaaccccg | ttgcacacag | cgtgtcggca | tggcctggcc | aacctcacgg | 1560 |
| cagagctcct | gcagcaaggc | gccaacccaa | acctgcagac | ggaggaagct | ctgcctctgc | 1620 |
| caaaggaggc | cgcatccctg | accagcttgg | cggacagcgt | ccatctgcag | acgccactgc | 1680 |
| acatggcgat | cgcctataac | catccggatg | tggtgtctgt | catcctggag | cagaaagcca | 1740 |
| atgctcttca | tgccaccaac | aacttgcaga | tcattccgga | cttcagcctc | aaagattccc | 1800 |
| gagaccagac | tgtgctgggc | ctggcattat | ggactggcat | gcacgcgatc | gcagcccagc | 1860 |
| tgctgggctc | tggagccgcc | atcaatgaca | ccatgtcgga | tgggcagacg | ctactgcaca | 1920 |
| tggccataca | gcggcaggac | agcaagagcg | cactcttcct | gctggagcac | caggcagata | 1980 |
| taaatgtcag | caggactcag | gacggggaga | cagccctcca | gctggccatc | agaaaccagc | 2040 |
| ttccactcgt | agttgatgcc | atatgcaccc | gaggagctga | catgtctgtg | ccagatgaga | 2100 |

```
aggggaaccc cccgctgtgg cttgcattgg caaacaatct ggaggacatc gcatccactc    2160
tggtcagaca tggctgtgat gccacatgct ggggtccggg acctggtggg tgccttcaga    2220
cgctcctgca cagagccatt gatgaaaaca acgagcccac cgcctgcttt cttattcgca    2280
gtggctgtga cgtgaacagt cccagacaac caggcgccaa tggagaagga gaggaagagg    2340
ctagagatgg gcagacccct ttgcatttgg cagcctcttg ggggctggaa gagacagtac    2400
agtgtcttct ggagtttggt gccaacgtga acgcacagga tgcagaagga agaaccccca    2460
tccacgtggc catcagcagc caacacggtg tcatcattca gctgttggtt tctcaccccg    2520
atatccattt gaatgtacga gacagacaag ggctgacccc gtttgcctgt gccatgactt    2580
tcaagaacaa caagtcagcc gaggccattc tcaaacgaga gtccggggct gctgagcagg    2640
tggataacaa gggccggaat tccttcatg tggcagttca gaactctgat attgaaagtg     2700
tgctgttcct gatcagtgtc cacgctaatg tgaattcaag agtccaggat gcctccaagt    2760 tgaccccccct gcacctcgct gtccaagcag gctcagaaat tattgtccgc aatttgcttc    2820
ttgcgggagc caaagtgaac gaattaacca agcatcgcca gactgccctc catcttgctg    2880
cccagcagga cctgcccacc atctgctcag tcctcctaga gaatggcgtg acttttgctg    2940
ccgtggatga aatggaaac aatgctcttc atcttgctgt catgcacggc cggctcaaca     3000
acatccgggt tctcctgaca gagtgcacag tggacgccga agcctttaat ctcagaggcc    3060
agtcaccact gcacattttg ggacaatatg gcaaggagaa tgcagcggcc atctttgatc    3120
tcttcctaga atgcatgccg gggtatcctc tggacaagcc ggatgcagac ggcagcacgg    3180
tgctgctcct ggcatacatg aaagggaacg ccaacttgtg ccgcgccatc gtccggtcgg    3240
gggctcgcct cggggtgaat aacaaccagg gagtcaacat cttcaactac caggtcgcca    3300
ccaagcagct cctgttccga ctgctggata tgctgtccaa ggagcctccg tggtgtgacg    3360
gctcctactg ctatgagtgc actgccaggt tcggagtcac cactcgcaaa caccactgtc    3420
gtcactgcgg acgtcttctt tgccataaat gctcgaccaa ggagattcct attataaagt    3480
ttgatctgaa caagcctgtg cgggtttgca acatttgttt tgatgtactg actctgggtg    3540
gggtttctta gtgagccccc cggagggtcc aggccacgtc cttggtcacc tccccagcag    3600
ctgctctgct caccagcctg accccaccca gagcaggagc tggcgggtgt cttcctgcgg    3660
caatagactg gaacgattaa ggaccatggt gtgatagatc ccatttcaaa tgattccata    3720
tgattgtcag tgtgtgtgtc agactgtgat cgatttcact agatgtctca ctcatcagac    3780
caggccattg ggcctaagtg gtaaatgtga ttaggaatta gacctctccc cattctgcta    3840
gcaacataca gggacacttg gaaaaccatt tccccttcca gtagcttggt gtccatccca    3900
gagcattcat gaagtcttcc cgcctgggct gactgatgag gcagagcctc tcagcgtagg    3960
aagctggctg cttaatgagc tggctttact ctagggtaag tggctgtgga ctttttctgca   4020 cagtgttttc ataaagataa taggatcctc ttgccctgaa gtctttttt cttttacgc     4080 taagctgtat ttttagtgag ctaccccttt taaaaggtg aaatctttct taacagggtt    4140
caaagatgag agctgaaaaa tcgtggcctt aacaactgaa agctttacag tgttcatgct    4200
actgaggtgt caggagtgca gctgggccgc ttgacacctc gtagcagccg tctcattctc    4260
tcgtcttgct gcgtcctgtc tgtggagtcc tcagtcactc tgctgttgga gagtgctgaa    4320
ggaaatgcac ttttactgtg ctgcactttt tatagagctg cattgtcggt gattccaatt    4380
taaaaatcca tattcaaaaa taccctcaca catccctgca tcagtgattc taatgatcag    4440
```

-continued

```
ctttgactgg acctcagctc acacgaatct ccaaggaaaa actctacaga gcatctttta    4500
gagcaagaga ttcatacagg ccaagtgatg agagggggag tcaccaaggc ttcagcccca    4560
agggcatctc cagcctcagg ccggcaggtc ctatgtcctt gacacaaatg cttcttgctg    4620
aaatcctccc tagtgatgct gcgagtgctg ttggtcccag ttctgtgtag cttgccctgc    4680
cccatgaagg gccaccagcc aagggccctg gccacgtgtg cgccacctta ctttggaagt    4740
ctctggcttg tgtgctggat gaggctgcca gaacttgttg ggcgttcatc gctgttagta    4800
catatattaa ccgtgaggtg ttaaactttt cttttgaagg tttggccagt ttctaaaaaa    4860
tgcacattta aagagaagca tctaccacgg ctttaaaaca aaacaactct gagatgaaca    4920
atatgtgtta tactcagaga ttaacaatct caatcataca tactgattct ttcagacatt    4980
taataaccac tacattttt tgcattaatg aagtttgact atatgtgtaa agggactaaa    5040
tatttttgca acagcctgtt ctttgttcat tcttttctgg atagtgtgtc ctctgtattg    5100
cggtagattt atacattctg ttgcctaaat atgtgtgtaa aatgagctga taaactggag    5160
tactacttaa aaaaaagtct gtgatttata agatgtatat gctttctatg tgaatataag    5220
cttgtgcaca atgtttaaaa gaaaaacaat gaattagaag gatcccccg tcccccagtc    5280
tgacatattt catacagaat gtttaaaaga aaaactctgc tagtcttggc aaacatttgg    5340
ccatgtgagg catgtggtca gtttccattt tctattacct ggaaagggcc ataaggaagc    5400
aggcagggct taggtagctt ggttacctaa gttagaaagt aagagaatca tgattcggat    5460
atgaattgaa gtggttggta catggatacc tgttctttaa aaggaatgtg ggagatgagt    5520
caagggtgag gccgattgtt ctgcccatgc cctaccatac caatttcaat aacaatcttg    5580
cctgtcattg cactcagaat cttaagatca tgtttcaaat atgttgattc aaacttgctt    5640
ctaagcctga gtccagggat agcaatggta ctgaccagct atggactggg agaacattga    5700
gtcctgtttt ccattggctt cagggcgcat ccatgtggat ataggaaaag cctcttttcca    5760
cagacttagg aagcccccg accacgcgga cgctcgctgg gctgcactca gcaggctgct    5820
tgagtgggag ctgactccaa catgccctgc cctggctggg actaggcatg cttccagccc    5880
tcccgtgct ctccctgctg tcaacacttg cgtacaaacc tgcctagctg ttgtaagttt    5940
tcatcagtag cttaagtact agtagcaaaa acttaaattc attcagaaag ttgccacttc    6000
tgaatgagta gagcaggaaa agtaaacttt actgaaacat aatttgctgc aacagtcaac    6060
attgttatgc tgaatgtgct ctcaactgcc ctttgctcat cgccagattt attatccagt    6120
gtattcctaa cagtcttttg ttgtcgttgt ttttaaaaca aaggtacgga ccatgtgcta    6180
tatataaatc gaatggctta aactaatttg ctatgatcct ctaacaccga aatttcccat    6240
aaacttaagt gcctcacactt aggactttg aactttcagt catctttttc gtggtgtctc    6300
actgaacgat gtgttagaac atgtgttcca tttggagttt tgggcctgtg cacggtcaac    6360
cccaattacc aatttagttg aggctggatt cgattgctca gttcacctgc cacgttctct    6420
ccaaggagtg gggtctacgt gacctttagt cctctacctc agagccccga gtcatttctg    6480
accaccccgt tctgtgtcct cactcttgtc cctgaatggg tccctgtgtg gatctcagtg    6540
tgtgtgtggt ttctccactc ctccccgctc atgtcccaca cctgccatat tgaaccgttt    6600
ctgcactaat cttctccacg ggcacggagt ggagggaacg tcttgggaaa ggggagagct    6660
tgacctccat ctaggtttct tttatctgga gaaaagaac acttttgaac tatgtaatgc    6720
ttcaccctga aaggcaagct aacgctaact tcccaggtca cagtagcagg aacaaggaag    6780
ggtaatgttt ccatgacaga cacttgcttc ccttgggaca agtcccagaa gaactacctg    6840
```

```
aagcaccaaa gctccccacc ccagcctggt ggcagaggaa gcaggtggca ccaactcacc    6900
aaagggactt gggagccacc ttctcactct gtggaagtac tttagtgaga gctgactggc    6960
aagataaaaa ccctgaaatt cccagaagtt acagatgcct taaagacttt ctttggaaga    7020
tcattgcctg tactattcct ttttttgtgtg gcataaataa tatattaacc tgttacaact    7080
gacaacattg gttttctgca gctagggagt cttgagtcga gactgctcgc cttgatgact    7140
tgctcttttt tggcagatgt gtggagttgg ctgttacgac atccctgtgt gatcccagag    7200
gaggggcagt agctgggcag aaactgcagg cacacatttg ggtggatcac ctggcttcca    7260 gcccttcgg ggtggtgctc agtgtggggt gatggtatca tagaggacca cggcgcttat    7320
cagcattgtt tctttggagt ctgtgtaatg gaatgtattt ttcaaatact gatatttgca    7380
ttttctgtaa caattcctta taataaaatg aagtaaaatt gtgcatttaa agtggaaact    7440
ttaataagac atttgtagtt acttctaatg cagaagtacc aataagcatt aaaaacaaat    7500
tttagaaaac tcctgacgtg aataagtttc ttgaccagct gccctccaga agtttgaat    7560 tccaacattt ttcaggaaca tgctgttgac agcagtaaaa gtagctattt tatgtatgta    7620
tttttaattt ttaaaagttt cagtaggttt ttggggttca ggtggtgttt ggttacgtga    7680
ggttctttag cggtgatttc caggattttg gggcacccat cacccaagca gtgtacactg    7740
gaccctttta tccctcaccc caacccttc ccctgagccc ccaaagtcca ctgtatcatt    7800
cttaatgcct ttacgtcctc atggcttagc tcccgaaaag tagttatttt aaacatacta    7860
gctgcctgaa cttactgtgc ccttggccca gatttcagct catagcaccg agcgtgatca    7920
ctgaggcagt ctcagtcacc gtcacctgac ccctctgaa                          7959

<210> SEQ ID NO 2
<211> LENGTH: 1170
<212> TYPE: PRT
<213> ORGANISM: Homo sapiens

<400> SEQUENCE: 2

Met Ala Glu Glu Glu Val Ala Lys Leu Glu Lys His Leu Met Leu Leu
1               5                   10                  15

Arg Gln Glu Tyr Val Lys Leu Gln Lys Lys Leu Ala Glu Thr Glu Lys
                20                  25                  30

Arg Cys Ala Leu Leu Ala Ala Gln Ala Asn Lys Glu Ser Ser Ser Glu
            35                  40                  45

Ser Phe Ile Ser Arg Leu Leu Ala Ile Val Ala Asp Leu Tyr Glu Gln
        50                  55                  60

Glu Gln Tyr Ser Asp Leu Lys Ile Lys Val Gly Asp Arg His Ile Ser
65                  70                  75                  80

Ala His Lys Phe Val Leu Ala Ala Arg Ser Asp Ser Trp Ser Leu Ala
                85                  90                  95

Asn Leu Ser Ser Thr Lys Glu Leu Asp Leu Ser Asp Ala Asn Pro Glu
            100                 105                 110

Val Thr Met Thr Met Leu Arg Trp Ile Tyr Thr Asp Glu Leu Glu Phe
        115                 120                 125

Arg Glu Asp Asp Val Phe Leu Thr Glu Leu Met Lys Leu Ala Asn Arg
    130                 135                 140

Phe Gln Leu Gln Leu Leu Arg Glu Arg Cys Glu Lys Gly Val Met Ser
145                 150                 155                 160

Leu Val Asn Val Arg Asn Cys Ile Arg Phe Tyr Gln Thr Ala Glu Glu
                165                 170                 175
```

```
Leu Asn Ala Ser Thr Leu Met Asn Tyr Cys Ala Glu Ile Ile Ala Ser
            180                 185                 190

His Trp Asp Asp Leu Arg Lys Glu Asp Phe Ser Ser Met Ser Ala Gln
        195                 200                 205

Leu Leu Tyr Lys Met Ile Lys Ser Lys Thr Glu Tyr Pro Leu His Lys
210                 215                 220

Ala Ile Lys Val Glu Arg Glu Asp Val Val Phe Leu Tyr Leu Ile Glu
225                 230                 235                 240

Met Asp Ser Gln Leu Pro Gly Lys Leu Asn Glu Ala Asp His Asn Gly
                245                 250                 255

Asp Leu Ala Leu Asp Leu Ala Leu Ser Arg Arg Leu Glu Ser Ile Ala
            260                 265                 270

Thr Thr Leu Val Ser His Lys Ala Asp Val Asp Met Val Asp Lys Ser
        275                 280                 285

Gly Trp Ser Leu Leu His Lys Gly Ile Gln Arg Gly Asp Leu Phe Ala
290                 295                 300

Ala Thr Phe Leu Ile Lys Asn Gly Ala Phe Val Asn Ala Ala Thr Leu
305                 310                 315                 320

Gly Ala Gln Glu Thr Pro Leu His Leu Val Ala Leu Tyr Ser Ser Lys
                325                 330                 335

Lys His Ser Ala Asp Val Met Ser Glu Met Ala Gln Ile Ala Glu Ala
            340                 345                 350

Leu Leu Gln Ala Gly Ala Asn Pro Asn Met Gln Asp Ser Lys Gly Arg
        355                 360                 365

Thr Pro Leu His Val Ser Ile Met Ala Gly Asn Glu Tyr Val Phe Ser
370                 375                 380

Gln Leu Leu Gln Cys Lys Gln Leu Asp Leu Glu Leu Lys Asp His Glu
385                 390                 395                 400

Gly Ser Thr Ala Leu Trp Leu Ala Val Gln His Ile Thr Val Ser Ser
                405                 410                 415

Asp Gln Ser Val Asn Pro Phe Glu Asp Val Pro Val Val Asn Gly Thr
            420                 425                 430

Ser Phe Asp Glu Asn Ser Phe Ala Ala Arg Leu Ile Gln Arg Gly Ser
        435                 440                 445

His Thr Asp Ala Pro Asp Thr Ala Thr Gly Asn Cys Leu Leu Gln Arg
450                 455                 460

Ala Ala Gly Ala Gly Asn Glu Ala Ala Ala Leu Phe Leu Ala Thr Asn
465                 470                 475                 480

Gly Ala His Val Asn His Arg Asn Lys Trp Gly Glu Thr Pro Leu His
                485                 490                 495

Thr Ala Cys Arg His Gly Leu Ala Asn Leu Thr Ala Glu Leu Leu Gln
            500                 505                 510

Gln Gly Ala Asn Pro Asn Leu Gln Thr Glu Glu Ala Leu Pro Leu Pro
        515                 520                 525

Lys Glu Ala Ala Ser Leu Thr Ser Leu Ala Asp Ser Val His Leu Gln
530                 535                 540

Thr Pro Leu His Met Ala Ile Ala Tyr Asn His Pro Asp Val Val Ser
545                 550                 555                 560

Val Ile Leu Glu Gln Lys Ala Asn Ala Leu His Ala Thr Asn Asn Leu
                565                 570                 575

Gln Ile Ile Pro Asp Phe Ser Leu Lys Asp Ser Arg Asp Gln Thr Val
            580                 585                 590
```

-continued

```
Leu Gly Leu Ala Leu Trp Thr Gly Met His Thr Ile Ala Ala Gln Leu
            595                 600                 605
Leu Gly Ser Gly Ala Ala Ile Asn Asp Thr Met Ser Asp Gly Gln Thr
610                 615                 620
Leu Leu His Met Ala Ile Gln Arg Gln Asp Ser Lys Ser Ala Leu Phe
625                 630                 635                 640
Leu Leu Glu His Gln Ala Asp Ile Asn Val Ser Arg Thr Gln Asp Gly
                645                 650                 655
Glu Thr Ala Leu Gln Leu Ala Ile Arg Asn Gln Leu Pro Leu Val Val
                660                 665                 670
Asp Ala Ile Cys Thr Arg Gly Ala Asp Met Ser Val Pro Asp Glu Lys
                675                 680                 685
Gly Asn Pro Pro Leu Trp Leu Ala Leu Ala Asn Asn Leu Glu Asp Ile
690                 695                 700
Ala Ser Thr Leu Val Arg His Gly Cys Asp Ala Thr Cys Trp Gly Pro
705                 710                 715                 720
Gly Pro Gly Gly Cys Leu Gln Thr Leu Leu His Arg Ala Ile Asp Glu
                725                 730                 735
Asn Asn Glu Pro Thr Ala Cys Phe Leu Ile Arg Ser Gly Cys Asp Val
                740                 745                 750
Asn Ser Pro Arg Gln Pro Gly Ala Asn Gly Glu Gly Glu Glu Glu Ala
                755                 760                 765
Arg Asp Gly Gln Thr Pro Leu His Leu Ala Ala Ser Trp Gly Leu Glu
770                 775                 780
Glu Thr Val Gln Cys Leu Leu Glu Phe Gly Ala Asn Val Asn Ala Gln
785                 790                 795                 800
Asp Ala Glu Gly Arg Thr Pro Ile His Val Ala Ile Ser Ser Gln His
                805                 810                 815
Gly Val Ile Ile Gln Leu Leu Val Ser His Pro Asp Ile His Leu Asn
                820                 825                 830
Val Arg Asp Arg Gln Gly Leu Thr Pro Phe Ala Cys Ala Met Thr Phe
835                 840                 845
Lys Asn Asn Lys Ser Ala Glu Ala Ile Leu Lys Arg Glu Ser Gly Ala
850                 855                 860
Ala Glu Gln Val Asp Asn Lys Gly Arg Asn Phe Leu His Val Ala Val
865                 870                 875                 880
Gln Asn Ser Asp Ile Glu Ser Val Leu Phe Leu Ile Ser Val His Ala
                885                 890                 895
Asn Val Asn Ser Arg Val Gln Asp Ala Ser Lys Leu Thr Pro Leu His
                900                 905                 910
Leu Ala Val Gln Ala Gly Ser Glu Ile Ile Val Arg Asn Leu Leu Leu
                915                 920                 925
Ala Gly Ala Lys Val Asn Glu Leu Thr Lys His Arg Gln Thr Ala Leu
930                 935                 940
His Leu Ala Ala Gln Gln Asp Leu Pro Thr Ile Cys Ser Val Leu Leu
945                 950                 955                 960
Glu Asn Gly Val Asp Phe Ala Ala Val Asp Glu Asn Gly Asn Asn Ala
                965                 970                 975
Leu His Leu Ala Val Met His Gly Arg Leu Asn Asn Ile Arg Val Leu
                980                 985                 990
Leu Thr Glu Cys Thr Val Asp Ala  Glu Ala Phe Asn Leu  Arg Gly Gln
995                 1000                1005
Ser Pro  Leu His Ile Leu Gly  Gln Tyr Gly Lys Glu  Asn Ala Ala
```

|       |       |       |       |       |       |       |       |       |       |
|-------|-------|-------|-------|-------|-------|-------|-------|-------|-------|
|       |       | 1010  |       |       | 1015  |       |       | 1020  |       |
| Ala   | Ile   | Phe   | Asp   | Leu   | Phe   | Leu   | Glu   | Cys   | Met   | Pro | Gly | Tyr | Pro | Leu |
|       |       | 1025  |       |       | 1030  |       |       | 1035  |       |
| Asp   | Lys   | Pro   | Asp   | Ala   | Asp   | Gly   | Ser   | Thr   | Val   | Leu | Leu | Leu | Ala | Tyr |
|       |       | 1040  |       |       | 1045  |       |       | 1050  |       |
| Met   | Lys   | Gly   | Asn   | Ala   | Asn   | Leu   | Cys   | Arg   | Ala   | Ile | Val | Arg | Ser | Gly |
|       |       | 1055  |       |       | 1060  |       |       | 1065  |       |
| Ala   | Arg   | Leu   | Gly   | Val   | Asn   | Asn   | Asn   | Gln   | Gly   | Val | Asn | Ile | Phe | Asn |
|       |       | 1070  |       |       | 1075  |       |       | 1080  |       |
| Tyr   | Gln   | Val   | Ala   | Thr   | Lys   | Gln   | Leu   | Leu   | Phe   | Arg | Leu | Leu | Asp | Met |
|       |       | 1085  |       |       | 1090  |       |       | 1095  |       |
| Leu   | Ser   | Lys   | Glu   | Pro   | Pro   | Trp   | Cys   | Asp   | Gly   | Ser | Tyr | Cys | Tyr | Glu |
|       |       | 1100  |       |       | 1105  |       |       | 1110  |       |
| Cys   | Thr   | Ala   | Arg   | Phe   | Gly   | Val   | Thr   | Thr   | Arg   | Lys | His | His | Cys | Arg |
|       |       | 1115  |       |       | 1120  |       |       | 1125  |       |
| His   | Cys   | Gly   | Arg   | Leu   | Leu   | Cys   | His   | Lys   | Cys   | Ser | Thr | Lys | Glu | Ile |
|       |       | 1130  |       |       | 1135  |       |       | 1140  |       |
| Pro   | Ile   | Ile   | Lys   | Phe   | Asp   | Leu   | Asn   | Lys   | Pro   | Val | Arg | Val | Cys | Asn |
|       |       | 1145  |       |       | 1150  |       |       | 1155  |       |
| Ile   | Cys   | Phe   | Asp   | Val   | Leu   | Thr   | Leu   | Gly   | Gly   | Val | Ser |
|       |       | 1160  |       |       | 1165  |       |       | 1170  |       |

```
<210> SEQ ID NO 3
<211> LENGTH: 9379
<212> TYPE: DNA
<213> ORGANISM: Homo sapiens

<400> SEQUENCE: 3
```

| | | | | |
|---|---|---|---|---|
| agaatgctct | gcatcgacag | cgggagacga | gacgcgctcg | ggcgtcgctt | tgctgccgct |   60 |
| aggccctgtg | ctcctccccg | cagcggaagg | cctacgaata | cgcggtgtct | tacgtcgctt |  120 |
| cctccgttct | tcgttgcact | ggccaacggg | acgcttagtc | tttcggcaac | ggggtgaaac |  180 |
| cttccttgtg | cctgaaaaaa | cggtacttcg | cggtgtggct | tcggcgcctg | cgcaaaaggc |  240 |
| cgcggggcgc | actccagttc | ccggcaggcc | cgcgacgcg  | cgtttgcgtg | ctgacgcacg |  300 |
| cagttagtcg | tgctgacgtg | cagcgcggcc | caggcggggt | gcgagtggcg | cagttggagc |  360 |
| ccgttgcggc | ccctgaggaa | gcgaggaggc | gtcggcgtcg | gctgaggcgg | gcggaccggc |  420 |
| gaggcgaggc | ggcggcccca | ggcccgaggg | actcgggagc | tcgagcagcg | gcggcggcaa |  480 |
| gacctctccc | cctcggaggc | ggcgggcgga | ggcggcggga | gcgtggtgc  | ccccccggg  |  540 |
| cacggggcca | tgtacaacgg | gatcgggctg | ccgacgcccc | ggggcagcgg | caccaacggc |  600 |
| tacgtccagc | gcaacctgtc | cctggtgcgg | ggccgcgggg | gtgagcggcc | tgactacaag |  660 |
| ggagaggagg | aactgcggcg | cctggaggct | gccctggtga | gcggcctaa  | tcctgacatc |  720 |
| ctggaccacg | agcgcaagcg | gcgcgtcgag | ctgcgatgcc | tcgagctgga | ggagatgatg |  780 |
| gaagagcagg | ggtacgagga | acagcaaatt | caggaaaaag | tggcgacctt | tcgactcatg |  840 |
| ttgctggaga | aggatgtgaa | ccctgggggc | aaggaggaga | ccccagggca | gaggccagcg |  900 |
| gtcacggaga | ctcaccagtt | ggcagaatta | aatgagaaga | gaatgaaag  | actccgtgct |  960 |
| gcctttggca | tcagtgattc | ttacgtagat | ggcagctctt | ttgatcctca | gcgtcgtgcc | 1020 |
| cgagaagcta | acaaccagc  | tcctgagcct | cccaaacctt | acagccttgt | tcgggagtct | 1080 |
| agcagttctc | gctcaccaac | cccaaagcag | aagaagaaga | aaagaagaa  | agatagagga | 1140 |
| cgcaggtcag | agagcagctc | tcctcgacgg | gagagaaaga | aaagctcaaa | gaagaagaag | 1200 |

```
cacaggtcag aatctgagtc caagaaacgt aagcataggt ctcccactcc aaagagcaaa    1260
cgtaaatcta aggacaaaaa gcgaaagcgg tctcgaagta caacaccagc ccccaagagc    1320
cgccgggccc accgttcaac ttctgctgac tctgcttcct cctccgatac ttcccgcagt    1380
cggtctcgaa gtgctgcagc taaaactcat acaactgcct tggctgggcg aagtccttcc    1440
cctgcttcag ggcgacgcgg ggagggagat gcgcctttca gtgaaccagg tactaccagc    1500
acacaacggc ctagtagccc ggagactgct acgaaacagc ctagcagccc ttatgaagac    1560
aaagataaag acaagaagga gaaatctgca actcgaccta gccctctcc ggaaaggagc     1620 agcacaggcc cagaaccacc tgctcccact ccgctccttg ctgagcgaca tggcggctcc    1680
ccacaacccc ttgcaaccac ccccttaagc caggagccag tgaacccccc atctgaggcc    1740
tctccaactc gggaccgttc accacctaag tctcccgaga acttcccca gtcttcttcc     1800 tcagagagca gcccaccatc ccctcaacct accaaagttt ctcggcatgc cagctcttcc    1860
ccagaaagtc ctaaacctgc tccagctcca gggtcccacc gagagatttc ttcttctccc    1920
acatctaaga atcgctcaca tggccgagca aaacgggata aatcacattc tcatacccc    1980 tcccgtagga tggggaggtc ccgtagccct gccaccgcta agagagggcg atctcggtct    2040 cgaacccta ccaagagagg tcattctcga tcccgatctc cccagtggcg taggtccagg    2100
tctgcacaga ggtggggaag atctagaagc ccccagcgac gtggccgctc taggtctcct    2160
cagcgaccag gctggtctag gagcagaaat acccagagaa gaggcaggtc taggtcagca    2220
aggcgaggga ggtcccactc tagatcccca gccactaggg gtagatctcg ttctagaaca    2280
ccagcccgcc ggggcaggtc ccgctctaga acacctgcca ggcggagatc acgatccaga    2340
actcccacca ggcgtaggtc tcggtctaga acaccagccc ggaggggcag gtctcggtct    2400
agaacacctg ctaggcgcag atctaggacc cgatcaccag tacgacgcag gtctcgtagt    2460
agatcaccag ccaggagaag tggcaggtca cgctctagaa ccccagctag acgtggccgc    2520
tcacgctcca gaacccccagc cagacgtggc cgctcacgct ctagaaccccc agctagacgc    2580 agtggtcgct cacgctccag aacaccagcc aggagaggga ggtctcggtc taggacacca    2640
agacgaggaa gatcccgcag tagaagctta gttagacgtg gaagatctca ctctagaaca    2700
cctcaaagaa gaggcagatc tggctcatct tcagagcgga aaaacaaatc cagaacatct    2760
caaagaagaa gcaggtccaa ttcaagccca gaaatgaaga aatctcgcat ttcttcaagg    2820
cggagcaggt ctctctcttc accacggtcc aaagcaaaat ctcgcttgtc tttgaggcgc    2880
agcctttcag ggtcttcccc atgccctaaa caaagtcac agacaccacc caggcgcagt     2940
cgctctggat cctcccaacc taaagctaaa tctagaacgc cacccagacg cagtcgctcc    3000
agttcttctc cgccacctaa acagaaatct aagcaccat caagacaaag tcattccagt     3060
tcatctcctc atcctaaagt gaaatctgga acaccaccga ggcaagggtc cataacaagt    3120
ccccaggcca atgagcaatc tgtaacgcca cagagacgga gctgttttga atcatcacct    3180
gaccctgagt tgaaatctag gacccccttct agacatagct gctcagggtc ctctcctcct    3240
agagtgaaat ctagcacacc tcccagacag agcccatcta ggtcatcatc tccacaaccc    3300
aaagtgaagg caataatatc accaagacaa agaagccatt ctggctcctc ttctccaagt    3360
cctagtaggg tgacgtcgag aacaactcca cggcgaagca gatcagtatc tccctgctcc    3420
aatgtggaat ccagattgtt gccaagatac agtcattctg ggtcctcctc accagatacc    3480
aaagtgaaac ctgaaacacc gccaagacaa agtcactcag ggtctatttc accataccc     3540
```

```
aaagtaaagg cccaaactcc accggggcca agtctttctg atcaaagtc accatgtccc    3600
caagagaagt ctaaagactc actagttcaa agttgccctg atccctctc tctctgtgca    3660
ggagtaaaat ctagcacacc accaggcgag agctattttg gtgtctcatc tctgcaactg    3720
aaaggacaat ctcaaacttc accagaccac agatctgata cttcaagtcc agaagtgaga    3780
cagagtcatt cagaatcacc atctctgcag agcaaatctc aaacatcacc taagggaggt    3840
cggtccaggt cttcatctcc agtcactgag ctggcatcca gatctccaat aagacaagat    3900
agaggtgagt tctcagcgag tcctatgttg aaatctggaa tgtctcctga gcagagcagg    3960
ttccagtctg actcttcttc atatcctaca gtggactcga attctctctt ggggcagagt    4020
agattggaga ctgctgaatc aaaagagaaa atggccttac cccctcagga ggatgctact    4080
gcatcacctc ctagacagaa agacaaattt agtccctttc cagtacagga taggcctgag    4140
tcttcactgg tattcaaaga cacacttaga accccgccaa gggaagaag tggtgctggg    4200
tcatctccag aaacaaaaga gcaaaatagt gcattgccta cgtcaagcca agatgaagag    4260
ttaatggagg tggtagagaa gtctgaagaa cccgcaggcc aaatcctgtc tcatttgtct    4320
tcagaactta agaaaatgtc cacaagtaac tttgaatcat ctcctgaagt agaagaaagg    4380
cctgctgtgt ctttgactct tgatcagagc cagtcacagg cttctttgga agcagtagaa    4440
gtcccttcaa tggcctcatc ttggggtggg ccacattttt ctccagaaca taagaactg    4500
tctaactccc cactcaggga gaacagcttt ggatcacctt tagaatttag aaactcaggc    4560
ccacttggta cagaaatgaa tactggattt tcttctgagg ttaaagaaga tttgaatgga    4620
ccgtttctta atcagctgga aacagatcca tctctagaca tgaaagaaca atcgacaaga    4680
tcctctggac acagcagttc tgagttatcc ccagatgcag tggaaaaggc agggatgtct    4740
tcaaatcaga gcatctcttc acctgtgctt gatgctgtac ccagaacacc ctcgagagaa    4800
agaagtagtt ctgcatcttc tcctgaaatg aaagatggtt tacccagaac tccatcaagg    4860
agaagcaggt ctgggtcttc tccaggactt agagatgggc tgggactcc ctcgaggcac    4920
agcctgtctg ggtcctctcc tggaatgaaa gatatacctg aaacgccatc tagagggaga    4980
agcgaatgtg attcttcccc agaaccgaaa gctttgcctc agactcctag gccgaggagt    5040
cgttctccat catccccaga gctcaacaac aagtgtctta cccccagag agaaagaagc    5100
gggtcagaat catcagttga tcagaaaact gtggctcgga ctcccctggg gcagagaagt    5160
cgttcgggat cctctcaaga acttgatgtg aaacccagtg catcccctca ggaaagaagt    5220
gagtcagact cttctccaga ttctaaagcc aagacaagaa ccccacttcg gcagaggagt    5280
cggtctggat catctccaga ggttgacagc aaatctcgac tatcccctcg gcgcagtagg    5340
tctggttcct cccctgaagt gaaagataag ccaagagcag cacccagggc acagagtggt    5400
tctgattcct ctcctgaacc taaagctcca gcccctcggg cccttcccag acgaagcaga    5460
tcaggttcat caagcaaagg cagaggccct ctcctgaag gaagcagcag taccgagtcc    5520
tctcctgaac atccgcccaa atccagaact gctcgcagag gttccaggtc atcaccagag    5580
cccaagacca agtctcgtac accacctcga cgtcgcagct ctcgatcatc tccggagcta    5640
acaaggaagg ccagactgtc ccgtagaagc cgctctgcct catcctcacc agaaactcgc    5700
tctagaactc ccccaaggca ccggagaagt ccctcagtgt cttccccgga gccagccgaa    5760
aaatcgaggt cttcacgccg acggcgctca gcttcatctc cacgcactaa gacaacctca    5820
aggagaggcc gctctccttc gccaaagcct cgtggactcc agaggtcccg ttcccgctca    5880
aggagagaga aaacaagaac aacccgacgt cgagataggt ctggatcttc tcagtcaacc    5940
```

```
tctcggcgaa gacagcggag ccggtcaagg tcgcgggtta ctcggcggcg gaggggaggc      6000
tctggttatc actcaaggtc acctgcccgg caggaaagtt cccggacctc ctctcgacgc      6060
cgaagaggcc gctctcggac accccaacc agtcggaagc gttctcgctc acgcacatca      6120
ccagccccgt ggaaacgctc tagatctcga gcctctccag ccactcaccg gcgatccagg      6180
tccagaaccc ccctgataag ccgacgtagg tccagatctc gaacttcacc agtcagccgg      6240
agacggtcaa ggtccaggac ttcagtgact cgacgaagat cccggtcaag agcatcccca      6300
gtgagcagaa ggcgatccag atccagaacg ccaccagtaa cccgccgtcg ttcaaggtct      6360
agaacgccaa caacacgccg ccgctcccgt tctagaactc caccagtgac tcgcagaagg      6420
tccagatcca ggactccacc agtaaccagg aggcgatctc gaagcagaac ttcgcctatc      6480
actcgcagaa gatcaagatc cagaacatct ccggtcaccc gaaggagatc tcgatctcgc      6540
acatctccag taactcgaag aaggtcccgc tctcgaacct caccagtgac acgccgccgc      6600
tctaggtccc ggacacctcc agctattcgg cgccgctcta gatctcgaac gccactgtta      6660
ccacgcaaac gttctcgaag tcgctcacca cttgctatcc gccgccgctc cagatcccgt      6720
actccacgaa cagctcgggg taaacggtcc ttaacaagat ctcctccagc catccgcagg      6780
cgttctgcat ctggaagtag ttctgatcgt tcacgatctg ctactcctcc agcaacaaga      6840
aatcattctg gttcacggac acctccagta gcactcaaca gttccagaat gagctgcttc      6900
agtcgtccta gcatgtcccc aacacctctt gatcgctgca gatcacctgg aatgcttgaa      6960 cccttggca gctctagaac acccatgtct gtcctgcagc aagccggcgg ctccatgatg      7020
gatggtccag gtccccgaat acctgaccac cagagaacat ctgtgccaga aaatcatgct      7080
cagtccagga ttgcacttgc cctgacagct atcagtcttg gcaccgctcg gcctcctccg      7140
tccatgtctg ctgctggcct tgctgcaaga atgtcccagg ttccagcccc ggtgcctctc      7200
atgagtctca gaaccgcacc agcagccaac cttgccagca ggattcctgc agcctctgcg      7260
gcagccatga acctagccag cgccaggaca cctgccattc aacagcagt gaacctggct      7320 gactctcgaa cgccagctgc agcagcggcc atgaacttgg ccagcccag acagcggtg      7380 gcaccttcgg ctgtgaacct ggctgaccct cgcactccca cagccccagc tgtgaaccta      7440 gcagggcca gaaccccagc tgccttggca gctctgagtc tcacaggctc tggcacacca      7500
ccaactgctg caaactatcc ctccagctcc agaacaccac aggctccagc ctctgcaaac      7560
ctggtgggtc ctcggtctgc acatgccaca gctcctgtga atattgccgg ctccagaacc      7620
gccgcagcct ggcccccgc gagcctcacc agtgctagga tggctccagc attgtctggt      7680
gcaaacctca ccagccccag ggtgccccctt tctgcctacg agcgtgtcag tggcagaacc      7740
tcaccaccgc tccttgaccg agctaggtcc agaacaccac cgtctgcccc aagccaatct      7800
aggatgacct ctgaacgggc tccctccccct tcctctagaa tgggccaggc tccttcacag      7860
tctcttctcc ctccagcaca ggatcagccg aggtctcctg tgccttctgc tttttcagac      7920
caatcccgtt gtttgattgc ccagaccacc cctgtagcag ggtctcagtc cctttcctct      7980
ggggcagtgg caacgaccac gtcctctgct ggtgatcaca atggcatgct ctctgtccct      8040
gcccctgggg tgcccactc tgatgtgggg gagccacctg cctctactgg ggcccagcag      8100
ccttctgcat tagccgccct gcagccagca aaggagcggc ggagttcctc ctcgtcgtcg      8160
tcgtcctcta gctcctcctc ttcttcatca tcgtcgtcgt cgtcctcctc ctcctctggc      8220
tccagttcta gtgactcaga gggctctagc cttcctgtgc aacctgaggt ggcactgaag      8280
```

-continued

```
agggtcccca gccccacccc agccccaaag gaggctgttc gagagggacg tcctccggag    8340
ccaaccccag ccaaacggaa gaggcgctct agcagttcca gttccagctc ctcctcttca    8400
tcttcctcct cctcctcctc ctcctcttct tcctcctcct cttcctcttc ttcttcttcc    8460
tcctcatctt cctcctcctc gtcgtcttcc tcccctccc ctgctaagcc tggccctcag     8520
gccttgccca aacctgcaag ccccaagaag ccaccccctg gcgagcggag gtcccgcagc    8580
ccccggaagc caatagactc cctcagggac tctcggtccc tcagctactc gcctgtggag    8640
cgtcgccgtc cctcgcccca gccctcacca cgggaccagc agagcagcag cagtgagcgg    8700
ggttcccgga gaggcagcg tggggacagc cgctccccca gccacaagcg caggagggag     8760
acacctagcc ctcggcccat gagacaccgc tcctccaggt ctccataaat tgtctttggg    8820
ggattccacc acacccaatg ctctggagcc acaaggagtg tcccttcttc cccagcagag    8880
ccgtgggagg gtccttgtct gctctccttt gaaccttggc agcccttgga tggagggctc    8940
cctttccctc ccctttttt tttctttgtt cctgtgaaat gttaatctcc gtgagttctt     9000
cctggttcat gtgttctggg gggttgggg tgggagggaa tgcagatggg agttggggga     9060
ggggaggata cagttcagga taccccagcc tggagtcagg gccagggagg catggcccca    9120
cttgtatcca gaagttccca ggggtgattg tgatggtggt tgggactgga ggttgtataa    9180
ggtgttcttg gaaggaaggg gcaggagttg gaattagttg gtccctactg tcccccatga    9240
ggttgtgaac cctccccccc aacttttcat gtttcttaaa ggcattttgg ttttttaaaa    9300
tctgtacagc aagagcaact ttttctgtca aataaaaatg agaaatgcag gaaaaaaaaa    9360 aaaaaaaaa aaaaaaaaa                                                  9379
```

<210> SEQ ID NO 4
<211> LENGTH: 2752
<212> TYPE: PRT
<213> ORGANISM: Homo sapiens

<400> SEQUENCE: 4

```
Met Tyr Asn Gly Ile Gly Leu Pro Thr Pro Arg Gly Ser Gly Thr Asn
1               5                   10                  15

Gly Tyr Val Gln Arg Asn Leu Ser Leu Val Arg Gly Arg Gly Glu
            20                  25                  30

Arg Pro Asp Tyr Lys Gly Glu Glu Leu Arg Leu Glu Ala Ala
        35                  40                  45

Leu Val Lys Arg Pro Asn Pro Asp Ile Leu Asp His Glu Lys Arg
    50                  55                  60

Arg Val Glu Leu Arg Cys Leu Glu Leu Glu Glu Met Met Glu Glu Gln
65                  70                  75                  80

Gly Tyr Glu Glu Gln Gln Ile Gln Glu Lys Val Ala Thr Phe Arg Leu
                85                  90                  95

Met Leu Leu Glu Lys Asp Val Asn Pro Gly Gly Lys Glu Glu Thr Pro
            100                 105                 110

Gly Gln Arg Pro Ala Val Thr Glu Thr His Gln Leu Ala Glu Leu Asn
        115                 120                 125

Glu Lys Lys Asn Glu Arg Leu Arg Ala Ala Phe Gly Ile Ser Asp Ser
    130                 135                 140

Tyr Val Asp Gly Ser Ser Phe Asp Pro Gln Arg Arg Ala Arg Glu Ala
145                 150                 155                 160

Lys Gln Pro Ala Pro Glu Pro Pro Lys Pro Tyr Ser Leu Val Arg Glu
                165                 170                 175
```

-continued

```
Ser Ser Ser Ser Arg Ser Pro Thr Pro Lys Gln Lys Lys Lys Lys
            180             185                 190

Lys Lys Asp Arg Gly Arg Arg Ser Glu Ser Ser Pro Arg Arg Glu
        195             200             205

Arg Lys Lys Ser Ser Lys Lys Lys His Arg Ser Glu Ser Glu Ser
        210             215             220

Lys Lys Arg Lys His Arg Ser Pro Thr Pro Lys Ser Arg Lys Ser
225             230             235             240

Lys Asp Lys Lys Lys Arg Ser Arg Ser Thr Thr Pro Ala Pro Lys
            245             250             255

Ser Arg Arg Ala His Arg Ser Thr Ser Ala Asp Ser Ala Ser Ser
        260             265             270

Asp Thr Ser Arg Ser Arg Ser Arg Ser Ala Ala Ala Lys Thr His Thr
        275             280             285

Thr Ala Leu Ala Gly Arg Ser Pro Ser Pro Ala Ser Gly Arg Arg Gly
        290             295             300

Glu Gly Asp Ala Pro Phe Ser Glu Pro Gly Thr Thr Ser Thr Gln Arg
305             310             315             320

Pro Ser Ser Pro Glu Thr Ala Thr Lys Gln Pro Ser Ser Pro Tyr Glu
            325             330             335

Asp Lys Asp Lys Asp Lys Lys Glu Lys Ser Ala Thr Arg Pro Ser Pro
            340             345             350

Ser Pro Glu Arg Ser Ser Thr Gly Pro Glu Pro Ala Pro Thr Pro
        355             360             365

Leu Leu Ala Glu Arg His Gly Gly Ser Pro Gln Pro Leu Ala Thr Thr
        370             375             380

Pro Leu Ser Gln Glu Pro Val Asn Pro Pro Ser Glu Ala Ser Pro Thr
385             390             395             400

Arg Asp Arg Ser Pro Pro Lys Ser Pro Glu Lys Leu Pro Gln Ser Ser
            405             410             415

Ser Ser Glu Ser Ser Pro Pro Ser Pro Gln Pro Thr Lys Val Ser Arg
            420             425             430

His Ala Ser Ser Pro Glu Ser Pro Lys Pro Ala Pro Ala Pro Gly
        435             440             445

Ser His Arg Glu Ile Ser Ser Pro Thr Ser Lys Asn Arg Ser His
        450             455             460

Gly Arg Ala Lys Arg Asp Lys Ser His Ser His Thr Pro Ser Arg Arg
465             470             475             480

Met Gly Arg Ser Arg Ser Pro Ala Thr Ala Lys Arg Gly Arg Ser Arg
            485             490             495

Ser Arg Thr Pro Thr Lys Arg Gly His Ser Arg Ser Arg Ser Pro Gln
            500             505             510

Trp Arg Arg Ser Arg Ser Ala Gln Arg Trp Gly Arg Ser Arg Ser Pro
        515             520             525

Gln Arg Arg Gly Arg Ser Arg Ser Pro Gln Arg Pro Gly Trp Ser Arg
        530             535             540

Ser Arg Asn Thr Gln Arg Arg Gly Arg Ser Arg Ser Ala Arg Arg Gly
545             550             555             560

Arg Ser His Ser Arg Ser Pro Ala Thr Arg Gly Arg Ser Arg Ser Arg
            565             570             575

Thr Pro Ala Arg Arg Gly Arg Ser Arg Ser Thr Pro Ala Arg Arg
        580             585             590

Arg Ser Arg Ser Arg Thr Pro Thr Arg Arg Arg Ser Arg Ser Arg Thr
```

|     |     |     |     |     |     |     |     |     |     |     |     |
| --- | --- | --- | --- | --- | --- | --- | --- | --- | --- | --- | --- |
|     | 595 |     |     |     | 600 |     |     |     | 605 |     |     |
| Pro | Ala | Arg | Arg | Gly | Arg | Ser | Arg | Thr | Pro | Ala | Arg |
|     | 610 |     |     |     | 615 |     |     |     | 620 |     |     |
| Arg | Arg |     |     |     |     |     |     |     |     |     |     |
| Ser | Arg | Thr | Arg | Ser | Pro | Val | Arg | Arg | Ser | Arg | Ser |
| 625 |     |     |     | 630 |     |     |     | 635 |     |     |     |
| Arg | Ser | Pro |     |     |     |     |     |     |     |     |     |
|     |     |     |     |     |     |     |     |     | 640 |     |     |
| Ala | Arg | Arg | Ser | Gly | Arg | Ser | Arg | Thr | Pro | Ala | Arg |
|     |     |     | 645 |     |     |     | 650 |     |     |     | 655 |
| Arg | Gly |     |     |     |     |     |     |     |     |     |     |
| Arg | Ser | Arg | Ser | Arg | Thr | Pro | Ala | Arg | Gly | Arg | Ser |
|     |     |     | 660 |     |     |     | 665 |     |     |     | 670 |
| Arg | Ser | Arg |     |     |     |     |     |     |     |     |     |
| Thr | Pro | Ala | Arg | Arg | Ser | Gly | Arg | Ser | Arg | Ser | Arg |
|     |     |     | 675 |     |     |     | 680 |     |     |     | 685 |
| Thr | Pro | Ala | Arg |     |     |     |     |     |     |     |     |
| Arg | Gly | Arg | Ser | Arg | Ser | Arg | Thr | Pro | Arg | Arg | Gly |
|     | 690 |     |     |     | 695 |     |     |     | 700 |     |     |
| Arg | Ser | Arg | Ser |     |     |     |     |     |     |     |     |
| Arg | Ser | Leu | Val | Arg | Arg | Gly | Arg | Ser | His | Ser | Arg |
| 705 |     |     |     | 710 |     |     |     | 715 |     |     |     |
| Thr | Pro | Gln | Arg |     |     |     |     |     |     |     |     |
|     |     |     |     |     |     |     |     |     | 720 |     |     |
| Arg | Gly | Arg | Ser | Gly | Ser | Ser | Glu | Arg | Lys | Asn | Lys |
|     |     |     | 725 |     |     |     | 730 |     |     |     | 735 |
| Ser | Arg | Thr |     |     |     |     |     |     |     |     |     |
| Ser | Gln | Arg | Arg | Ser | Arg | Ser | Asn | Ser | Ser | Pro | Glu |
|     |     |     | 740 |     |     |     | 745 |     |     |     | 750 |
| Met | Lys | Lys | Ser |     |     |     |     |     |     |     |     |
| Arg | Ile | Ser | Ser | Arg | Arg | Ser | Arg | Ser | Leu | Ser | Ser |
|     |     |     | 755 |     |     |     | 760 |     |     |     | 765 |
| Pro | Arg | Ser | Lys |     |     |     |     |     |     |     |     |
| Ala | Lys | Ser | Arg | Leu | Ser | Leu | Arg | Arg | Ser | Leu | Ser |
|     | 770 |     |     |     | 775 |     |     |     | 780 |     |     |
| Gly | Ser | Ser | Pro |     |     |     |     |     |     |     |     |
| Cys | Pro | Lys | Gln | Lys | Ser | Gln | Thr | Pro | Arg | Arg | Ser |
| 785 |     |     |     | 790 |     |     |     | 795 |     |     |     |
| Arg | Ser | Gly |     |     |     |     |     |     |     |     |     |
|     |     |     |     |     |     |     |     |     | 800 |     |     |
| Ser | Ser | Gln | Pro | Lys | Ala | Lys | Ser | Arg | Thr | Pro | Pro |
|     |     |     | 805 |     |     |     | 810 |     |     |     | 815 |
| Arg | Arg | Ser | Arg |     |     |     |     |     |     |     |     |
| Ser | Ser | Ser | Pro | Pro | Pro | Lys | Gln | Lys | Ser | Lys | Thr |
|     |     |     | 820 |     |     |     | 825 |     |     |     | 830 |
| Pro | Ser | Arg |     |     |     |     |     |     |     |     |     |
| Gln | Ser | His | Ser | Ser | Ser | Pro | His | Pro | Lys | Val | Lys |
|     |     |     | 835 |     |     |     | 840 |     |     |     | 845 |
| Ser | Gly | Thr |     |     |     |     |     |     |     |     |     |
| Pro | Pro | Arg | Gln | Gly | Ser | Ile | Thr | Ser | Pro | Gln | Ala |
|     | 850 |     |     |     | 855 |     |     |     | 860 |     |     |
| Asn | Glu | Gln | Ser |     |     |     |     |     |     |     |     |
| Val | Thr | Pro | Gln | Arg | Arg | Ser | Cys | Phe | Glu | Ser | Ser |
| 865 |     |     |     | 870 |     |     |     | 875 |     |     |     |
| Pro | Asp | Pro | Glu |     |     |     |     |     |     |     |     |
|     |     |     |     |     |     |     |     |     | 880 |     |     |
| Leu | Lys | Ser | Arg | Thr | Pro | Ser | Arg | His | Ser | Cys | Ser |
|     |     |     | 885 |     |     |     | 890 |     |     |     | 895 |
| Gly | Ser | Ser | Pro |     |     |     |     |     |     |     |     |
| Pro | Arg | Val | Lys | Ser | Ser | Thr | Pro | Pro | Arg | Gln | Ser |
|     |     |     | 900 |     |     |     | 905 |     |     |     | 910 |
| Pro | Ser | Arg | Ser |     |     |     |     |     |     |     |     |
| Ser | Ser | Pro | Gln | Pro | Lys | Val | Lys | Ala | Ile | Ile | Ser |
|     | 915 |     |     |     | 920 |     |     |     | 925 |     |     |
| Pro | Arg | Gln | Arg |     |     |     |     |     |     |     |     |
| Ser | His | Ser | Gly | Ser | Ser | Pro | Ser | Pro | Ser | Arg | Val |
|     | 930 |     |     |     | 935 |     |     |     | 940 |     |     |
| Thr | Ser | Arg |     |     |     |     |     |     |     |     |     |
| Thr | Thr | Pro | Arg | Arg | Ser | Arg | Ser | Val | Ser | Pro | Cys |
| 945 |     |     |     | 950 |     |     |     | 955 |     |     |     |
| Ser | Asn | Val | Glu |     |     |     |     |     |     |     |     |
|     |     |     |     |     |     |     |     |     | 960 |     |     |
| Ser | Arg | Leu | Leu | Pro | Arg | Tyr | Ser | His | Ser | Gly | Ser |
|     |     |     | 965 |     |     |     | 970 |     |     |     | 975 |
| Ser | Ser | Pro | Asp |     |     |     |     |     |     |     |     |
| Thr | Lys | Val | Lys | Pro | Glu | Thr | Pro | Arg | Gln | Ser | His |
|     |     |     | 980 |     |     |     | 985 |     |     |     | 990 |
| Ser | Gly | Ser |     |     |     |     |     |     |     |     |     |
| Ile | Ser | Pro | Tyr | Pro | Lys | Val | Lys | Ala | Gln | Thr | Pro |
|     |     |     | 995 |     |     |     | 1000|     |     |     | 1005|
| Pro | Gly | Pro | Ser |     |     |     |     |     |     |     |     |
| Leu | Ser | Gly | Ser | Lys | Ser | Pro | Cys | Pro | Gln | Glu | Lys |
|     | 1010|     |     |     | 1015|     |     |     |     |     |     |
| Ser | Lys | Asp |     |     |     |     |     |     |     |     |     |
|     |     |     |     |     |     |     |     |     | 1020|     |     |

```
Ser Leu Val Gln Ser Cys Pro Gly Ser Leu Ser Leu Cys Ala Gly
    1025            1030                1035

Val Lys Ser Ser Thr Pro Pro Gly Glu Ser Tyr Phe Gly Val Ser
    1040            1045                1050

Ser Leu Gln Leu Lys Gly Gln Ser Gln Thr Ser Pro Asp His Arg
    1055            1060                1065

Ser Asp Thr Ser Ser Pro Glu Val Arg Gln Ser His Ser Glu Ser
    1070            1075                1080

Pro Ser Leu Gln Ser Lys Ser Gln Thr Ser Pro Lys Gly Gly Arg
    1085            1090                1095

Ser Arg Ser Ser Ser Pro Val Thr Glu Leu Ala Ser Arg Ser Pro
    1100            1105                1110

Ile Arg Gln Asp Arg Gly Glu Phe Ser Ala Ser Pro Met Leu Lys
    1115            1120                1125

Ser Gly Met Ser Pro Glu Gln Ser Arg Phe Gln Ser Asp Ser Ser
    1130            1135                1140

Ser Tyr Pro Thr Val Asp Ser Asn Ser Leu Leu Gly Gln Ser Arg
    1145            1150                1155

Leu Glu Thr Ala Glu Ser Lys Glu Lys Met Ala Leu Pro Pro Gln
    1160            1165                1170

Glu Asp Ala Thr Ala Ser Pro Pro Arg Gln Lys Asp Lys Phe Ser
    1175            1180                1185

Pro Phe Pro Val Gln Asp Arg Pro Glu Ser Ser Leu Val Phe Lys
    1190            1195                1200

Asp Thr Leu Arg Thr Pro Pro Arg Glu Arg Ser Gly Ala Gly Ser
    1205            1210                1215

Ser Pro Glu Thr Lys Glu Gln Asn Ser Ala Leu Pro Thr Ser Ser
    1220            1225                1230

Gln Asp Glu Glu Leu Met Glu Val Val Glu Lys Ser Glu Glu Pro
    1235            1240                1245

Ala Gly Gln Ile Leu Ser His Leu Ser Ser Glu Leu Lys Glu Met
    1250            1255                1260

Ser Thr Ser Asn Phe Glu Ser Ser Pro Glu Val Glu Glu Arg Pro
    1265            1270                1275

Ala Val Ser Leu Thr Leu Asp Gln Ser Gln Ser Gln Ala Ser Leu
    1280            1285                1290

Glu Ala Val Glu Val Pro Ser Met Ala Ser Ser Trp Gly Gly Pro
    1295            1300                1305

His Phe Ser Pro Glu His Lys Glu Leu Ser Asn Ser Pro Leu Arg
    1310            1315                1320

Glu Asn Ser Phe Gly Ser Pro Leu Glu Phe Arg Asn Ser Gly Pro
    1325            1330                1335

Leu Gly Thr Glu Met Asn Thr Gly Phe Ser Ser Glu Val Lys Glu
    1340            1345                1350

Asp Leu Asn Gly Pro Phe Leu Asn Gln Leu Glu Thr Asp Pro Ser
    1355            1360                1365

Leu Asp Met Lys Glu Gln Ser Thr Arg Ser Ser Gly His Ser Ser
    1370            1375                1380

Ser Glu Leu Ser Pro Asp Ala Val Glu Lys Ala Gly Met Ser Ser
    1385            1390                1395

Asn Gln Ser Ile Ser Ser Pro Val Leu Asp Ala Val Pro Arg Thr
    1400            1405                1410
```

```
Pro Ser Arg Glu Arg Ser Ser Ser Ala Ser Ser Pro Glu Met Lys
    1415                1420                1425

Asp Gly Leu Pro Arg Thr Pro Ser Arg Arg Ser Arg Ser Gly Ser
    1430                1435                1440

Ser Pro Gly Leu Arg Asp Gly Ser Gly Thr Pro Ser Arg His Ser
    1445                1450                1455

Leu Ser Gly Ser Ser Pro Gly Met Lys Asp Ile Pro Arg Thr Pro
    1460                1465                1470

Ser Arg Gly Arg Ser Glu Cys Asp Ser Ser Pro Glu Pro Lys Ala
    1475                1480                1485

Leu Pro Gln Thr Pro Arg Pro Arg Ser Arg Ser Pro Ser Ser Pro
    1490                1495                1500

Glu Leu Asn Asn Lys Cys Leu Thr Pro Gln Arg Glu Arg Ser Gly
    1505                1510                1515

Ser Glu Ser Ser Val Asp Gln Lys Thr Val Ala Arg Thr Pro Leu
    1520                1525                1530

Gly Gln Arg Ser Arg Ser Gly Ser Ser Gln Glu Leu Asp Val Lys
    1535                1540                1545

Pro Ser Ala Ser Pro Gln Glu Arg Ser Glu Ser Asp Ser Ser Pro
    1550                1555                1560

Asp Ser Lys Ala Lys Thr Arg Thr Pro Leu Arg Gln Arg Ser Arg
    1565                1570                1575

Ser Gly Ser Ser Pro Glu Val Asp Ser Lys Ser Arg Leu Ser Pro
    1580                1585                1590

Arg Arg Ser Arg Ser Gly Ser Ser Pro Glu Val Lys Asp Lys Pro
    1595                1600                1605

Arg Ala Ala Pro Arg Ala Gln Ser Gly Ser Asp Ser Ser Pro Glu
    1610                1615                1620

Pro Lys Ala Pro Ala Pro Arg Ala Leu Pro Arg Ser Arg Ser
    1625                1630                1635

Gly Ser Ser Ser Lys Gly Arg Gly Pro Ser Pro Glu Gly Ser Ser
    1640                1645                1650

Ser Thr Glu Ser Ser Pro Glu His Pro Pro Lys Ser Arg Thr Ala
    1655                1660                1665

Arg Arg Gly Ser Arg Ser Ser Pro Glu Pro Lys Thr Lys Ser Arg
    1670                1675                1680

Thr Pro Pro Arg Arg Arg Ser Ser Arg Ser Ser Pro Glu Leu Thr
    1685                1690                1695

Arg Lys Ala Arg Leu Ser Arg Arg Ser Arg Ser Ala Ser Ser Ser
    1700                1705                1710

Pro Glu Thr Arg Ser Arg Thr Pro Pro Arg His Arg Arg Ser Pro
    1715                1720                1725

Ser Val Ser Ser Pro Glu Pro Ala Glu Lys Ser Arg Ser Ser Arg
    1730                1735                1740

Arg Arg Arg Ser Ala Ser Ser Pro Arg Thr Lys Thr Thr Ser Arg
    1745                1750                1755

Arg Gly Arg Ser Pro Ser Pro Lys Pro Arg Gly Leu Gln Arg Ser
    1760                1765                1770

Arg Ser Arg Ser Arg Arg Glu Lys Thr Arg Thr Thr Arg Arg Arg
    1775                1780                1785

Asp Arg Ser Gly Ser Ser Gln Ser Thr Ser Arg Arg Gln Arg
    1790                1795                1800

Ser Arg Ser Arg Ser Arg Val Thr Arg Arg Arg Arg Gly Gly Ser
```

-continued

```
             1805                1810                1815
Gly Tyr His Ser Arg Ser Pro Ala Arg Gln Glu Ser Ser Arg Thr
             1820                1825                1830

Ser Ser Arg Arg Arg Arg Gly Arg Ser Arg Thr Pro Pro Thr Ser
             1835                1840                1845

Arg Lys Arg Ser Arg Ser Arg Thr Ser Pro Ala Pro Trp Lys Arg
             1850                1855                1860

Ser Arg Ser Arg Ala Ser Pro Ala Thr His Arg Arg Ser Arg Ser
             1865                1870                1875

Arg Thr Pro Leu Ile Ser Arg Arg Ser Arg Ser Arg Thr Ser
             1880                1885                1890

Pro Val Ser Arg Arg Arg Ser Arg Ser Arg Thr Ser Val Thr Arg
             1895                1900                1905

Arg Arg Ser Arg Ser Arg Ala Ser Pro Val Ser Arg Arg Arg Ser
             1910                1915                1920

Arg Ser Arg Thr Pro Pro Val Thr Arg Arg Ser Arg Ser Arg
             1925                1930                1935

Thr Pro Thr Thr Arg Arg Arg Ser Arg Ser Arg Thr Pro Pro Val
             1940                1945                1950

Thr Arg Arg Arg Ser Arg Ser Arg Thr Pro Pro Val Thr Arg Arg
             1955                1960                1965

Arg Ser Arg Ser Arg Thr Ser Pro Ile Thr Arg Arg Arg Ser Arg
             1970                1975                1980

Ser Arg Thr Ser Pro Val Thr Arg Arg Arg Ser Arg Ser Arg Thr
             1985                1990                1995

Ser Pro Val Thr Arg Arg Arg Ser Arg Ser Arg Thr Ser Pro Val
             2000                2005                2010

Thr Arg Arg Arg Ser Arg Ser Arg Thr Pro Pro Ala Ile Arg Arg
             2015                2020                2025

Arg Ser Arg Ser Arg Thr Pro Leu Leu Pro Arg Lys Arg Ser Arg
             2030                2035                2040

Ser Arg Ser Pro Leu Ala Ile Arg Arg Arg Ser Arg Ser Arg Thr
             2045                2050                2055

Pro Arg Thr Ala Arg Gly Lys Arg Ser Leu Thr Arg Ser Pro Pro
             2060                2065                2070

Ala Ile Arg Arg Arg Ser Ala Ser Gly Ser Ser Ser Asp Arg Ser
             2075                2080                2085

Arg Ser Ala Thr Pro Pro Ala Thr Arg Asn His Ser Gly Ser Arg
             2090                2095                2100

Thr Pro Pro Val Ala Leu Asn Ser Ser Arg Met Ser Cys Phe Ser
             2105                2110                2115

Arg Pro Ser Met Ser Pro Thr Pro Leu Asp Arg Cys Arg Ser Pro
             2120                2125                2130

Gly Met Leu Glu Pro Leu Gly Ser Ser Arg Thr Pro Met Ser Val
             2135                2140                2145

Leu Gln Gln Ala Gly Gly Ser Met Met Asp Gly Pro Gly Pro Arg
             2150                2155                2160

Ile Pro Asp His Gln Arg Thr Ser Val Pro Glu Asn His Ala Gln
             2165                2170                2175

Ser Arg Ile Ala Leu Ala Leu Thr Ala Ile Ser Leu Gly Thr Ala
             2180                2185                2190

Arg Pro Pro Pro Ser Met Ser Ala Ala Gly Leu Ala Ala Arg Met
             2195                2200                2205
```

```
Ser Gln Val Pro Ala Pro Val Pro Leu Met Ser Leu Arg Thr Ala
2210                2215                2220

Pro Ala Ala Asn Leu Ala Ser Arg Ile Pro Ala Ser Ala Ala
2225                2230                2235

Ala Met Asn Leu Ala Ser Ala Arg Thr Pro Ala Ile Pro Thr Ala
2240                2245                2250

Val Asn Leu Ala Asp Ser Arg Thr Pro Ala Ala Ala Ala Met
2255                2260                2265

Asn Leu Ala Ser Pro Arg Thr Ala Val Ala Pro Ser Ala Val Asn
2270                2275                2280

Leu Ala Asp Pro Arg Thr Pro Thr Ala Pro Ala Val Asn Leu Ala
2285                2290                2295

Gly Ala Arg Thr Pro Ala Ala Leu Ala Ala Leu Ser Leu Thr Gly
2300                2305                2310

Ser Gly Thr Pro Pro Thr Ala Ala Asn Tyr Pro Ser Ser Ser Arg
2315                2320                2325

Thr Pro Gln Ala Pro Ala Ser Ala Asn Leu Val Gly Pro Arg Ser
2330                2335                2340

Ala His Ala Thr Ala Pro Val Asn Ile Ala Gly Ser Arg Thr Ala
2345                2350                2355

Ala Ala Leu Ala Pro Ala Ser Leu Thr Ser Ala Arg Met Ala Pro
2360                2365                2370

Ala Leu Ser Gly Ala Asn Leu Thr Ser Pro Arg Val Pro Leu Ser
2375                2380                2385

Ala Tyr Glu Arg Val Ser Gly Arg Thr Ser Pro Pro Leu Leu Asp
2390                2395                2400

Arg Ala Arg Ser Arg Thr Pro Pro Ser Ala Pro Ser Gln Ser Arg
2405                2410                2415

Met Thr Ser Glu Arg Ala Pro Ser Pro Ser Ser Arg Met Gly Gln
2420                2425                2430

Ala Pro Ser Gln Ser Leu Leu Pro Pro Ala Gln Asp Gln Pro Arg
2435                2440                2445

Ser Pro Val Pro Ser Ala Phe Ser Asp Gln Ser Arg Cys Leu Ile
2450                2455                2460

Ala Gln Thr Thr Pro Val Ala Gly Ser Gln Ser Leu Ser Ser Gly
2465                2470                2475

Ala Val Ala Thr Thr Thr Ser Ser Ala Gly Asp His Asn Gly Met
2480                2485                2490

Leu Ser Val Pro Ala Pro Gly Val Pro His Ser Asp Val Gly Glu
2495                2500                2505

Pro Pro Ala Ser Thr Gly Ala Gln Gln Pro Ser Ala Leu Ala Ala
2510                2515                2520

Leu Gln Pro Ala Lys Glu Arg Arg Ser Ser Ser Ser Ser Ser Ser
2525                2530                2535

Ser Ser Ser Ser Ser Ser Ser Ser Ser Ser Ser Ser Ser Ser Ser
2540                2545                2550

Ser Ser Ser Gly Ser Ser Ser Ser Asp Ser Glu Gly Ser Ser Leu
2555                2560                2565

Pro Val Gln Pro Glu Val Ala Leu Lys Arg Val Pro Ser Pro Thr
2570                2575                2580

Pro Ala Pro Lys Glu Ala Val Arg Glu Gly Arg Pro Pro Glu Pro
2585                2590                2595
```

-continued

| | | | | | | | | | | | | |
|---|---|---|---|---|---|---|---|---|---|---|---|---|
|Thr|Pro|Ala|Lys|Arg|Lys|Arg|Arg|Ser|Ser|Ser|Ser|Ser|Ser|
| |2600| | | |2605| | | |2610| | | |
|Ser|Ser|Ser|Ser|Ser|Ser|Ser|Ser|Ser|Ser|Ser|Ser|Ser|
| |2615| | | |2620| | | |2625| | | |
|Ser|Ser|Ser|Ser|Ser|Ser|Ser|Ser|Ser|Ser|Ser|Ser|Ser|
| |2630| | | |2635| | | |2640| | | |
|Ser|Ser|Ser|Ser|Ser|Pro|Ser|Pro|Ala|Lys|Pro|Gly|Pro|Gln|Ala|
| |2645| | | |2650| | | |2655| | | |
|Leu|Pro|Lys|Pro|Ala|Ser|Pro|Lys|Lys|Pro|Pro|Gly|Glu|Arg|
| |2660| | | |2665| | | |2670| | | |
|Arg|Ser|Arg|Ser|Pro|Arg|Lys|Pro|Ile|Asp|Ser|Leu|Arg|Asp|Ser|
| |2675| | | |2680| | | |2685| | | |
|Arg|Ser|Leu|Ser|Tyr|Ser|Pro|Val|Glu|Arg|Arg|Pro|Ser|Pro|
| |2690| | | |2695| | | |2700| | | |
|Gln|Pro|Ser|Pro|Arg|Asp|Gln|Gln|Ser|Ser|Ser|Glu|Arg|Gly|
| |2705| | | |2710| | | |2715| | | |
|Ser|Arg|Arg|Gly|Gln|Arg|Gly|Asp|Ser|Arg|Ser|Pro|Ser|His|Lys|
| |2720| | | |2725| | | |2730| | | |
|Arg|Arg|Arg|Glu|Thr|Pro|Ser|Pro|Arg|Pro|Met|Arg|His|Arg|Ser|
| |2735| | | |2740| | | |2745| | | |
|Ser|Arg|Ser|Pro|
| |2750| | |

<210> SEQ ID NO 5
<211> LENGTH: 7817
<212> TYPE: DNA
<213> ORGANISM: Homo sapiens

<400> SEQUENCE: 5

```
gaaagtgacc ggaagtaacc gccgggccaa gatggctgca gaggaagggg tcgcgagtgc      60
tgcttccgcc ggcggtagct ggggcaccgc ggccatgggg cgggttctac cgatgctgtt     120
ggtgccagtc cccgccgagg cgatggggca gctcggctcc cgggcgcagc tgcgcacaca     180
gccggaggct ctggggagcc tgacggctgc gggcagcctc caagtgcttt ctttgacgcc     240
tggcagccgg ggcgggggtc gctgctgcct ggagggcccc ttctggcact ttctatggga     300
ggattctcgt aacagcagca caccaactga aaagcccaaa ctgctcgctc ttggtgaaaa     360
ttatgaactg cttatctatg aatttaattt gaaagatgga agatgtgatg caaccatttt     420
gtatagctgt agtagggagg cattgcaaaa gctcattgac gatcaagata tcagtatttc     480
cttattgtct ttgagaatcc tgtcatttca caataacaca tcattactgt tcatcaacaa     540
atgtgtcatc ctacatatta tatttcctga agagatgct gcaattagag tactcaactg     600
tttcacactt cccttgcctg cacaggcagt ggacatgatt attgacacgc agctctgcag     660
aggaattctt tttgttttga gtagtttagg ctggatctac attttgatg ttgtggatgg     720
tacatatgta gctcatgtgg atttagcact tcacaaagaa gacatgtgta atgagcagca     780
acaggagcca gccaagattt cttcatttac ttcactgaaa gtttctcaag acctcgatgt     840
tgcagtgatt gtcagctcct ccaactccgc agttgctctt aacttaaatt tgtatttcag     900
gcaacaccca ggacacctac tgtgtgaaag aatactagaa gatcttccta ttcaaggacc     960
taagggcgta gatgaagatg atcctgttaa ctctgcctac aacatgaaac tggccaagtt    1020
ttccttccaa attgataggt cttggaaagc ccagctatca tcattgaatg aaacaataaa    1080
gaactccaaa ctggaggttt cctgttgtgc tccatggttc caggatattt tgcatttgga    1140
```

```
gtcacctgaa tctggtaacc acagtacaag tgtgcagagc tgggccttca ttccacagga    1200
cataatgcat gggcaatata atgttctaca gaaagatcat gccaagacca gtgatccagg    1260
aagatcatgg aaaataatgc acatcagtga acaagaggaa cccatagagc ttaaatgtgt    1320
gtctgtgaca ggattcactg cactgtttac ttgggaagtg gaaaggatgg gctataccat    1380
taccctctgg gatttggaga cccagggcat gcagtgtttt tcccttggca caaagtgtat    1440
tcctgtagac agtagtggag accagcagct gtgctttgtt ttgacagaga atggactctc    1500
tctgattttg tttggtttga ctcaagaaga gttttttaaac agactcatga tccatggaag    1560
tgccagcact gtggacactc tttgtcatct caatggctgg ggaaggtgct caattcccat    1620
acatgcacta gaggccggga tagaaaatcg tcagctggac acagtaaatt tcttttttgaa    1680 gagcaaggaa aatcttttta atccatcctc aaaatcttct gtatctgatc agtttgatca    1740
cttgtcatcc catttatatt taagaaatgt ggaagagctg ataccagcat tggatttact    1800
ttgctcggca attagagaaa gttattctga accccaaagc aaacactttt cagaacaatt    1860
gcttaatctt acactgtctt tccttaacaa ccaaataaag gagcttttca ttcacactga    1920
agaactagat gaacatctgc aaaaaggagt gaacattttg actagctaca ttaatgaact    1980
tcgaaccttc atgataaagt ttccttggaa gctaacagat gctatagatg aatatgatgt    2040
acatgaaaat gtccccaaag taaggagag caatatatgg aagaaactca gctttgagga    2100
agttattgcc agcgccattt taaacaacaa ataccagag gcacagactt tcttcaggat    2160
tgatagtcat tctgctcaaa aacttgagga gcttattggc ataggcctaa atttggtctt    2220
tgacaattta aaaaagaaca atataaagga agcctctgaa cttttgaaga atatggggtt    2280
tgatgtaaaa ggccaattgc tcaagatctg cttctataca actaataaaa atatacgtga    2340 cttttttggtt gaaattttaa aagaaaaaaa ttatttttct gaaaagagaa aagaactat    2400 agacttcgtg catcaagttg agaagcttta tttgggacat ttccaagaaa atatgcaaat    2460
ccagtcattt cccaggtact ggataaagga acaagatttt ttcaagcaca gtctgttttt    2520
ggactcattc ctgaaatatg attgtaaaga tgaatttaac aaacaggacc atagaattgt    2580
gttaaattgg gctctgtggt gggatcaact aacacaagaa tccatccttc tccccaggat    2640
aagtccagaa gaatacaaat catattcccc tgaagccctc tggagatacc tcacagctcg    2700
ccatgattgg ttaaacatta tcttatggat tggagaattt caaacccagc atagttatgc    2760
ttcacttcag cagaacaaat ggccccttct gactgttgat gttattaacc agaatacttc    2820
ctgtaacaac tacatgagga atgaaatttt agataagctg gccaggaatg gggtttttt    2880 ggcatctgaa ctggaagact ttgaatgctt cctcctaaga ctgagccgta ttggaggtgt    2940
aatacaggat accctccctg ttcaaaacta caagaccaaa gaaggttggg atttccattc    3000
tcaattcatt ctctattgtt tggagcacag tctgcagcat cttctttatg tctaccttga    3060
ctgttacaaa cttagtcctg aaaattgtcc ctttttggaa aaaaaagagt acatgaagc    3120 acacccttgg tttgaatttt tagttcagtg tcgacaagtt gccagtaact taacagatcc    3180
caaactgatc ttccaggcta gccttgcaaa tgctcagatt ttgattccca ccaatcaggc    3240
cagtgtaagc agtatgctat ggaaggaca taccctcctg gcccttgcta ctacaatgta    3300
ttctcctggg ggtgtcagtc aggttgttca gaatgaagaa aatgaaaact gtttgaagaa    3360
agtggatccc cagctattga agatggcatt aactccttac cccaagctaa aaactgctct    3420
cttcccacag tgcactcctc ctagtgtcct gccatctgat attacaatct accaccttat    3480
tcagtcatta tcacccttg atcctagcag attgtttggc tggcagtctg ctaacacact    3540
```

```
agctatagga gatgcatgga gtcatctccc acatttctct agccctgacc tggttaataa    3600
atatgctata gtggaacgtc tgaattttgc ttattattta cataatgggc ggccatcatt    3660
tgcatttggt acttttctgg tccaggaatt aatcaagagc aagactccca agcagctgat    3720
ccagcaagta ggcaatgaag cctatgttat agggctctcc tccttccaca taccttcaat    3780
aggagctgca tgtgtttgtt tcttagaatt gcttggcctt gacagcctca agctcagagt    3840
tgatatgaaa gtggccaata taattttgag ctacaagtgc agaaatgaag atgctcagta    3900
cagctttatc agagagtctg tagccgaaaa actatctaaa ctagctgatg gtgaaaagac    3960
aaccacagaa gaattgcttg ttctcttaga agaaggtaca tggaacagca ttcagcaaca    4020
ggaaataaag aggttatcca gtgaatctag cagccaatgg gcattagtgg tgcagttctg    4080
caggctacac aatatgaaac taagcatatc ttaccttaga gaatgtgcca agcaaatga    4140
ttggctgcag ttcattattc acagccaact ccacaactac cacccagcag aggtgaaatc    4200
ccttatccag tacttcagcc cagtcattca agaccactta aggctggctt ttgagaactt    4260
gccctcagtg cccacctcca aaatggacag cgatcaagtc tgcaataagt gcccccagga    4320
acttcaagga agcaaacaag agatgaccga tttatttgaa attctgctcc aatgctcaga    4380
ggagccagac tcctggcact ggcttctggt tgaagcagtg aaacaacagg cccctatcct    4440
cagtgttctg gcctcatgtc tccagggtgc cagtgccatt tcttgtctct gtgtttggat    4500
catcacttct gtggaggaca tgttgcaac tgaagcaatg ggacacattc aggactcaac    4560
agaggaccat acctggaacc ttgaggatct ttcagtcatc tggagaacat tattaacaag    4620
acaaaagagc aaaactctca tcagaggttt ccagcttttc tttaaggatt ccccgttact    4680
actggtgatg gagatgtatg aactgtgtat gttcttcagg aattataaag aagctgaagc    4740
taaacttctg gagtttcaga agagccttga aacgcttaac acagcagcca caaaggtcca    4800
ccctgtcatc cctgccatgt ggctggagga tcaggtgtgt ttccttttga agcttatgct    4860
acagcagtgt aagacccagt atgagctggg gaagctttta cagctctttg ttgaaagaga    4920
gcatctcttc tctgatggtc cagatgtgaa aaagctttgc atcctttgcc agattttgaa    4980
ggatacatcc atagccatta atcatacaat tattaccagc tacagcattg agaatcttca    5040
gcatgaatgt agatctattt tggaaagact gcagacagat ggacaattcg ctttggccag    5100
gagggtagca gaattagctg agttacctgt ggacaacttg gttattaaag agataacaca    5160
ggaaatgcag accctaaaac acattgaaca gtggtcacta aaacaagcaa gaattgactt    5220
ctggaaaaaa tgccatgaga attttaagaa aaattcaatt tcaagcaaag cagcttcttc    5280
cttttctca acccaggccc atgtggcatg tgagcaccca actggatgga gcagcatgga    5340
ggagcgccat ctgctgctca ccttggcagg gcactggctt gcccaggagg acgtggtgcc    5400
cttggataag ctggaggagc tggagaagca gatctggctg tgccgcatca cccagcacac    5460
tcttggaaga aatcaggagg aaacagagcc cagattttct cgacagatct caactagtgg    5520
tgaactttcc tttgatagtt tagccagtga gttttccttc tccaagttgg ctgctctgaa    5580
cacatcaaaa tacttagaac ttaacagcct tccatccaaa gagacatgcg agaatagatt    5640
ggattggaaa gagcaggagt cactaaactt tttgattggg cgcctactgg atgatggctg    5700
tgtgcatgaa gcaagtagag tatgccggta ttttcatttt tataatccag atgtcgcctt    5760
ggtattgcac tgcagagcac tggcctcagg ggaagctagt atggaggatc tgcacccaga    5820
gatccatgct ctcctacaaa gtgctgagct gcttgaggaa gaagcacccg acattcccct    5880
```

| | | |
|---|---|---|
| aaggagagtc cacagcactt caagtctgga tagtcagaag tttgtgacag tgccctccag | 5940 |
| taatgaagtg gtaactaacc tggaagtgct gacaagcaaa tgcctccatg ggaagaacta | 6000 |
| ctgtcgacag gtcctctgtc tgtatgatct tgccaaggag ttgggctgtt cctacacaga | 6060 |
| tgttgctgct caggatggtg aagccatgct ccggaaaatc ttggcctctc agcagcctga | 6120 |
| ccgatgcaaa cgagcccagg ccttcatcag cacacagggc cttaagccag atactgtggc | 6180 |
| tgaactcgtg gcagaagagg tgacacggga gctgcttact tcatcacagg gaacaggaca | 6240 |
| taagcagatg ttcaacccaa cagaggaaag ccagacattt cttcagctga ccactctgtg | 6300 |
| tcaagaccgc acattggtag gcatgaagtt gttggataag atttcctccg ttccccatgg | 6360 |
| ggaactgtct tgcaccacag agctcctgat cctggcccat cattgcttca ccctgacgtg | 6420 |
| ccacatggag ggcatcatcc gagtcctaca ggccgcccac atgctcacag ataaccacct | 6480 |
| ggcccccagt gaggagtatg gctggtggt acggctcctc actggcattg aaggtacaa | 6540 |
| cgagatgaca tacatatttg atttgctgca taaaaagcac tactttgaag tgctaatgag | 6600 |
| gaagaagttg gatccgagtg gtaccctgaa acagccctg ctggactaca tcaaacgctg | 6660 |
| ccgtcctgga gacagtgaaa agcacaatat gattgccctg tgcttcagca tgtgccggga | 6720 |
| gattggcgag aaccacgagg cagctgcccg catccaactg aaattgattg agtctcagcc | 6780 |
| ctgggaggac agcctcaagg atgggcacca gctgaaacaa ctgctgctga aggccctgac | 6840 |
| tctgatgttg gatgcagcag agagttatgc caaggactcc tgtgtgcgac aggcccagca | 6900 |
| ctgtcagcgg ctcaccaagt tgataactct gcagattcac tttctgaaca ctggccagaa | 6960 |
| cacaatgctc atcaacttgg gccgccacaa gctgatggac tgtattctgg ccctacctcg | 7020 |
| gttctaccag gcttctattg tggctgaggc ctacgatttt gttccagatt gggctgaaat | 7080 |
| tttataccag caagtgattc ttaaaggaga ctttaattac ttggaagaat ttaagcagca | 7140 |
| aaggttatta aagtccagta tatttgaaga gatttccaaa aaatataaac aacatcagcc | 7200 |
| tactgacatg gtcatggaaa acctgaagaa attactcaca tattgtgaag atgtttacct | 7260 |
| gtattacaag ttggcatacg aacacaagtt ttatgaaatt gtaaatgtgc ttctgaagga | 7320 |
| ccctcagaca ggttgctgtc taaggacat gctagcaggt tagatgattt cataggtgtc | 7380 |
| tgttttcttg tactgttagc agattctgac agatgtgatg agaagaagaa tgcattggag | 7440 |
| atctttgcta aagttgaaca atcccggtac tgtaccatat cagtcctttg tgggtagtag | 7500 |
| gtagcaagta agaaactttt caggaggaaa ttcctattta aaatagattg attttagatg | 7560 |
| attgttcatc cacaccattt tatatagata ctagtattaa gatcaaaagc ttcctcttcc | 7620 |
| tcaggacagc ttctacttta gatgatccaa taatgattaa agaataccctg tacctgcaga | 7680 |
| ttccagtttc aaagaaattt aattattatt tacacagtta aggaacaggt gatacatttt | 7740 |
| catttgttag aaactgatct ttctgtaata aaatagattt tcaattcaaa aaaaaaaaa | 7800 |
| aaaaaaaaaa aaaaaaa | 7817 |

<210> SEQ ID NO 6
<211> LENGTH: 2443
<212> TYPE: PRT
<213> ORGANISM: Homo sapiens

<400> SEQUENCE: 6

Met Ala Ala Glu Glu Gly Val Ala Ser Ala Ala Ser Ala Gly Gly Ser
1               5                   10                  15

Trp Gly Thr Ala Ala Met Gly Arg Val Leu Pro Met Leu Leu Val Pro
            20                  25                  30

```
Val Pro Ala Glu Ala Met Gly Gln Leu Gly Ser Arg Ala Gln Leu Arg
         35                  40                  45

Thr Gln Pro Glu Ala Leu Gly Ser Leu Thr Ala Ala Gly Ser Leu Gln
     50                  55                  60

Val Leu Ser Leu Thr Pro Gly Ser Arg Gly Gly Gly Arg Cys Cys Leu
 65              70                  75                      80

Glu Gly Pro Phe Trp His Phe Leu Trp Glu Asp Ser Arg Asn Ser Ser
                 85                  90                  95

Thr Pro Thr Glu Lys Pro Lys Leu Leu Ala Leu Gly Glu Asn Tyr Glu
            100                 105                 110

Leu Leu Ile Tyr Glu Phe Asn Leu Lys Asp Gly Arg Cys Asp Ala Thr
            115                 120                 125

Ile Leu Tyr Ser Cys Ser Arg Glu Ala Leu Gln Lys Leu Ile Asp Asp
        130                 135                 140

Gln Asp Ile Ser Ile Ser Leu Leu Ser Leu Arg Ile Leu Ser Phe His
145                 150                 155                 160

Asn Asn Thr Ser Leu Leu Phe Ile Asn Lys Cys Val Ile Leu His Ile
                165                 170                 175

Ile Phe Pro Glu Arg Asp Ala Ala Ile Arg Val Leu Asn Cys Phe Thr
                180                 185                 190

Leu Pro Leu Pro Ala Gln Ala Val Asp Met Ile Ile Asp Thr Gln Leu
                195                 200                 205

Cys Arg Gly Ile Leu Phe Val Leu Ser Ser Leu Gly Trp Ile Tyr Ile
        210                 215                 220

Phe Asp Val Val Asp Gly Thr Tyr Val Ala His Val Asp Leu Ala Leu
225                 230                 235                 240

His Lys Glu Asp Met Cys Asn Glu Gln Gln Gln Glu Pro Ala Lys Ile
                245                 250                 255

Ser Ser Phe Thr Ser Leu Lys Val Ser Gln Asp Leu Asp Val Ala Val
                260                 265                 270

Ile Val Ser Ser Ser Asn Ser Ala Val Ala Leu Asn Leu Asn Leu Tyr
        275                 280                 285

Phe Arg Gln His Pro Gly His Leu Leu Cys Glu Arg Ile Leu Glu Asp
        290                 295                 300

Leu Pro Ile Gln Gly Pro Lys Gly Val Asp Glu Asp Pro Val Asn
305                 310                 315                 320

Ser Ala Tyr Asn Met Lys Leu Ala Lys Phe Ser Phe Gln Ile Asp Arg
                325                 330                 335

Ser Trp Lys Ala Gln Leu Ser Ser Leu Asn Glu Thr Ile Lys Asn Ser
                340                 345                 350

Lys Leu Glu Val Ser Cys Cys Ala Pro Trp Phe Gln Asp Ile Leu His
            355                 360                 365

Leu Glu Ser Pro Glu Ser Gly Asn His Ser Thr Ser Val Gln Ser Trp
        370                 375                 380

Ala Phe Ile Pro Gln Asp Ile Met His Gly Gln Tyr Asn Val Leu Gln
385                 390                 395                 400

Lys Asp His Ala Lys Thr Ser Asp Pro Gly Arg Ser Trp Lys Ile Met
                405                 410                 415

His Ile Ser Glu Gln Glu Pro Ile Glu Leu Lys Cys Val Ser Val
                420                 425                 430

Thr Gly Phe Thr Ala Leu Phe Thr Trp Glu Val Glu Arg Met Gly Tyr
            435                 440                 445
```

-continued

```
Thr Ile Thr Leu Trp Asp Leu Glu Thr Gln Gly Met Gln Cys Phe Ser
    450                 455                 460
Leu Gly Thr Lys Cys Ile Pro Val Asp Ser Ser Gly Asp Gln Gln Leu
465                 470                 475                 480
Cys Phe Val Leu Thr Glu Asn Gly Leu Ser Leu Ile Leu Phe Gly Leu
                485                 490                 495
Thr Gln Glu Glu Phe Leu Asn Arg Leu Met Ile His Gly Ser Ala Ser
            500                 505                 510
Thr Val Asp Thr Leu Cys His Leu Asn Gly Trp Gly Arg Cys Ser Ile
        515                 520                 525
Pro Ile His Ala Leu Glu Ala Gly Ile Glu Asn Arg Gln Leu Asp Thr
    530                 535                 540
Val Asn Phe Phe Leu Lys Ser Lys Glu Asn Leu Phe Asn Pro Ser Ser
545                 550                 555                 560
Lys Ser Ser Val Ser Asp Gln Phe Asp His Leu Ser Ser His Leu Tyr
                565                 570                 575
Leu Arg Asn Val Glu Glu Leu Ile Pro Ala Leu Asp Leu Leu Cys Ser
            580                 585                 590
Ala Ile Arg Glu Ser Tyr Ser Glu Pro Gln Ser Lys His Phe Ser Glu
        595                 600                 605
Gln Leu Leu Asn Leu Thr Leu Ser Phe Leu Asn Asn Gln Ile Lys Glu
    610                 615                 620
Leu Phe Ile His Thr Glu Glu Leu Asp Glu His Leu Gln Lys Gly Val
625                 630                 635                 640
Asn Ile Leu Thr Ser Tyr Ile Asn Glu Leu Arg Thr Phe Met Ile Lys
                645                 650                 655
Phe Pro Trp Lys Leu Thr Asp Ala Ile Asp Glu Tyr Asp Val His Glu
            660                 665                 670
Asn Val Pro Lys Val Lys Glu Ser Asn Ile Trp Lys Lys Leu Ser Phe
        675                 680                 685
Glu Glu Val Ile Ala Ser Ala Ile Leu Asn Asn Lys Ile Pro Glu Ala
    690                 695                 700
Gln Thr Phe Phe Arg Ile Asp Ser His Ser Ala Gln Lys Leu Glu Glu
705                 710                 715                 720
Leu Ile Gly Ile Gly Leu Asn Leu Val Phe Asp Asn Leu Lys Lys Asn
                725                 730                 735
Asn Ile Lys Glu Ala Ser Glu Leu Leu Lys Asn Met Gly Phe Asp Val
            740                 745                 750
Lys Gly Gln Leu Leu Lys Ile Cys Phe Tyr Thr Thr Asn Lys Asn Ile
        755                 760                 765
Arg Asp Phe Leu Val Glu Ile Leu Lys Glu Lys Asn Tyr Phe Ser Glu
    770                 775                 780
Lys Glu Lys Arg Thr Ile Asp Phe Val His Gln Val Glu Lys Leu Tyr
785                 790                 795                 800
Leu Gly His Phe Gln Glu Asn Met Gln Ile Gln Ser Phe Pro Arg Tyr
                805                 810                 815
Trp Ile Lys Glu Gln Asp Phe Phe Lys His Lys Ser Val Leu Asp Ser
            820                 825                 830
Phe Leu Lys Tyr Asp Cys Lys Asp Glu Phe Asn Lys Gln Asp His Arg
        835                 840                 845
Ile Val Leu Asn Trp Ala Leu Trp Trp Asp Gln Leu Thr Gln Glu Ser
    850                 855                 860
Ile Leu Leu Pro Arg Ile Ser Pro Glu Glu Tyr Lys Ser Tyr Ser Pro
```

```
            865                 870                 875                 880
        Glu Ala Leu Trp Arg Tyr Leu Thr Ala Arg His Asp Trp Leu Asn Ile
                        885                 890                 895

Ile Leu Trp Ile Gly Glu Phe Gln Thr Gln His Ser Tyr Ala Ser Leu
                        900                 905                 910

Gln Gln Asn Lys Trp Pro Leu Leu Thr Val Asp Val Ile Asn Gln Asn
                        915                 920                 925

Thr Ser Cys Asn Asn Tyr Met Arg Asn Glu Ile Leu Asp Lys Leu Ala
                        930                 935                 940

Arg Asn Gly Val Phe Leu Ala Ser Glu Leu Glu Asp Phe Glu Cys Phe
        945                 950                 955                 960

Leu Leu Arg Leu Ser Arg Ile Gly Gly Val Ile Gln Asp Thr Leu Pro
                        965                 970                 975

Val Gln Asn Tyr Lys Thr Lys Glu Gly Trp Asp Phe His Ser Gln Phe
                        980                 985                 990

Ile Leu Tyr Cys Leu Glu His Ser Leu Gln His Leu Leu Tyr Val Tyr
                        995                1000                1005

Leu Asp Cys Tyr Lys Leu Ser Pro Glu Asn Cys Pro Phe Leu Glu
                1010                1015                1020

Lys Lys Glu Leu His Glu Ala His Pro Trp Phe Glu Phe Leu Val
                1025                1030                1035

Gln Cys Arg Gln Val Ala Ser Asn Leu Thr Asp Pro Lys Leu Ile
                1040                1045                1050

Phe Gln Ala Ser Leu Ala Asn Ala Gln Ile Leu Ile Pro Thr Asn
                1055                1060                1065

Gln Ala Ser Val Ser Ser Met Leu Leu Glu Gly His Thr Leu Leu
                1070                1075                1080

Ala Leu Ala Thr Thr Met Tyr Ser Pro Gly Gly Val Ser Gln Val
                1085                1090                1095

Val Gln Asn Glu Glu Asn Glu Asn Cys Leu Lys Lys Val Asp Pro
                1100                1105                1110

Gln Leu Leu Lys Met Ala Leu Thr Pro Tyr Pro Lys Leu Lys Thr
                1115                1120                1125

Ala Leu Phe Pro Gln Cys Thr Pro Pro Ser Val Leu Pro Ser Asp
                1130                1135                1140

Ile Thr Ile Tyr His Leu Ile Gln Ser Leu Ser Pro Phe Asp Pro
                1145                1150                1155

Ser Arg Leu Phe Gly Trp Gln Ser Ala Asn Thr Leu Ala Ile Gly
                1160                1165                1170

Asp Ala Trp Ser His Leu Pro His Phe Ser Ser Pro Asp Leu Val
                1175                1180                1185

Asn Lys Tyr Ala Ile Val Glu Arg Leu Asn Phe Ala Tyr Tyr Leu
                1190                1195                1200

His Asn Gly Arg Pro Ser Phe Ala Phe Gly Thr Phe Leu Val Gln
                1205                1210                1215

Glu Leu Ile Lys Ser Lys Thr Pro Lys Gln Leu Ile Gln Gln Val
                1220                1225                1230

Gly Asn Glu Ala Tyr Val Ile Gly Leu Ser Ser Phe His Ile Pro
                1235                1240                1245

Ser Ile Gly Ala Ala Cys Val Cys Phe Leu Glu Leu Leu Gly Leu
                1250                1255                1260

Asp Ser Leu Lys Leu Arg Val Asp Met Lys Val Ala Asn Ile Ile
                1265                1270                1275
```

```
Leu Ser Tyr Lys Cys Arg Asn Glu Asp Ala Gln Tyr Ser Phe Ile
    1280            1285                1290

Arg Glu Ser Val Ala Glu Lys Leu Ser Lys Leu Ala Asp Gly Glu
    1295            1300                1305

Lys Thr Thr Thr Glu Glu Leu Leu Val Leu Leu Glu Glu Gly Thr
    1310            1315                1320

Trp Asn Ser Ile Gln Gln Glu Ile Lys Arg Leu Ser Ser Glu
    1325            1330                1335

Ser Ser Ser Gln Trp Ala Leu Val Val Gln Phe Cys Arg Leu His
    1340            1345                1350

Asn Met Lys Leu Ser Ile Ser Tyr Leu Arg Glu Cys Ala Lys Ala
    1355            1360                1365

Asn Asp Trp Leu Gln Phe Ile Ile His Ser Gln Leu His Asn Tyr
    1370            1375                1380

His Pro Ala Glu Val Lys Ser Leu Ile Gln Tyr Phe Ser Pro Val
    1385            1390                1395

Ile Gln Asp His Leu Arg Leu Ala Phe Glu Asn Leu Pro Ser Val
    1400            1405                1410

Pro Thr Ser Lys Met Asp Ser Asp Gln Val Cys Asn Lys Cys Pro
    1415            1420                1425

Gln Glu Leu Gln Gly Ser Lys Gln Glu Met Thr Asp Leu Phe Glu
    1430            1435                1440

Ile Leu Leu Gln Cys Ser Glu Glu Pro Asp Ser Trp His Trp Leu
    1445            1450                1455

Leu Val Glu Ala Val Lys Gln Gln Ala Pro Ile Leu Ser Val Leu
    1460            1465                1470

Ala Ser Cys Leu Gln Gly Ala Ser Ala Ile Ser Cys Leu Cys Val
    1475            1480                1485

Trp Ile Ile Thr Ser Val Glu Asp Asn Val Ala Thr Glu Ala Met
    1490            1495                1500

Gly His Ile Gln Asp Ser Thr Glu Asp His Thr Trp Asn Leu Glu
    1505            1510                1515

Asp Leu Ser Val Ile Trp Arg Thr Leu Leu Thr Arg Gln Lys Ser
    1520            1525                1530

Lys Thr Leu Ile Arg Gly Phe Gln Leu Phe Phe Lys Asp Ser Pro
    1535            1540                1545

Leu Leu Leu Val Met Glu Met Tyr Glu Leu Cys Met Phe Phe Arg
    1550            1555                1560

Asn Tyr Lys Glu Ala Glu Ala Lys Leu Leu Glu Phe Gln Lys Ser
    1565            1570                1575

Leu Glu Thr Leu Asn Thr Ala Ala Thr Lys Val His Pro Val Ile
    1580            1585                1590

Pro Ala Met Trp Leu Glu Asp Gln Val Cys Phe Leu Leu Lys Leu
    1595            1600                1605

Met Leu Gln Gln Cys Lys Thr Gln Tyr Glu Leu Gly Lys Leu Leu
    1610            1615                1620

Gln Leu Phe Val Glu Arg Glu His Leu Phe Ser Asp Gly Pro Asp
    1625            1630                1635

Val Lys Lys Leu Cys Ile Leu Cys Gln Ile Leu Lys Asp Thr Ser
    1640            1645                1650

Ile Ala Ile Asn His Thr Ile Ile Thr Ser Tyr Ser Ile Glu Asn
    1655            1660                1665
```

```
Leu Gln His Glu Cys Arg Ser Ile Leu Glu Arg Leu Gln Thr Asp
1670                1675                1680

Gly Gln Phe Ala Leu Ala Arg Arg Val Ala Glu Leu Ala Glu Leu
1685                1690                1695

Pro Val Asp Asn Leu Val Ile Lys Glu Ile Thr Gln Glu Met Gln
1700                1705                1710

Thr Leu Lys His Ile Glu Gln Trp Ser Leu Lys Gln Ala Arg Ile
1715                1720                1725

Asp Phe Trp Lys Lys Cys His Glu Asn Phe Lys Lys Asn Ser Ile
1730                1735                1740

Ser Ser Lys Ala Ala Ser Ser Phe Phe Ser Thr Gln Ala His Val
1745                1750                1755

Ala Cys Glu His Pro Thr Gly Trp Ser Ser Met Glu Glu Arg His
1760                1765                1770

Leu Leu Leu Thr Leu Ala Gly His Trp Leu Ala Gln Glu Asp Val
1775                1780                1785

Val Pro Leu Asp Lys Leu Glu Glu Leu Glu Lys Gln Ile Trp Leu
1790                1795                1800

Cys Arg Ile Thr Gln His Thr Leu Gly Arg Asn Gln Glu Glu Thr
1805                1810                1815

Glu Pro Arg Phe Ser Arg Gln Ile Ser Thr Ser Gly Glu Leu Ser
1820                1825                1830

Phe Asp Ser Leu Ala Ser Glu Phe Ser Phe Ser Lys Leu Ala Ala
1835                1840                1845

Leu Asn Thr Ser Lys Tyr Leu Glu Leu Asn Ser Leu Pro Ser Lys
1850                1855                1860

Glu Thr Cys Glu Asn Arg Leu Asp Trp Lys Gln Glu Ser Leu
1865                1870                1875

Asn Phe Leu Ile Gly Arg Leu Leu Asp Asp Gly Cys Val His Glu
1880                1885                1890

Ala Ser Arg Val Cys Arg Tyr Phe His Phe Tyr Asn Pro Asp Val
1895                1900                1905

Ala Leu Val Leu His Cys Arg Ala Leu Ala Ser Gly Glu Ala Ser
1910                1915                1920

Met Glu Asp Leu His Pro Glu Ile His Ala Leu Leu Gln Ser Ala
1925                1930                1935

Glu Leu Leu Glu Glu Glu Ala Pro Asp Ile Pro Leu Arg Arg Val
1940                1945                1950

His Ser Thr Ser Ser Leu Asp Ser Gln Lys Phe Val Thr Val Pro
1955                1960                1965

Ser Ser Asn Glu Val Val Thr Asn Leu Glu Val Leu Thr Ser Lys
1970                1975                1980

Cys Leu His Gly Lys Asn Tyr Cys Arg Gln Val Leu Cys Leu Tyr
1985                1990                1995

Asp Leu Ala Lys Glu Leu Gly Cys Ser Tyr Thr Asp Val Ala Ala
2000                2005                2010

Gln Asp Gly Glu Ala Met Leu Arg Lys Ile Leu Ala Ser Gln Gln
2015                2020                2025

Pro Asp Arg Cys Lys Arg Ala Gln Ala Phe Ile Ser Thr Gln Gly
2030                2035                2040

Leu Lys Pro Asp Thr Val Ala Glu Leu Val Ala Glu Glu Val Thr
2045                2050                2055

Arg Glu Leu Leu Thr Ser Ser Gln Gly Thr Gly His Lys Gln Met
```

```
                    2060                2065                2070
Phe Asn Pro Thr Glu Glu Ser Gln Thr Phe Leu Gln Leu Thr Thr
            2075                2080                2085
Leu Cys Gln Asp Arg Thr Leu Val Gly Met Lys Leu Leu Asp Lys
            2090                2095                2100
Ile Ser Ser Val Pro His Gly Glu Leu Ser Cys Thr Thr Glu Leu
            2105                2110                2115
Leu Ile Leu Ala His His Cys Phe Thr Leu Thr Cys His Met Glu
            2120                2125                2130
Gly Ile Ile Arg Val Leu Gln Ala Ala His Met Leu Thr Asp Asn
            2135                2140                2145
His Leu Ala Pro Ser Glu Glu Tyr Gly Leu Val Val Arg Leu Leu
            2150                2155                2160
Thr Gly Ile Gly Arg Tyr Asn Glu Met Thr Tyr Ile Phe Asp Leu
            2165                2170                2175
Leu His Lys Lys His Tyr Phe Glu Val Leu Met Arg Lys Lys Leu
            2180                2185                2190
Asp Pro Ser Gly Thr Leu Lys Thr Ala Leu Leu Asp Tyr Ile Lys
            2195                2200                2205
Arg Cys Arg Pro Gly Asp Ser Glu Lys His Asn Met Ile Ala Leu
            2210                2215                2220
Cys Phe Ser Met Cys Arg Glu Ile Gly Glu Asn His Glu Ala Ala
            2225                2230                2235
Ala Arg Ile Gln Leu Lys Leu Ile Glu Ser Gln Pro Trp Glu Asp
            2240                2245                2250
Ser Leu Lys Asp Gly His Gln Leu Lys Gln Leu Leu Lys Ala
            2255                2260                2265
Leu Thr Leu Met Leu Asp Ala Ala Glu Ser Tyr Ala Lys Asp Ser
            2270                2275                2280
Cys Val Arg Gln Ala Gln His Cys Gln Arg Leu Thr Lys Leu Ile
            2285                2290                2295
Thr Leu Gln Ile His Phe Leu Asn Thr Gly Gln Asn Thr Met Leu
            2300                2305                2310
Ile Asn Leu Gly Arg His Lys Leu Met Asp Cys Ile Leu Ala Leu
            2315                2320                2325
Pro Arg Phe Tyr Gln Ala Ser Ile Val Ala Glu Ala Tyr Asp Phe
            2330                2335                2340
Val Pro Asp Trp Ala Glu Ile Leu Tyr Gln Gln Val Ile Leu Lys
            2345                2350                2355
Gly Asp Phe Asn Tyr Leu Glu Glu Phe Lys Gln Arg Leu Leu
            2360                2365                2370
Lys Ser Ser Ile Phe Glu Glu Ile Ser Lys Lys Tyr Lys Gln His
            2375                2380                2385
Gln Pro Thr Asp Met Val Met Glu Asn Leu Lys Lys Leu Leu Thr
            2390                2395                2400
Tyr Cys Glu Asp Val Tyr Leu Tyr Tyr Lys Leu Ala Tyr Glu His
            2405                2410                2415
Lys Phe Tyr Glu Ile Val Asn Val Leu Leu Lys Asp Pro Gln Thr
            2420                2425                2430
Gly Cys Cys Leu Lys Asp Met Leu Ala Gly
            2435                2440

<210> SEQ ID NO 7
```

<211> LENGTH: 1880
<212> TYPE: DNA
<213> ORGANISM: Homo sapiens

<400> SEQUENCE: 7

```
acggcttacc cgggctccga cagcggctgc aggtctccaa gttgcggccg ctggagcccg      60
agccatgcgg accgcggacc gggaggcgcg cccggggctt ccgtccctgc tgctgctgct     120
gctggccggg gccgggctgt cagccgcctc gcccccagca gcgccgcgct tcaacgtgag     180
cctggactcg gtccccgagc tgcgctggct gcccgtgctg cggcactacg acttggactt     240
ggtgcgcgcc gcgatggcgc aagtcatcgg ggacagagtc cccaagtggg tgcacgtgtt     300
aatcggaaaa gtggtcctgg agctggagcg cttcctgccc cagcccttca ccggcgagat     360
ccgcggcatg tgtgacttca tgaacctcag cctggcggac tgccttctgg tcaacctggc     420
ctacgagtcc tccgtgttct gcaccagtat tgtggctcaa gactccagag gccacattta     480
ccatggtcgg aatttggatt atccttttgg gaatgtctta cgcaagctga cagtggatgt     540
gcaattctta aagaatgggc agattgcatt cacaggaact acttttattg ctatgtagg      600
attatggact ggccagagcc acacaagtt tacagtttct ggtgatgaac gagataaagg     660
ctggtggtgg gagaatgcta tcgctgccct gtttcggaga cacattcccg tcagctggct     720
gatccgcgct accctgagtg agtcggaaaa cttcgaagca gctgttggca agttggccaa     780
gactccccctt attgctgatg tttattacat tgttggtggc acgtccccc gggagggggt     840
ggtcatcacg aggaacagag atggcccagc agacatttgg cctctagatc ctttgaatgg     900
agcgtggttc cgagttgaga caaattacga ccactggaag ccagcaccca aggaagatga     960
ccggagaaca tctgccatca aggcccttaa tgctacagga caagcaaacc tcagcctgga    1020
ggcacttttc cagattttgt cggtggttcc agttataac aacttcacaa tttatactac    1080
ggtaatgagc gccggtagcc cagacaagta catgactagg atcagaaacc cgagtagaaa    1140
gtaagtcagc agaagagcga gttcgcccgt gctgtgaaag atgattttt aaaaaatgaa    1200
attcttgaag agctgcacct taaaaaataa gacaaagtga aagtattgta ttatgttaca    1260
aacaatgcag gctccttcct catttaactt tacaaccttg cgaagtgggt ccaggagatt    1320
tggagtttgt ggtaaagcca gtaatgggca ttgtcctgca ttcccttccc ttcatggttt    1380
gcctcgatcc tctctaagct ctatcctgg cctgaataac tcaaagataa ttggtctcag    1440
agatcaagcc atatcctcag gccttatttc catcttctca tgattctgcc atcatacctt    1500
tgcttctccg ctaatgaaat gagctggcaa gacctctgtt cattgtgaag tgcttctgaa    1560
agagcctaag aaaaaaggct catctgaaag aaatggagaa ctctatttcg aaccaagcct    1620
gtttgaatgt gtgttagtct gatctttgat catgtgtttc catgtaatgg gagtctcgtt    1680
ttttataatg tttctaacgt tttattgaaa aacctatggc cctccttctt tctcaatagc    1740
tactttctta ctgctttttg aaaataatat gcaaccaaat tatttcttaa tgtcacataa    1800
ttaagtaata aaatgtcaaa agaaatgttg gcaaggagaa taaaaaaatt ccaagaaac    1860
ttaaaaaaaa aaaaaaaaaa                                              1880
```

<210> SEQ ID NO 8
<211> LENGTH: 359
<212> TYPE: PRT
<213> ORGANISM: Homo sapiens

<400> SEQUENCE: 8

Met Arg Thr Ala Asp Arg Glu Ala Arg Pro Gly Leu Pro Ser Leu Leu

```
            1               5                  10                 15
          Leu Leu Leu Leu Ala Gly Ala Gly Leu Ser Ala Ala Ser Pro Pro Ala
                          20                 25                 30
          Ala Pro Arg Phe Asn Val Ser Leu Asp Ser Val Pro Glu Leu Arg Trp
                      35                 40                 45
          Leu Pro Val Leu Arg His Tyr Asp Leu Asp Leu Val Arg Ala Ala Met
          50                  55                 60
          Ala Gln Val Ile Gly Asp Arg Val Pro Lys Trp Val His Val Leu Ile
          65                  70                 75                 80
          Gly Lys Val Val Leu Glu Leu Glu Arg Phe Leu Pro Gln Pro Phe Thr
                          85                 90                 95
          Gly Glu Ile Arg Gly Met Cys Asp Phe Met Asn Leu Ser Leu Ala Asp
                          100                105                110
          Cys Leu Leu Val Asn Leu Ala Tyr Glu Ser Ser Val Phe Cys Thr Ser
                          115                120                125
          Ile Val Ala Gln Asp Ser Arg Gly His Ile Tyr His Gly Arg Asn Leu
          130                 135                140
          Asp Tyr Pro Phe Gly Asn Val Leu Arg Lys Leu Thr Val Asp Val Gln
          145                 150                155                160
          Phe Leu Lys Asn Gly Gln Ile Ala Phe Thr Gly Thr Thr Phe Ile Gly
                          165                170                175
          Tyr Val Gly Leu Trp Thr Gly Gln Ser Pro His Lys Phe Thr Val Ser
                          180                185                190
          Gly Asp Glu Arg Asp Lys Gly Trp Trp Trp Glu Asn Ala Ile Ala Ala
                          195                200                205
          Leu Phe Arg Arg His Ile Pro Val Ser Trp Leu Ile Arg Ala Thr Leu
          210                 215                220
          Ser Glu Ser Glu Asn Phe Glu Ala Ala Val Gly Lys Leu Ala Lys Thr
          225                 230                235                240
          Pro Leu Ile Ala Asp Val Tyr Tyr Ile Val Gly Gly Thr Ser Pro Arg
                          245                250                255
          Glu Gly Val Val Ile Thr Arg Asn Arg Asp Gly Pro Ala Asp Ile Trp
                          260                265                270
          Pro Leu Asp Pro Leu Asn Gly Ala Trp Phe Arg Val Glu Thr Asn Tyr
                          275                280                285
          Asp His Trp Lys Pro Ala Pro Lys Glu Asp Asp Arg Arg Thr Ser Ala
                          290                295                300
          Ile Lys Ala Leu Asn Ala Thr Gly Gln Ala Asn Leu Ser Leu Glu Ala
          305                 310                315                320
          Leu Phe Gln Ile Leu Ser Val Val Pro Val Tyr Asn Asn Phe Thr Ile
                          325                330                335
          Tyr Thr Thr Val Met Ser Ala Gly Ser Pro Asp Lys Tyr Met Thr Arg
                          340                345                350
          Ile Arg Asn Pro Ser Arg Lys
                          355

<210> SEQ ID NO 9
<211> LENGTH: 1102
<212> TYPE: DNA
<213> ORGANISM: Homo sapiens

<400> SEQUENCE: 9
agcagtaccc cgtctcgctc ggttccgcgg cggccacgct ccgggagact tccggcaggg      60
cgggcgcggg gtcttggcga acggtcttcg gaagcggcgg cggcgcgatg accacgctac     120
```

```
gggcctttac ctgcgacgac ctgttccgct tcaacaacat taacttggat ccacttacag    180
aaacttatgg gattcctttc tacctacaat acctcgccca ctggccagag tatttcattg    240
ttgcagaggc acctggtgga gaattaatgg gttatattat gggtaaagca gaaggctcag    300
tagctaggga agaatggcac gggcacgtca cagctctgtc tgttgcccca gaatttcgac    360
gccttggttt ggctgctaaa cttatggagt tactagagga gatttcagaa agaaagggtg    420 gatttttgt ggatctcttt gtaagagtat ctaaccaagt tgcagttaac atgtacaagc     480
agttgggcta cagtgtatat aggacggtca tagagtacta ttcggccagc aacggggagc    540
ctgatgagga cgcttatgat atgaggaaag cactttccag ggatactgag aagaaatcca    600
tcataccatt acctcatcct gtgaggcctg aagacattga ataaccctgg cagtggttc     660 ttaggcagat actctagatg ctttatggac aatattattt tcattggatg attctggagc    720
tctattagga gaaagtaat cattttaggt cttaaagact tcaagaaaat acaggttatc     780
aatttatttt aaatctcatt gtttccagtt agcaatatca tacctattaa agctgttcat    840
tgtaacaaaa ttcaatcaaa aaggcagcta ggtcagaagg aaacatacca ctctcatggt    900
tcatagtatt cactgtatgt atgctaggga aaagacttgc tccagtctcc tcctcagttc    960
tgtgcctgag aaccactgct gcatatattt gttttaaat tttgtattga actgttaatt     1020
gaagctttaa aagcatatat gaaatgtata aatctaagat gtataataca ttattgactc    1080
tatgaaaaaa aaaaaaaaaa aa                                             1102
```

<210> SEQ ID NO 10
<211> LENGTH: 178
<212> TYPE: PRT
<213> ORGANISM: Homo sapiens

<400> SEQUENCE: 10

```
Met Thr Thr Leu Arg Ala Phe Thr Cys Asp Asp Leu Phe Arg Phe Asn
 1               5                  10                  15

Asn Ile Asn Leu Asp Pro Leu Thr Glu Thr Tyr Gly Ile Pro Phe Tyr
                20                  25                  30

Leu Gln Tyr Leu Ala His Trp Pro Glu Tyr Phe Ile Val Ala Glu Ala
            35                  40                  45

Pro Gly Gly Glu Leu Met Gly Tyr Ile Met Gly Lys Ala Glu Gly Ser
        50                  55                  60

Val Ala Arg Glu Glu Trp His Gly His Val Thr Ala Leu Ser Val Ala
65                  70                  75                  80

Pro Glu Phe Arg Arg Leu Gly Leu Ala Ala Lys Leu Met Glu Leu Leu
                85                  90                  95

Glu Glu Ile Ser Glu Arg Lys Gly Gly Phe Phe Val Asp Leu Phe Val
            100                 105                 110

Arg Val Ser Asn Gln Val Ala Val Asn Met Tyr Lys Gln Leu Gly Tyr
        115                 120                 125

Ser Val Tyr Arg Thr Val Ile Glu Tyr Tyr Ser Ala Ser Asn Gly Glu
    130                 135                 140

Pro Asp Glu Asp Ala Tyr Asp Met Arg Lys Ala Leu Ser Arg Asp Thr
145                 150                 155                 160

Glu Lys Lys Ser Ile Ile Pro Leu Pro His Pro Val Arg Pro Glu Asp
                165                 170                 175

Ile Glu
```

```
<210> SEQ ID NO 11
<211> LENGTH: 397
<212> TYPE: DNA
<213> ORGANISM: Homo sapiens

<400> SEQUENCE: 11
aggagctggc cctgaacgag ctggtgacgc tgacgtgcct ggcacgcggc ttcagcccca      60
aggatgtgct ggttcgctgg ctgcaggggt cacaggagct gccccgcgag aagtacctga     120
cttgggcatc ccggcaggag cccagccagg gcaccaccac cttcgctgtg accagcatac     180
tgcgcgtggc agccgaggac tggaagaagg gggacacctt ctcctgcatg gtgggccacg     240
aggccctgcc gctggccttc acacagaaga ccatcgaccg cttggcgggt aaacccaccc     300
atgtcaatgt gtctgttgtc atggcggagg tggacggcac ctgctactga gccgcccgcc     360
tgtccccacc cctgaataaa ctccatgctc ccccaag                              397

<210> SEQ ID NO 12
<211> LENGTH: 115
<212> TYPE: PRT
<213> ORGANISM: Homo sapiens

<400> SEQUENCE: 12

Glu Leu Ala Leu Asn Glu Leu Val Thr Leu Thr Cys Leu Ala Arg Gly
1               5                   10                  15

Phe Ser Pro Lys Asp Val Leu Val Arg Trp Leu Gln Gly Ser Gln Glu
            20                  25                  30

Leu Pro Arg Glu Lys Tyr Leu Thr Trp Ala Ser Arg Gln Glu Pro Ser
        35                  40                  45

Gln Gly Thr Thr Thr Phe Ala Val Thr Ser Ile Leu Arg Val Ala Ala
    50                  55                  60

Glu Asp Trp Lys Lys Gly Asp Thr Phe Ser Cys Met Val Gly His Glu
65                  70                  75                  80

Ala Leu Pro Leu Ala Phe Thr Gln Lys Thr Ile Asp Arg Leu Ala Gly
                85                  90                  95

Lys Pro Thr His Val Asn Val Ser Val Val Met Ala Glu Val Asp Gly
            100                 105                 110

Thr Cys Tyr
        115

<210> SEQ ID NO 13
<211> LENGTH: 433
<212> TYPE: DNA
<213> ORGANISM: Homo sapiens

<400> SEQUENCE: 13
tacaccctgc cccatcccg ggatgagctg accaagaacc aggtcagcct gacctgcctg       60
gtcaaaggct tctatcccag cgacatcgcc gtggagtggg agagcaatgg gcagccggag     120
aacaactaca agaccacgcc tcccgtgctg gactccgacg gctccttctt cctctacagc     180
aagctcaccg tggacaagag caggtggcag caggggaacg tcttctcatg ctccgtgatg     240
catgaggctc tgcacaacca ctacacacag aagagcctct ccctgtctcc gggtaaatga     300
gtgccacggc cggcaagccc ccgctcccca ggctctcggg gtcgcgcgag gatgcttggc     360
acgtaccccg tgtacatact tcccaggcac ccagcatgga aataaagcac ccagcgcttc     420
cctgggcccc tgc                                                        433

<210> SEQ ID NO 14
```

<211> LENGTH: 99
<212> TYPE: PRT
<213> ORGANISM: Homo sapiens

<400> SEQUENCE: 14

```
Tyr Thr Leu Pro Pro Ser Arg Asp Glu Leu Thr Lys Asn Gln Val Ser
1               5                   10                  15

Leu Thr Cys Leu Val Lys Gly Phe Tyr Pro Ser Asp Ile Ala Val Glu
            20                  25                  30

Trp Glu Ser Asn Gly Gln Pro Glu Asn Asn Tyr Lys Thr Thr Pro Pro
        35                  40                  45

Val Leu Asp Ser Asp Gly Ser Phe Phe Leu Tyr Ser Lys Leu Thr Val
    50                  55                  60

Asp Lys Ser Arg Trp Gln Gln Gly Asn Val Phe Ser Cys Ser Val Met
65                  70                  75                  80

His Glu Ala Leu His Asn His Tyr Thr Gln Lys Ser Leu Ser Leu Ser
                85                  90                  95

Pro Gly Lys
```

<210> SEQ ID NO 15
<211> LENGTH: 1413
<212> TYPE: DNA
<213> ORGANISM: Homo sapiens

<400> SEQUENCE: 15

| | | | | | |
|---|---|---|---|---|---|
| ttgtgattgt | ttttagtttg | ttagctgcct | ggagtgttat | tttaagaaag | cagaagcacc | 60 |
| atcatttgca | cactccttat | agatcacaca | ccttaaccct | gacttttttt | gctccagttt | 120 |
| ttcagaagaa | gtgaagtcaa | gatgaagaac | catttgcttt | tctggggagt | cctggcggtt | 180 |
| tttattaagg | ctgttcatgt | gaaagcccaa | aagatgaaa | ggattgttct | tgttgacaac | 240 |
| aaatgtaagt | gtgcccggat | tacttccagg | atcatccgtt | cttccgaaga | tcctaatgag | 300 |
| gacattgtgg | agagaaacat | ccgaattatt | gttcctctga | caacaggga | gaatatctct | 360 |
| gatcccacct | caccattgag | aaccagattt | gtgtaccatt | tgtctgacct | ctgtaaaaaa | 420 |
| tgtgatccta | cagaagtgga | gctggataat | cagatagtta | ctgctaccca | gagcaatatc | 480 |
| tgtgatgaag | acagtgctac | agagacctgc | tacacttatg | acagaaacaa | gtgctacaca | 540 |
| gctgtggtcc | cactcgtata | tggtggtgag | accaaaatgg | tggaaacagc | cttaaccca | 600 |
| gatgcctgct | atcctgacta | atttaagtca | ttgctgactg | catagctctt | tttcttgaga | 660 |
| ggctctccat | tttgattcag | aaagttagca | tatttattac | caatgaattt | gaaaccaggg | 720 |
| cttttttttt | tttttgggtg | atgtaaaacc | aactccctgc | caccaaaata | attaaaatag | 780 |
| tcacattgtt | atctttatta | ggtaatcact | tcttaattat | atgttcatac | tctaagtatc | 840 |
| aaaatcttcc | aattatcatg | ctcacctgaa | agaggtatgc | tctcttagga | atacagtttc | 900 |
| tagcattaaa | caaataaaca | aggggagaaa | ataaaactca | aggactgaaa | tcaggaggt | 960 |
| gtaataaaat | gttcctcgca | ttccccccg | cttttttttt | tttttttgac | tttgccttgg | 1020 |
| agagccagag | cttccgcatt | ttctttacta | ttcttttaa | aaaagtttc | actgtgtaga | 1080 |
| gaacatatat | gcataaacat | aggtcaatta | tatgtctcca | ttagaaaat | aataattgga | 1140 |
| aaacatgttc | tagaactagt | tacaaaaata | atttaaggtg | aaatctctaa | tatttataaa | 1200 |
| agtagcaaaa | taaatgcata | attaaaatat | atttggacat | aacagacttg | gaagcagatg | 1260 |
| atacagactt | ctttttttca | taatcaggtt | agtgtaagaa | attgccattt | gaaacaatcc | 1320 |
| attttgtaac | tgaaccttat | gaaatatatg | tatttcatgg | tacgtattct | ctagcacagt | 1380 |

```
ctgagcaatt aaatagattc ataagcataa aaa                                   1413
```

<210> SEQ ID NO 16
<211> LENGTH: 159
<212> TYPE: PRT
<213> ORGANISM: Homo sapiens

<400> SEQUENCE: 16

| | | | | | | | | | | | | | | | |
|---|---|---|---|---|---|---|---|---|---|---|---|---|---|---|---|
| Met | Lys | Asn | His | Leu | Leu | Phe | Trp | Gly | Val | Leu | Ala | Val | Phe | Ile | Lys |
| 1 | | | | 5 | | | | | 10 | | | | | 15 | |
| Ala | Val | His | Val | Lys | Ala | Gln | Glu | Asp | Glu | Arg | Ile | Val | Leu | Val | Asp |
| | | | 20 | | | | | 25 | | | | | 30 | | |
| Asn | Lys | Cys | Lys | Cys | Ala | Arg | Ile | Thr | Ser | Arg | Ile | Ile | Arg | Ser | Ser |
| | | | 35 | | | | | 40 | | | | | 45 | | |
| Glu | Asp | Pro | Asn | Glu | Asp | Ile | Val | Glu | Arg | Asn | Ile | Arg | Ile | Ile | Val |
| | | | 50 | | | | | 55 | | | | | 60 | | |
| Pro | Leu | Asn | Asn | Arg | Glu | Asn | Ile | Ser | Asp | Pro | Thr | Ser | Pro | Leu | Arg |
| 65 | | | | | 70 | | | | | 75 | | | | | 80 |
| Thr | Arg | Phe | Val | Tyr | His | Leu | Ser | Asp | Leu | Cys | Lys | Lys | Cys | Asp | Pro |
| | | | | 85 | | | | | 90 | | | | | 95 | |
| Thr | Glu | Val | Glu | Leu | Asp | Asn | Gln | Ile | Val | Thr | Ala | Thr | Gln | Ser | Asn |
| | | | 100 | | | | | 105 | | | | | 110 | | |
| Ile | Cys | Asp | Glu | Asp | Ser | Ala | Thr | Glu | Thr | Cys | Tyr | Thr | Tyr | Asp | Arg |
| | | | 115 | | | | | 120 | | | | | 125 | | |
| Asn | Lys | Cys | Tyr | Thr | Ala | Val | Val | Pro | Leu | Val | Tyr | Gly | Gly | Glu | Thr |
| | | | 130 | | | | | 135 | | | | | 140 | | |
| Lys | Met | Val | Glu | Thr | Ala | Leu | Thr | Pro | Asp | Ala | Cys | Tyr | Pro | Asp | |
| 145 | | | | | 150 | | | | | 155 | | | | | |

<210> SEQ ID NO 17
<211> LENGTH: 1209
<212> TYPE: DNA
<213> ORGANISM: Homo sapiens

<400> SEQUENCE: 17

```
ttctaaactc tgagggggtc ggatgacgtg gccattcttt gcctaaagca ttgagtttac     60
tgcaaggtca gaaagcatg caaagccctc agaatggctg caaagagctc caacaaaaca    120
atttagaact ttattaagga atagggggaa gctaggaaga aactcaaaac atcaagattt    180
taaatacgct tcttggtctc cttgctataa ttatctggga taagcatgct gttttctgtc    240
tgtccctaac atgccctgtg attatccgca acaacacac ccaagggcag aactttgtta    300
cttaaacacc atcctgtttg cttctttcct caggaactgt ggctgcacca tctgtcttca    360
tcttcccgcc atctgatgag cagttgaaat ctggaactgc ctctgttgtg tgcctgctga    420
ataacttcta tcccagagag gccaaagtac agtggaaggt ggataacgcc ctccaatcgg    480
gtaactccca ggagagtgtc acagagcagg acagcacctac agcctcagca    540
gcaccctgac gctgagcaaa gcagactacg agaaacacaa agtctacgcc tgcgaagtca    600
cccatcaggg cctgagctcg cccgtcacaa agagcttcaa caggggagag tgttagaggg    660
agaagtgccc ccacctgctc ctcagttcca gcctgacccc ctccatcct ttggcctctg    720
acccttttc cacaggggac ctaccctat tgcggtcctc cagctcatct ttcacctcac    780
ccccctcctc ctccttggct ttaattatgc taatgttgga gggagaatgaa taaataaagt    840
gaatctttgc acctgtggtt tctctctttc ctcaatttaa taattattat ctgttgttta    900
```

```
ccaactactc aatttctctt ataagggact aaatatgtag tcatcctaag gcgcataacc    960
atttataaaa atcatccttc attctatttt accctatcat cctctgcaag acagtcctcc   1020
ctcaaaccca caagccttct gtcctcacag tccctgggc cgtggtagga gagacttgct   1080
tccttgtttt cccctcctca gcaagccctc atagtccttt ttaagggtga caggtcttac   1140
ggtcatatat cctttgattc aattccctgg gaatcaacca aggcaaattt ttcaaaagaa   1200
gaaacctgc                                                          1209
```

<210> SEQ ID NO 18
<211> LENGTH: 106
<212> TYPE: PRT
<213> ORGANISM: Homo sapiens

<400> SEQUENCE: 18

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 19
<211> LENGTH: 391
<212> TYPE: DNA
<213> ORGANISM: Homo sapiens

<400> SEQUENCE: 19

```
gagccccctg cccctcatcc accccgcagg tcagcccaag gctgcccct cggtcactct     60
gttcccgccc tcctctgagg agcttcaagc caacaaggcc acactggtgt gtctcataag    120
tgacttctac ccgggagccg tgacagtggc ttggaaagca gatagcagcc ccgtcaaggc    180
gggagtggag accaccacac cctccaaaca aagcaacaac aagtacgcgg ccagcagcta    240
tctgagcctg acgcctgagc agtggaagtc cacagaagc tacagctgcc aggtcacgca    300
tgaagggagc accgtggaga agacagtggc ccctacagaa tgttcatagg ttctcaaccc    360
tcaccccac cacgggagac tagagctgca g                                    391
```

<210> SEQ ID NO 20
<211> LENGTH: 105
<212> TYPE: PRT
<213> ORGANISM: Homo sapiens

<400> SEQUENCE: 20

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45
```

```
Lys Ala Gly Val Glu Thr Thr Thr Pro Ser Lys Gln Ser Asn Asn Lys
     50                   55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
            100                 105
```

<210> SEQ ID NO 21
<211> LENGTH: 650
<212> TYPE: DNA
<213> ORGANISM: Homo sapiens

<400> SEQUENCE: 21

```
cacctgaact cctgggggga ccgtcagtct tcctcttccc cccaaaaccc aaggacaccc      60
tcatgatctc ccggacccct gaggtcacat gcgtggtggt ggacgtgagc cacgaagacc    120
ctgaggtcaa gttcaactgg tacgtggacg gcgtggaggt gcataatgcc aagacaaagc    180
cgcgggagga gcagtacaac agcacgtacc gtgtggtcag cgtcctcacc gtcctgcacc    240
aggactggct gaatggcaag gagtacaagt gcaaggtctc caacaaagcc ctcccagccc    300
ccatcgagaa aaccatctcc aaagccaaag ggcagcccg agaaccacag gtgtacaccc     360
tgcccccatc ccgggatgag ctgaccaaga accaggtcag cctgacctgc ctggtcaaag    420
gcttctatcc cagcgacatc gccgtggagt gggagagcaa tgggcagccg gagaacaact    480
acaagaccac gcctcccgtg ctggactccg acggctcctt cttcctctac agcaagctca    540
ccgtggacaa gagcaggtgg cagcagggga acgtcttctc atgctccgtg atgcatgagg    600
ctctgcacaa ccactacaca cagaagagcc tctccctgtc tccgggtaaa                650
```

<210> SEQ ID NO 22
<211> LENGTH: 216
<212> TYPE: PRT
<213> ORGANISM: Homo sapiens

<400> SEQUENCE: 22

```
Pro Glu Leu Leu Gly Gly Pro Ser Val Phe Leu Phe Pro Pro Lys Pro
 1               5                  10                  15

Lys Asp Thr Leu Met Ile Ser Arg Thr Pro Glu Val Thr Cys Val Val
             20                  25                  30

Val Asp Val Ser His Glu Asp Pro Glu Val Lys Phe Asn Trp Tyr Val
         35                  40                  45

Asp Gly Val Glu Val His Asn Ala Lys Thr Lys Pro Arg Glu Glu Gln
     50                  55                  60

Tyr Asn Ser Thr Tyr Arg Val Val Ser Val Leu Thr Val Leu His Gln
 65                  70                  75                  80

Asp Trp Leu Asn Gly Lys Glu Tyr Lys Cys Lys Val Ser Asn Lys Ala
                 85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
```

```
                145                 150                 155                 160
Lys Thr Thr Pro Pro Val Leu Asp Ser Asp Gly Ser Phe Phe Leu Tyr
                    165                 170                 175

Ser Lys Leu Thr Val Asp Lys Ser Arg Trp Gln Gln Gly Asn Val Phe
                180                 185                 190

Ser Cys Ser Val Met His Glu Ala Leu His Asn His Tyr Thr Gln Lys
            195                 200                 205

Ser Leu Ser Leu Ser Pro Gly Lys
    210                 215

<210> SEQ ID NO 23
<211> LENGTH: 3231
<212> TYPE: DNA
<213> ORGANISM: Homo sapiens

<400> SEQUENCE: 23
```

| | | | | | |
|---|---|---|---|---|---|
| ccggaggccg | cggcgagagc | gcgcccagcc | ccgccgcgat | gcccgcgcgc | ccaggacgcc | 60 |
| tcctcccgct | gctggcccgg | ccggcggccc | tgactgcgct | gctgctgctg | ctgctgggcc | 120 |
| atggcggcgg | cgggcgctgg | ggcgcccggg | cccaggaggc | ggcggcggcg | gcggcggacg | 180 |
| ggccccccgc | ggcagacggc | gaggacggac | aggacccgca | cagcaagcac | ctgtacacgg | 240 |
| ccgacatgtt | cacgcacggg | atccagagcg | ccgcgcactt | cgtcatgttc | ttcgcgccct | 300 |
| ggtgtggaca | ctgccagcgg | ctgcagccga | cttggaatga | cctgggagac | aaatacaaca | 360 |
| gcatggaaga | tgccaaagtc | tatgtggcta | aagtggactg | cacggcccac | tccgacgtgt | 420 |
| gctccgccca | gggggtgcga | ggataccccc | ccttaaagct | tttcaagcca | ggccaagaag | 480 |
| ctgtgaagta | ccagggtcct | cgggacttcc | agacactgga | aaactggatg | ctgcagacac | 540 |
| tgaacgagga | gccagtgaca | ccagagccgg | aagtggaacc | gcccagtgcc | ccgagctca | 600 |
| agcaagggct | gtatgagctc | tcagcaagca | actttgagct | gcacgttgca | caaggcgacc | 660 |
| actttatcaa | gttcttcgct | ccgtggtgtg | gtcactgcaa | agcctggct | ccaacctggg | 720 |
| agcagctggc | tctgggcctt | gaacattccg | aaactgtcaa | gattggcaag | gttgattgta | 780 |
| cacagcacta | tgaactctgc | tccggaaacc | aggttcgtgg | ctatcccact | cttctctggt | 840 |
| tccgagatgg | aaaaaggtg | gatcagtaca | agggaaagcg | ggatttggag | tcactgaggg | 900 |
| agtacgtgga | gtcgcagctg | cagcgcacag | agactggagc | gacggagacc | gtcacgccct | 960 |
| cagaggcccc | ggtgctggca | gctgagcccg | aggctgacaa | gggcactgtg | ttggcactca | 1020 |
| ctgaaaataa | cttcgatgac | accattgcag | aaggaataac | cttcatcaag | ttttatgctc | 1080 |
| catggtgtgg | tcattgtaag | actctggctc | ctacttggga | ggaactctct | aaaaaggaat | 1140 |
| tccctggtct | ggcgggggtc | aagatcgccg | aagtagactg | cactgctgaa | cggaatatct | 1200 |
| gcagcaagta | ttcggtacga | ggctacccca | cgttattgct | tttccgagga | gggaagaaag | 1260 |
| tcagtgagca | cagtggaggc | agagaccttg | actcgttaca | ccgctttgtc | ctgagccaag | 1320 |
| cgaaagacga | actttaggaa | cacagttgga | ggtcacctct | cctgcccagc | tcccgcaccc | 1380 |
| tgcgtttagg | agttcagtcc | cacagaggcc | actgggttcc | cagtggtggc | tgttcagaaa | 1440 |
| gcagaacata | ctaagcgtga | ggtatcttct | ttgtgtgtgt | gttttccaag | ccaacacact | 1500 |
| ctacagattc | tttattaagt | taagtttctc | taagtaaatg | tgtaactcat | ggtcactgtg | 1560 |
| taaacatttt | cagtggcgat | atatccccctt | tgaccttctc | ttgatgaaat | ttacatggtt | 1620 |
| tcctttgaga | ctaaaatagc | gttgagggaa | atgaaattgc | tggactattt | gtggctcctg | 1680 |
| agttgagtga | ttttggtgaa | agaaagcaca | tccaaagcat | agtttacctg | cccacgagtt | 1740 |

| | |
|---|---|
| ctggaaaggt ggccttgtgg cagtattgac gttcctctga tcttaaggtc acagttgact | 1800 |
| caatactgtg ttggtccgta gcatggagca gattgaaatg caaaaaccca cacctctgga | 1860 |
| agataccttc acggccgctg ctggagcttc tgttgctgtg aatacttctc tcagtgtgag | 1920 |
| aggttagccg tgatgaaagc agcgttactt ctgaccgtgc ctgagtaaga gaatgctgat | 1980 |
| gccataactt tatgtgtcga tacttgtcaa atcagttact gttcagggga tccttctgtt | 2040 |
| tctcacgggg tgaaacatgt ctttagttcc tcatgttaac acgaagccag agcccacatg | 2100 |
| aactgttgga tgtcttcctt agaaagggta ggcatggaaa attccacgag gctcattctc | 2160 |
| agtatctcat taactcattg aaagattcca gttgtatttg tcacctgggg tgacaagacc | 2220 |
| agacaggctt tcccaggcct gggtatccag ggaggctctg cagccctgct gaagggccct | 2280 |
| aactagagtt ctagagtttc tgattctgtt tctcagtagt ccttttagag gcttgctata | 2340 |
| cttggtctgc ttcaaggagg tcgaccttct aatgtatgaa gaatgggatg catttgatct | 2400 |
| caagaccaaa gacagatgtc agtgggctgc tctggccctg gtgtgcacgg ctgtggcagc | 2460 |
| tgttgatgcc agtgtcctct aactcatgct gtccttgtga ttaaacacct ctatctccct | 2520 |
| tgggaataag cacatacagg cttaagctct aagatagata ggtgtttgtc cttttaccat | 2580 |
| cgagctactt cccataataa ccactttgca tccaacactc ttcacccacc tcccatacgc | 2640 |
| aaggggatgt ggatacttgg cccaaagtaa ctggtggtag gaatcttaga aacaagacca | 2700 |
| cttatactgt ctgtctgagg cagaagataa cagcagcatc tcgaccagcc tctgccttaa | 2760 |
| aggaaatctt tattaatcac gtatggttca cagataattc ttttttttaaa aaaacccaac | 2820 |
| ctcctagaga agcacaactg tcaagagtct tgtacacaca acttcagctt tgcatcacga | 2880 |
| gtcttgtatt ccaagaaaat caagtggta caatttgttt gtttacacta tgatactttc | 2940 |
| taaataaact cttttttttt aaaagtctgg tctttccttc aatgttacag caaaacagat | 3000 |
| ataaaataga caataaatta tagtttatat ttacaaaaaa agctgtaagt gcaaacagtt | 3060 |
| gtagattata aatgtattat ttaatcagtt tagtatgaaa ttgccttccc agtacatgat | 3120 |
| tgtgaaaaag acatttagaa aatattctaa aatttaatct gagcctcact ttctacaagg | 3180 |
| gaaatcatga tttccgttca taaacagcat gctcatcccc ctaacaccat t | 3231 |

<210> SEQ ID NO 24
<211> LENGTH: 432
<212> TYPE: PRT
<213> ORGANISM: Homo sapiens

<400> SEQUENCE: 24

Met Pro Ala Arg Pro Gly Arg Leu Leu Pro Leu Leu Ala Arg Pro Ala
1               5                   10                  15

Ala Leu Thr Ala Leu Leu Leu Leu Leu Gly His Gly Gly Gly Gly
            20                  25                  30

Arg Trp Gly Ala Arg Ala Gln Glu Ala Ala Ala Ala Ala Asp Gly
        35                  40                  45

Pro Pro Ala Ala Asp Gly Glu Asp Gly Gln Asp Pro His Ser Lys His
    50                  55                  60

Leu Tyr Thr Ala Asp Met Phe Thr His Gly Ile Gln Ser Ala Ala His
65                  70                  75                  80

Phe Val Met Phe Phe Ala Pro Trp Cys Gly His Cys Gln Arg Leu Gln
                85                  90                  95

Pro Thr Trp Asn Asp Leu Gly Asp Lys Tyr Asn Ser Met Glu Asp Ala
            100                 105                 110

```
Lys Val Tyr Val Ala Lys Val Asp Cys Thr Ala His Ser Asp Val Cys
                115                 120                 125

Ser Ala Gln Gly Val Arg Gly Tyr Pro Thr Leu Lys Leu Phe Lys Pro
        130                 135                 140

Gly Gln Glu Ala Val Lys Tyr Gln Gly Pro Arg Asp Phe Gln Thr Leu
145                 150                 155                 160

Glu Asn Trp Met Leu Gln Thr Leu Asn Glu Glu Pro Val Thr Pro Glu
                165                 170                 175

Pro Glu Val Glu Pro Pro Ser Ala Pro Glu Leu Lys Gln Gly Leu Tyr
            180                 185                 190

Glu Leu Ser Ala Ser Asn Phe Glu Leu His Val Ala Gln Gly Asp His
        195                 200                 205

Phe Ile Lys Phe Phe Ala Pro Trp Cys Gly His Cys Lys Ala Leu Ala
    210                 215                 220

Pro Thr Trp Glu Gln Leu Ala Leu Gly Leu Glu His Ser Glu Thr Val
225                 230                 235                 240

Lys Ile Gly Lys Val Asp Cys Thr Gln His Tyr Glu Leu Cys Ser Gly
                245                 250                 255

Asn Gln Val Arg Gly Tyr Pro Thr Leu Leu Trp Phe Arg Asp Gly Lys
            260                 265                 270

Lys Val Asp Gln Tyr Lys Gly Lys Arg Asp Leu Glu Ser Leu Arg Glu
        275                 280                 285

Tyr Val Glu Ser Gln Leu Gln Arg Thr Glu Thr Gly Ala Thr Glu Thr
    290                 295                 300

Val Thr Pro Ser Glu Ala Pro Val Leu Ala Ala Glu Pro Glu Ala Asp
305                 310                 315                 320

Lys Gly Thr Val Leu Ala Leu Thr Glu Asn Asn Phe Asp Asp Thr Ile
                325                 330                 335

Ala Glu Gly Ile Thr Phe Ile Lys Phe Tyr Ala Pro Trp Cys Gly His
            340                 345                 350

Cys Lys Thr Leu Ala Pro Thr Trp Glu Glu Leu Ser Lys Lys Glu Phe
        355                 360                 365

Pro Gly Leu Ala Gly Val Lys Ile Ala Glu Val Asp Cys Thr Ala Glu
    370                 375                 380

Arg Asn Ile Cys Ser Lys Tyr Ser Val Arg Gly Tyr Pro Thr Leu Leu
385                 390                 395                 400

Leu Phe Arg Gly Gly Lys Lys Val Ser Glu His Ser Gly Gly Arg Asp
                405                 410                 415

Leu Asp Ser Leu His Arg Phe Val Leu Ser Gln Ala Lys Asp Glu Leu
            420                 425                 430

<210> SEQ ID NO 25
<211> LENGTH: 480
<212> TYPE: DNA
<213> ORGANISM: Homo sapiens

<400> SEQUENCE: 25
ccagcccggg agcagctgaa cctgcgggag tcggccacca tcacgtgcct ggtgacgggc      60
ttctctcccg cggacgtctt cgtgcagtgg atgcagaggg ggcagccctt gtccccggag     120
aagtatgtga ccagcgcccc aatgcctgag ccccaggccc caggccggta cttcgcccac     180
agcatcctga ccgtgtccga agaggaatgg aacacggggg agacctacac ctgcgtggtg     240
gcccatgagg ccctgcccaa cagggtcacc gagaggaccg tggacaagtc caccggtaaa     300
```

```
cccaccctgt acaacgtgtc cctggtcatg tccgacacag ctggcacctg ctactgaccc    360
tgctggcctg cccacaggct cggggcggct ggccgctctg tgtgtgcatg caaactaacc    420
gtgtcaacgg ggtgagatgt tgcatcttat aaaattagaa ataaaaagat ccattcaaaa    480
```

<210> SEQ ID NO 26
<211> LENGTH: 1408
<212> TYPE: DNA
<213> ORGANISM: Homo sapiens

<400> SEQUENCE: 26

```
aaacagaagg ggaggtgcag tttcagaacc cagccagcct ctctcttgct gcctagcctc     60
ctgccggcct catcttcgcc cagccaaccc cgcctggagc cctatggcca actgcgagtt    120
cagcccggtg tccggggaca aaccctgctg ccggctctct aggagagccc aactctgtct    180
tggcgtcagt atcctggtcc tgatcctcgt cgtggtgctc gcggtggtcg tcccgaggtg    240
gcgccagcag tggagcggtc cgggcaccac caagcgcttt cccgagaccg tcctggcgcg    300
atgcgtcaag tacactgaaa ttcatcctga gatgagacat gtagactgcc aaagtgtatg    360
ggatgctttc aagggtgcat ttatttcaaa acatccttgc aacattactg aagaagacta    420
tcagccacta atgaagttgg gaactcagac cgtaccttgc aacaagattc ttctttggag    480
cagaataaaa gatctggccc atcagttcac acaggtccag cgggacatgt tcaccctgga    540
ggacacgctg ctaggctacc ttgctgatga cctcacatgg tgtggtgaat caacacttc     600 caaaataaac tatcaatctt gcccagactg agaaaggac tgcagcaaca accctgtttc     660
agtattctgg aaacggtttt cccgcaggtt tgcagaagct gcctgtgatg tggtccatgt    720
gatgctcaat ggatcccgca gtaaaatctt tgacaaaaac agcacttttg ggagtgtgga    780
agtccataat ttgcaaccag agaaggttca gacactagag gctgggtga tacatggtgg     840 aagagaagat tccagagact tatgccagga tcccaccata aaagagctgg aatcgattat    900
aagcaaaagg aatattcaat ttcctgcaa gaatatctac agacctgaca gtttcttca     960 gtgtgtgaaa atcctgagg attcatcttg cacatctgag atctgagcca gtcgctgtgg   1020
ttgttttagc tccttgactc cttgtggttt atgtcatcat acatgactca gcatacctgc   1080
tggtgcagag ctgaagattt tggagggtcc tccacaataa ggtcaatgcc agagacggaa   1140 gccttttttcc ccaaagtctt aaaataactt atatcatcag catacctta ttgtgatcta   1200 tcaatagtca agaaaaatta ttgtataaga ttagaatgaa aattgtatgt taagttactt   1260
cactttaatt ctcatgtgat cctttttatgt tatttatata ttggtaacat cctttctatt   1320
gaaaaatcac cacaccaaac ctctcttatt agaacaggca agtgaagaaa agtgaatgct   1380
caagtttttc agaaagcatt acatttcc                                      1408
```

<210> SEQ ID NO 27
<211> LENGTH: 300
<212> TYPE: PRT
<213> ORGANISM: Homo sapiens

<400> SEQUENCE: 27

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45
```

```
Gln Trp Ser Gly Pro Gly Thr Thr Lys Arg Phe Pro Glu Thr Val Leu
 50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                 85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
290                 295                 300

<210> SEQ ID NO 28
<211> LENGTH: 3802
<212> TYPE: DNA
<213> ORGANISM: Homo sapiens
<220> FEATURE:
<221> NAME/KEY: misc_feature
<222> LOCATION: (1064)..(1065)
<223> OTHER INFORMATION: n is a, c, g, or t
<220> FEATURE:
<221> NAME/KEY: misc_feature
<222> LOCATION: (1240)..(1240)
<223> OTHER INFORMATION: n is a, c, g, or t
<220> FEATURE:
<221> NAME/KEY: misc_feature
<222> LOCATION: (1862)..(1862)
<223> OTHER INFORMATION: n is a, c, g, or t
<220> FEATURE:
<221> NAME/KEY: misc_feature
<222> LOCATION: (1878)..(1878)
<223> OTHER INFORMATION: n is a, c, g, or t
<220> FEATURE:
<221> NAME/KEY: misc_feature
<222> LOCATION: (1899)..(1900)
<223> OTHER INFORMATION: n is a, c, g, or t
<220> FEATURE:
<221> NAME/KEY: misc_feature
<222> LOCATION: (1906)..(1906)
<223> OTHER INFORMATION: n is a, c, g, or t
<220> FEATURE:
<221> NAME/KEY: misc_feature
```

```
<222> LOCATION: (1917)..(1917)
<223> OTHER INFORMATION: n is a, c, g, or t
<220> FEATURE:
<221> NAME/KEY: misc_feature
<222> LOCATION: (1928)..(1929)
<223> OTHER INFORMATION: n is a, c, g, or t
<220> FEATURE:
<221> NAME/KEY: misc_feature
<222> LOCATION: (2395)..(2395)
<223> OTHER INFORMATION: n is a, c, g, or t

<400> SEQUENCE: 28
cccctgcagc tggcctcaat gttaagatct taaggggcac agcacagacc ttgtcttgtc      60
tatctccctg gcacctctca cagagtacag cttattaaca gatgttccag aaactgttac     120
tgaacaatcg gcttgatgct gtgggcttgt ctgcatcttg caactgtcac ctggctgaga     180
aatttcttct ataaataagc agtttctgtt tcagatgtga tatgccctga tatttacacc     240
ctgtctctta ccccatccaa gactcaaact tagaaacttg aattagatgt ggtattcaaa     300
tccttacgtg ccgcgaagac acagacagcc cccgtaagaa cccacgaagc aggcgaagtt     360
cattgttctc aacattctag ctgctcttgc tgcatttgct ctggaattct gtagagata     420
ttacttgtcc ttccaggctg ttctttctgt agctcccttg ttttcttttt gtgatcatgt     480
tgcagatggc tgggcagtgc tcccaaaatg aatattttga cagtttgttg catgcttgca     540
taccttgtca acttcgatgt tcttctaata ctcctcctct aacatgtcag cgttattgta     600
atgcaagtaa gtaatattgc ttgaacgatt attcattggt gtgaactatt ctgtctatat     660
ggactgctta ttcagagaat caacataatg ggcatgatgg tgagttttct tgaatcaaaa     720
agagaaagga agcaaggcag tgattttaat gtttatggaa acaaagtaat tatttggaac     780
tgaacttgat atgattcagc actattagca acatagattt ttttaaaaa tcagctcttc     840
taattaagtg atatttagaa tttaaaagtc aatgttcatt aattaaggtg attgaatgga     900
aataatccat acttgattat tttgctatca aaacaatcca taattcatta ttttagcaa     960
aataatcaag tatgacagcc gggtgcggtg gatggctcac acctgtaatc ccagcacttt    1020
gggaggccga gatgggtgaa tcacctgagg tcggcagttt gagnncagcc tggccaacct    1080
ggtgaaaccc tgtctctact aaaaatacaa aaaattagct gggcatggtg gcacaggtct    1140
gtaatcccag ctactcggga ggctgaggca ggagaatcgt ttgaacttgg gaggtggagg    1200
ttgcagtgag ccgagatcgc gccactgcaa ctctagcctn ggcaacagag caagactttg    1260
tctcaaaata aataaataaa taataacaat aaagtatgtg aatattatgt tatcagctca    1320
ttatctgtct gatgttcttt tcataaaggt gtgaccaatt cagtgaaagg aacgaatgcg    1380
attctctgga cctgtttggg actgagctta ataatttctt tggcagtttt cgtgctaatg    1440
tttttgctaa ggaagataag ctctgaacca ttaaaggacg agtttaaaaa cacaggttgg    1500
tttgatggtg aatctttgaa atctatttcc aggggatggc tattgtgagt ttcagttcct    1560
tttctttttt tagcgttgac tatttcactt cgttacagcc ctttcgaatg tgttagaaca    1620
ttgttacatt aaatgaactt ggtagaggtg agccatcttc attctgattt tgacaccttg    1680
gcagattttc tacaatgtca gtcttctcca ggattcttcc actgttaatt actctattga    1740
aagtactaag gctttcttgg gaaacatcag tctctttgac taaagttagc acatcgatta    1800
aatgccacat tatcagaaac tcctagccag gtctgctact gtcaggaaaa gcatatttgt    1860
cnagatctat ggtcakgntt ttatacaaat ataggtgtnn yttgcntgag tgaacantt     1920
actactgnna aaatgttaga aatgaataac cagttgctcc tgaattattt gaggaatcat    1980
```

| | |
|---|---|
| ctaaaaaata attattttta agcaatagag aaccagtccc agaaaaatga atgttctact | 2040 |
| taagtgcctc ttaagataaa aaatacttct gcagcacctt tgctcatgat tggattccca | 2100 |
| agcatgtaca gccactgccc tatttctgta tgcatttatt tatttattta tttatttatt | 2160 |
| tatttagaga tggagtctcg ctctgtggcc caaggctgga gtgcagtggc gtgatctcaa | 2220 |
| ctcactgcag cctctgcctc ttgggttcaa acaattctcc catctcagcc tcctgagtaa | 2280 |
| ctggactata ggtatgtgcc atcacctccg actaattttt gtacttttg gtagagacag | 2340 |
| ggtttcatca tgttggccag gatggtctca agctcctgac cacaagtgat ctgcncgcct | 2400 |
| cagcttccca aagtgctggg attacaggcg tgagccacag ggcccagcac atactcattc | 2460 |
| tttttactg aaaagatctg tttcaagctg ggtgttggtg gctatggagc tgtagtccga | 2520 |
| ctgctctgta ggctaacgtg ggaggattgc ttgagcccag agtttgaatg cagcctgggc | 2580 |
| aacacagtaa gaccccacct ctaaaaaatg aaaaaatctc tctcacattg ctttgagtcc | 2640 |
| cgatgtgtac tgctaagact ctcatgacca cattctctgt gaagtttggg ttaagttccg | 2700 |
| ttctacataa ttaggatcag gtctcctggg catggctaac attgacctgg aaaagagcag | 2760 |
| gactggtgat gaaattattc ttccgagagg cctcgagtac acggtggaag aatgcacctg | 2820 |
| tgaagactgc atcaagagca aaccgaaggt cgactctgac cattgctttc cactcccagc | 2880 |
| tatggaggaa ggcgcaacca ttcttgtcac cacgaaaacg aatgactatt gcaagagcct | 2940 |
| gccagctgct ttgagtgcta cggagataga gaaatcaatt tctgctaggt aattaaccat | 3000 |
| ttcgactcga gcagtgccac tttaaaaatc ttttgtcaga atagatgatg tgtcagatct | 3060 |
| ctttaggatg actgtatttt tcagttgccg atacagcttt ttgtcctcta actgtggaaa | 3120 |
| ctctttatgt tagatatatt tctctaggtt actgttggga gcttaatggt agaaacttcc | 3180 |
| ttggtttcat gattaaagtc tttttttttc ctgacatcta agttttatt aacgtgagtt | 3240 |
| tttaaaaaca agcatgtata ccagtgtggg gggtgagggt gggagagaaa ggtgggaggg | 3300 |
| ggaaagaatt ctaacctatt gataataaag ctccagtttt ggccaggcgc ggtgctcatg | 3360 |
| cctgtaatcc cagcactttg aaaggccgag gcgggcagat tacctgaggt caggaatttg | 3420 |
| agaccagcct ggccaacatg gtgaaaccct gtctttacta aaaatacaaa aattagctgg | 3480 |
| gcatggtggt aggcacctgt aatcccagct actcaggagg ctgaggcagg agaatcgctt | 3540 |
| gaacctggga ggtggaggtt gcaatgagct gagatagcat ccctgcactc cagcctgggc | 3600 |
| aagagggtga gactccgtct caaaacaaaa caacacaaac aaacaaaaag tacctccagc | 3660 |
| ttcatcttct gctggatttt atagcgcccc caaagatatg tggtccttaa aaattgtata | 3720 |
| ccacttattc aggagtcttg ttcctgaaag ggttgttctt gttacagccc tagtctgggc | 3780 |
| tgtaatcagc ttcttaaggt cc | 3802 |

<210> SEQ ID NO 29
<211> LENGTH: 184
<212> TYPE: PRT
<213> ORGANISM: Homo sapiens

<400> SEQUENCE: 29

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

```
Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
 65                  70                  75                  80

Ser Ser Glu Pro Leu Lys Asp Glu Phe Lys Asn Thr Gly Ser Gly Leu
                 85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
                115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 30
<211> LENGTH: 1968
<212> TYPE: DNA
<213> ORGANISM: Homo sapiens

<400> SEQUENCE: 30
aggcccctgc ctgccccagc atccctgcg  cgaagctggg tgccccggag agtctgacca      60
ccatgccacc tcctcgcctc ctcttcttcc tcctcttcct cacccccatg gaagtcaggc     120
ccgaggaacc tctagtggtg aaggtggaag agggagataa cgctgtgctg cagtgcctca     180 aggggaccte agatggcccc actcagcagc tgacctggtc tcgggagtcc ccgcttaaac     240
ccttcttaaa actcagcctg gggctgccag gcctgggaat ccacatgagg cccctggcca     300
tctggctttt catcttcaac gtctctcaac agatgggggg cttctacctg tgccagccgg     360 ggccccctc tgagaaggcc tggcagcctg gctggacagt caatgtggag ggcagcgggg     420
agctgttccg gtggaatgtt tcggacctag gtggcctggg ctgtgccctg aagaacaggt     480
cctcagaggg ccccagctcc ccttccggga agctcatgag ccccaagctg tatgtgtggg     540
ccaaagaccg ccctgagatc tgggaggag agcctccgtg tctcccaccg agggacagcc     600
tgaaccagag cctcagccag gacctcacca tggcccctgg ctccacactc tggctgtcct     660
gtgggggtac ccctgactct gtgtccaggg ccccctctc ctggacccat gtgcacccca     720
aggggcctaa gtcattgctg agcctagagc tgaaggacga tcgcccggcc agagatatgt     780
gggtaatgga cgggtctg ttgttgcccc gggccacagc tcaagacgct ggaaagtatt     840
attgtcaccg tggcaacctg accatgtcat tccacctgga gatcactgct cggccagtac     900
tatggcactg gctgctgagg actggtggct ggaaggtctc agctgtgact ttggcttatc     960
tgatcttctg cctgtgttcc cttgtgggca ttcttcatct tcaaagagcc ctggtcctga    1020
ggaggaaaag aaagcgaatg actgacccca ccaggagatt cttcaaagtg acgcctcccc    1080
caggaagcgg gccccagaac cagtacggga acgtgctgtc tctccccaca cccacctcag    1140
gcctcggacg cgcccagcgt tgggccgcag gctgggggg cactgccccg tcttatggaa    1200
acccgagcag cgacgtccag gcggatgag ccttggggtc ccggagcccg ccggagtgg    1260 gcccagaaga agaggaaggg gagggctatg aggaacctga cagtgaggag gactccgagt    1320
```

```
tctatgagaa cgactccaac cttgggcagg accagctctc ccaggatggc agcggctacg    1380
agaaccctga ggatgagccc ctgggtcctg aggatgaaga ctccttctcc aacgctgagt    1440
cttatgagaa cgaggatgaa gagctgaccc agccggtcgc aggacaatg gacttcctga     1500 gccctcatgg gtcagcctgg gaccccagcc gggaagcaac ctccctggca gggtcccagt    1560
cctatgagga tatgagagga atcctgtatg cagccccca gctccgctcc attcggggcc     1620
agcctggacc caatcatgag gaagatgcag actcttatga aacatggat aatcccgatg     1680 ggccagaccc agcctgggga ggaggggcc gcatgggcac ctggagcacc aggtgatcct    1740
caggtggcca gcctggatct cctcaagtcc caagattca cctgactc tgaaatctga      1800 agacctcgag cagatgatgc caacctctgg agcaatgttg cttaggatgt gtgcatgtgt    1860
gtaagtgtgt gtgtgtgtgt gtgtgtgtat acatgccagt gacacttcca gtccccttg    1920 tattccttaa ataaactcaa tgagctcttc caatcctaaa aaaaaaa                 1968
```

<210> SEQ ID NO 31
<211> LENGTH: 557
<212> TYPE: PRT
<213> ORGANISM: Homo sapiens

<400> SEQUENCE: 31

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
```

```
              260                 265                 270
Glu Ile Thr Ala Arg Pro Val Leu Trp His Trp Leu Leu Arg Thr Gly
            275                 280                 285
Gly Trp Lys Val Ser Ala Val Thr Leu Ala Tyr Leu Ile Phe Cys Leu
            290                 295                 300
Cys Ser Leu Val Gly Ile Leu His Leu Gln Arg Ala Leu Val Leu Arg
305                 310                 315                 320
Arg Lys Arg Lys Arg Met Thr Asp Pro Thr Arg Phe Phe Lys Val
                325                 330                 335
Thr Pro Pro Pro Gly Ser Gly Pro Gln Asn Gln Tyr Gly Asn Val Leu
                340                 345                 350
Ser Leu Pro Thr Pro Thr Ser Gly Leu Gly Arg Ala Gln Arg Trp Ala
                355                 360                 365
Ala Gly Leu Gly Gly Thr Ala Pro Ser Tyr Gly Asn Pro Ser Ser Asp
                370                 375                 380
Val Gln Ala Asp Gly Ala Leu Gly Ser Arg Ser Pro Pro Gly Val Gly
385                 390                 395                 400
Pro Glu Glu Glu Glu Gly Glu Gly Tyr Glu Glu Pro Asp Ser Glu Glu
                405                 410                 415
Asp Ser Glu Phe Tyr Glu Asn Asp Ser Asn Leu Gly Gln Asp Gln Leu
                420                 425                 430
Ser Gln Asp Gly Ser Gly Tyr Glu Asn Pro Glu Asp Glu Pro Leu Gly
                435                 440                 445
Pro Glu Asp Glu Asp Ser Phe Ser Asn Ala Glu Ser Tyr Glu Asn Glu
                450                 455                 460
Asp Glu Glu Leu Thr Gln Pro Val Ala Arg Thr Met Asp Phe Leu Ser
465                 470                 475                 480
Pro His Gly Ser Ala Trp Asp Pro Ser Arg Glu Ala Thr Ser Leu Ala
                485                 490                 495
Gly Ser Gln Ser Tyr Glu Asp Met Arg Gly Ile Leu Tyr Ala Ala Pro
                500                 505                 510
Gln Leu Arg Ser Ile Arg Gly Gln Pro Gly Pro Asn His Glu Glu Asp
                515                 520                 525
Ala Asp Ser Tyr Glu Asn Met Asp Asn Pro Asp Gly Pro Asp Pro Ala
                530                 535                 540
Trp Gly Gly Gly Gly Arg Met Gly Thr Trp Ser Thr Arg
545                 550                 555

<210> SEQ ID NO 32
<211> LENGTH: 157
<212> TYPE: DNA
<213> ORGANISM: Homo sapiens

<400> SEQUENCE: 32
cctggccatg accccctga tccctcagag caaggatgag aacagcgatg actacacgac      60
ctttgatgat gtgggcagcc tgtggaccac cctgtccacg tttgtggccc tcttcatcct     120
caccctcctc tacagcggca ttgtcacttt catcaag                              157

<210> SEQ ID NO 33
<211> LENGTH: 51
<212> TYPE: PRT
<213> ORGANISM: Homo sapiens

<400> SEQUENCE: 33

Leu Ala Met Thr Pro Leu Ile Pro Gln Ser Lys Asp Glu Asn Ser Asp
```

```
            1               5                  10                 15
          Asp Tyr Thr Thr Phe Asp Asp Val Gly Ser Leu Trp Thr Thr Leu Ser
                       20                  25                  30
          Thr Phe Val Ala Leu Phe Ile Leu Thr Leu Leu Tyr Ser Gly Ile Val
                       35                  40                  45
          Thr Phe Ile
               50

<210> SEQ ID NO 34
<211> LENGTH: 120
<212> TYPE: DNA
<213> ORGANISM: Homo sapiens

<400> SEQUENCE: 34
tgtgggccac cgcctccacc ttcatcgtcc tcttcctcct gagcctcttc tacagtacca      60
ccgtcacctt gttcaaggta gcacggctgt ggcacaggga ggagggtgca gggcgagtgt     120

<210> SEQ ID NO 35
<211> LENGTH: 3594
<212> TYPE: DNA
<213> ORGANISM: Homo sapiens

<400> SEQUENCE: 35
gtctatcagc gatttcatct tcaggcctgg actacaccac tcaccctccc agtgtgcttg      60
agaaacaaac tgcacccact gaactccgca gctagcatcc aaatcagccc ttgagatttg     120
aggccttgga gactcagatc ctgaacaaga gagaacaaaa tctctacttt gatggaactt     180
ccattctgtg gggaagagac tgacaataag caattaaata aataagaact cagcagtagg     240
ccttgcctca gatccaaggt cactcggaag aggccatgtc taccctcaat gacactcatg     300
gaggaaatgc tgagagaagc attcagatgc atgacacaag gtaagactgc caaaaatctt     360
gttcttgctc tcctcatttt gttatttgtt ttattttag gagttttgag agcaaaatga     420
caacacccag aaattcagta atgggacttt cccggcaga gccaatgaaa ggccctattg       480
ctatgcaatc tggtccaaaa ccactcttca ggaggatgtc ttcactgtgt ggccccacgc     540
aaagcttctt catgagggaa tctaagactt tggggctgt ccagattatg aatgggctct      600
tccacattgc cctgggggt cttctgatga tcccagcagg gatctatgca cccatctgtg      660
tgactgtgtg gtaccctctc tggggaggca ttatgtatat tatttccgga tcactcctgg     720
cagcaacgga gaaaaactcc aggaagtgtt tggtcaaagg aaaaatgata atgaattcat     780
tgagcctctt tgctgccatt tctggaatga ttctttcaat catggacata cttaatatta     840
aaatttccca ttttttaaaa atggagagtc tgaatttat tagagctcac acaccatata      900
ttaacatata caactgtgaa ccagctaatc cctctgagaa aaactcccca tctacccaat     960
actgttacag catacaatct ctgttcttgg gcattttgtc agtgatgctg atctttgcct    1020
tcttccagga acttgtaata gctggcatcg ttgagaatga atggaaaga acgtgctcca     1080
gacccaaatc taacatagtt ctcctgtcag cagaagaaaa aaagaacag actattgaaa     1140
taaaagaaga agtggttggg ctaactgaaa catcttccca accaaagaat gaagaagaca    1200
ttgaaattat tccaatccaa gaagaggaag aagaagaaac agagacgaac tttccagaac    1260
ctcccccaaga tcaggaatcc tcaccaatag aaaatgacag ctctcccttaa gtgatttctt    1320
ctgtttctg tttccttttt taaacattag tgttcatagc ttccaagaga catgctgact      1380
ttcatttctt gaggtactct gcacatacgc accacatctc tatctggcct ttgcatggag    1440
```

```
tgaccatagc tccttctctc ttacattgaa tgtagagaat gtagccattg tagcagcttg   1500
tgttgtcacg cttcttcttt tgagcaactt tcttacactg aagaaaggca gaatgagtgc   1560
ttcagaatgt gatttcctac taacctgttc cttggatagg cttttagta tagtattttt    1620 ttttgtcatt ttctccatca acaaccaggg agactgcacc tgatggaaaa gatatatgac   1680
tgcttcatga cattcctaaa ctatcttttt tttattccac atctacgttt ttggtggagt   1740 ccctttgca tcattgtttt aaggatgata aaaaaaata acaactaggg acaatacaga     1800
acccattcca tttatctttc tacagggctg acattgtggc acattcttag agttaccaca   1860
ccccatgagg gaagctctaa atagccaaca cccatctgtt ttttgtaaaa acagcatagc   1920
ttatacatgg acatgtctct gccttaactt ttcctaactc ccactctagg ctattgtttg   1980
catgtctacc tacttttagc cattatgcga gaaaagaaaa aaatgaccat agaaaatgcc   2040
accatgaggt gcccaaattt caaataataa ttaacattta gttatattta taatttccag   2100
atgacaaagt atttcatcaa ataacttcat ttgatgttcc atgatcaaga aagaatccct   2160
atctctattt tacaagtaat tcaaagaggc caaataactt gtaaacaaga aaggtaact    2220 tgtcaacagt cataactagt aattatgaga gccttgtttc ataaccaggt cttcttactc   2280
aaatcctgtg atgtttgaaa taaccaaatt gtctctccaa tgtctgcata aactgtgaga   2340
gccaagtcaa cagcttttat caagaattta ctctctgacc agcaataaac aagcactgag   2400
agacacagag agccagattc agattttacc catggggata aaaagactca gactttcacc   2460
acatttggaa aactacttgc atcataaata tataataact ggtagtttat atgaagcaga   2520
cactaagtgc tatagacact ctcagaatat catacttgga aacaatgtaa ttaaaatgcc   2580
gaatctgagt caacagctgc cctacttttc aattcagata tactagtacc ttacctagaa   2640
ataatgttaa cctagggtga agtcactata atctgtagtc tattatttgg gcatttgcta   2700
catgatgagt gctgccagat tgtggcaggt aaagagacaa tgtaatttgc actccctatg   2760
atatttctac attttagcg accactagtg aagacattc cccaaaatta gaaaaaagg      2820 agatagaaga tttctgtcta tgtaaagttc tcaaaatttg ttctaaatta ataaaactat   2880
ctttgtgttc ttttctgcaa cagatgattc caacatgggt gtttgtctat tcttctttac   2940
tcttgaaaca ttagaccatg ggaggctctt acagccttga gttgatattt atacaaccca   3000
aatctaggtt tgaacggtga ggtgtcaggt catcaaatat tcatgtctat atagtcttac   3060
acaggttctc aaaaaaaatg ttcatgggat aggtcattga taatggattc cttattctga   3120
gaactccaga cgactgaaat atatgagaga aggaaaagga catagtagga gcaggcctga   3180
gaaaaaaatg aaagtcagaa atcttaaaa aaatacaaga tcttatttct atcttatttt    3240
ttctcctctt ctgaaatata tatgaggatt cctctccaaa cccatggttt ctctaagaat   3300
tttgagtcat ttgtatgacc tcaaataatt agttttagct gacctcacat aactccttat   3360
aataggagac atctttaatg tctgctatta aagaaggatg aaaattccta tgaccttctc   3420
cccgattatc cctttggcaa tatagagtca ataataaca ttgaccaata gtaaacatgc    3480
tttgccaaga agtagaagat atattctcta gccttagttt ttcctcccaa tttgcatttt   3540
tgtaaaaata atgttgtatc cacaaaggaa ataaacttta aaaacccaag tgca         3594
```

<210> SEQ ID NO 36
<211> LENGTH: 297
<212> TYPE: PRT
<213> ORGANISM: Homo sapiens

<400> SEQUENCE: 36

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
                100                 105                 110

Val Lys Gly Lys Met Ile Met Asn Ser Leu Ser Leu Phe Ala Ala Ile
            115                 120                 125

Ser Gly Met Ile Leu Ser Ile Met Asp Ile Leu Asn Ile Lys Ile Ser
        130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
                180                 185                 190

Ile Leu Ser Val Met Leu Ile Phe Ala Phe Phe Gln Glu Leu Val Ile
            195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 37
<211> LENGTH: 1410
<212> TYPE: DNA
<213> ORGANISM: Homo sapiens

<400> SEQUENCE: 37
gtcctcccgc cccgccgctt ggtggcggcc gcatgctgcc cggatataaa gggtcggccc      60
cacatcccag ggaccagcga gcggccttga gaggctctgg ctcttgcttc ttaggcggcc     120
cgaggacgcc atggccgagt gcccgacact cggggaggca gtcaccgacc acccggaccg     180
cctgtgggcc tgggagaagt tcgtgtattt ggacgagaag cagcacgcct ggctgccctt     240
aaccatcgag ataaaggata ggttacagtt acgggtgctc ttgcgtcggg aagacgtcgt     300
cctggggagg cctatgaccc ccacccagat aggcccaagc ctgctgccta tcatgtggca     360
gctctaccct gatggacgat accgatcctc agactccagt ttctggcgct tagtgtacca     420
```

-continued

```
catcaagatt gacggcgtgg aggacatgct tctcgagctg ctgccagatg actgatgtat    480
ggtcttggca gcacctgtct cctttcaccc cagggcctga gcctggccag cctacaatgg    540
ggatgttgtg tttctgttca ccttcgttta ctatgcctgt gtcttctcca ccacgctggg    600
gtctgggagg aatggacaga cagaggatga gctctaccca gggcctgcag gacctgcctg    660
tagcccactc tgctcgcctt agcactacca ctcctgccaa ggaggattcc atttggcaga    720
gcttcttcca ggtgcccagc tatacctgtg cctcggcttt tctcagctgg atgatggtct    780
tcagcctctt tctgtccctt ctgtccctca gcactagt atttcatgtt gcacacccac    840
tcagctccgt gaacttgtga gaacacagcc gattcacctg agcaggacct ctgaaaccct    900
ggaccagtgg tctcacatgg tgctacgcct gcatgtaaac acgctgcaa acgctgcctg    960 ccggtaaaca cgcctgcaaa cgctgcctgc cgtaaacac gcctgcaaac gctgcctgcc   1020
cacacaggtt cacgtgcagc tcaaggaaag gcctgaaagg agcccttatc tgtgctcagg   1080
actcagaagc ctctgggtca gtggtccaca tcccggacg cagcaggagg ccaggccggc   1140
gagccctgtg gatgagccct cagaacccctt ggcttgccca cgtggaaaag ggatagaggt   1200
tgggtttccc cccttttata gatggtcacg cacctgggtg ttacaaagtt gtatgtggca   1260
tgaatacttt ttgtaatgat tgattaaatg caagatagtt tatctaactt cgtgcggaat   1320
cagcttctat ccttgactta gattctggtg gagagaagtg agaataggca gcccccaaat   1380
aaaaaatatt catggaaaaa aaaaaaaaa                                    1410
```

<210> SEQ ID NO 38
<211> LENGTH: 114
<212> TYPE: PRT
<213> ORGANISM: Homo sapiens

<400> SEQUENCE: 38

```
Met Ala Glu Cys Pro Thr Leu Gly Glu Ala Val Thr Asp His Pro Asp
1               5                   10                  15

Arg Leu Trp Ala Trp Glu Lys Phe Val Tyr Leu Asp Glu Lys Gln His
            20                  25                  30

Ala Trp Leu Pro Leu Thr Ile Glu Ile Lys Asp Arg Leu Gln Leu Arg
        35                  40                  45

Val Leu Leu Arg Arg Glu Asp Val Val Leu Gly Arg Pro Met Thr Pro
    50                  55                  60

Thr Gln Ile Gly Pro Ser Leu Leu Pro Ile Met Trp Gln Leu Tyr Pro
65                  70                  75                  80

Asp Gly Arg Tyr Arg Ser Ser Asp Ser Ser Phe Trp Arg Leu Val Tyr
                85                  90                  95

His Ile Lys Ile Asp Gly Val Glu Asp Met Leu Leu Glu Leu Leu Pro
            100                 105                 110

Asp Asp
```

<210> SEQ ID NO 39
<211> LENGTH: 685
<212> TYPE: DNA
<213> ORGANISM: Homo sapiens

<400> SEQUENCE: 39

```
ataatagggc cggtgctgcc tgccgaagcc ggcggctgag aggcagcgaa ctcatctttg     60
ccagtacagg agcttgtgcc gtggcccaca gcccacagcc cacagccatg ggctgggacc    120
tgacggtgaa gatgctggcg ggcaacgaat tccaggtgtc cctgagcagc tccatgtcgg    180
```

```
tgtcagagct gaaggcgcag atcacccaga agatcggcgt gcacgccttc cagcagcgtc    240
tggctgtcca cccgagcggt gtggcgctgc aggacagggt ccccttgcc agccagggcc     300 tgggccccgg cagcacggtc ctgctggtgg tggacaaatg cgacgaacct ctgagcatcc    360
tggtgaggaa taacaagggc cgcagcagca cctacgaggt acggctgacg cagaccgtgg    420
cccacctgaa gcagcaagtg agcgggctgg agggtgtgca ggacgacctg ttctggctga    480
ccttcgaggg gaagccctg gaggaccagc tcccgctggg ggagtacggc tcaagcccc     540 tgagcaccgt gttcatgaat ctgcgcctgc ggggaggcgg cacagagcct ggcgggcgga    600
gctaagggcc tccaccagca tccgagcagg atcaagggcc ggaaataaag gctgttgtaa    660
agagaaaaaa aaaaaaaaaa aaaaa                                          685
```

<210> SEQ ID NO 40
<211> LENGTH: 165
<212> TYPE: PRT
<213> ORGANISM: Homo sapiens

<400> SEQUENCE: 40

```
Met Gly Trp Asp Leu Thr Val Lys Met Leu Ala Gly Asn Glu Phe Gln
1               5                   10                  15

Val Ser Leu Ser Ser Met Ser Val Ser Glu Leu Lys Ala Gln Ile
            20                  25                  30

Thr Gln Lys Ile Gly Val His Ala Phe Gln Gln Arg Leu Ala Val His
        35                  40                  45

Pro Ser Gly Val Ala Leu Gln Asp Arg Val Pro Leu Ala Ser Gln Gly
    50                  55                  60

Leu Gly Pro Gly Ser Thr Val Leu Leu Val Val Asp Lys Cys Asp Glu
65                  70                  75                  80

Pro Leu Ser Ile Leu Val Arg Asn Asn Lys Gly Arg Ser Ser Thr Tyr
                85                  90                  95

Glu Val Arg Leu Thr Gln Thr Val Ala His Leu Lys Gln Gln Val Ser
            100                 105                 110

Gly Leu Glu Gly Val Gln Asp Asp Leu Phe Trp Leu Thr Phe Glu Gly
        115                 120                 125

Lys Pro Leu Glu Asp Gln Leu Pro Leu Gly Glu Tyr Gly Leu Lys Pro
    130                 135                 140

Leu Ser Thr Val Phe Met Asn Leu Arg Leu Arg Gly Gly Gly Thr Glu
145                 150                 155                 160

Pro Gly Gly Arg Ser
                165
```

<210> SEQ ID NO 41
<211> LENGTH: 3444
<212> TYPE: DNA
<213> ORGANISM: Homo sapiens

<400> SEQUENCE: 41

```
cgagcagaaa tgaaaccgaa actgaattgt ccgggaaatt cgcggtgggg gcggagagcg     60
cagggagaag taagcccagt gcaggatcct gaggcccgtg tttgcaggac cagggccggc    120
cttccgattc cccattcatt ccagaagcac cgaaccacgc tgtgcccgga tcccaagtgc    180
agcggcaccc agcgtggggcc tggggttgcc ggttgacccg tcctcagcc tggtagcaga     240 ggccaggcca gtgccacaag gcacctaagt ccacctgggc ctggagcagg acaggttgca    300
aaagaaaata tctcgggacc cccaaactcc ttatgctaag ggaaacatcg agcctgggaa    360
```

```
ctgagccatc aacgctgcca ttctttttcc caaacagaac cctgttgtca gaggtacacc    420
cagagcaact ccacaccggg tgcatgccac agcaactcca tcttaaatag agctggtaa     480 aacgaggctg atacctactg ggctgcattc ccagacggca tagcgaggag gtgctgaaga    540
gcgcaggttt ggagaatgat cacctggatt ggaaccatag ctctaccaat atggaaccca    600
gctccttagg cctcggtctt ctcatggaga acatggtgtg ataatcctac tcctctggga    660
gggtggctgt taagccttgg accgcagttg ccggccagga atcccagtgt cacggtggac    720
acgcctccct cgcgcccttg ccgcccacct gctcacccag ctcagggcct ttggaattct    780
gtggccacac tgcgaggaga tcggttctgg gtcggaggct acaggaagac tcccactccc    840
tgaaatctgg agtgaagaac gccgccatcc agccaccatt ccaaggaggt gcaggagaac    900
agctctgtga taccatttaa cttgttgaca ttacttttat ttgaaggaac gtatattaga    960
gcttactttg caaagaagga agatggttgt ttccgaagtg gacatcgcaa aagctgatcc   1020
agctgctgca tcccaccctc tattactgaa tggagatgct actgtggccc agaaaaatcc   1080
aggctcggtg gctgagaaca acctgtgcag ccagtatgag gagaaggtgc gcccctgcat   1140
cgacctcatt gactccctgc gggctctagg tgtggagcag gacctggccc tgccagccat   1200
cgccgtcatc ggggaccaga gctcgggcaa gagctccgtg ttggaggcac tgtcaggagt   1260 tgccccttccc agaggcagcg ggatcgtgac cagatgcccg ctggtgctga aactgaagaa   1320
acttgtgaac gaagataagt ggagaggcaa ggtcagttac caggactacg agattgagat   1380
ttcggatgct tcagaggtag aaaaggaaat taataaagcc cagaatgcca tcgccgggga   1440
aggaatggga atcagtcatg agctaatcac cctggagatc agctcccgag atgtcccgga   1500
tctgactcta atagaccttc ctggcataac cagagtggct gtgggcaatc agcctgctga   1560
cattgggtat aagatcaaga cactcatcaa gaagtacatc cagaggcagg agacaatcag   1620
cctggtggtg gtccccagta atgtggacat cgccaccaca gaggctctca gcatggccca   1680
ggaggtggac cccgagggag acaggaccat cggaatcttg acgaagcctg atctggtgga   1740
caaaggaact gaagacaagg ttgtggacgt ggtgcggaac ctcgtgttcc acctgaagaa   1800
gggttacatg attgtcaagt gccggggcca gcaggagatc caggaccagc tgagcctgtc   1860
cgaagccctg cagagagaga agatcttctt tgagaaccac ccatatttca gggatctgct   1920
ggaggaagga aaggccacgg ttccctgcct ggcagaaaaa cttaccagcg agctcatcac   1980
acatatctgt aaatctctgc ccctgttaga aaatcaaatc aaggagactc accagagaat   2040
aacagaggag ctacaaaagt atggtgtcga cataccggaa gacgaaaatg aaaaaatgtt   2100
cttcctgata gataaagtta atgcctttaa tcaggacatc actgctctca tgcaaggaga   2160
ggaaactgta ggggaggaag acattcggct gtttaccaga ctccgacacg agttccacaa   2220
atggagtaca ataattgaaa acaatttttca agaaggccat aaaattttga gtagaaaaat   2280
ccagaaattt gaaaatcagt atcgtggtag agagctgcca ggctttgtga attacaggac   2340
atttgagaca atcgtgaaac agcaaatcaa ggcactggaa gagccggctg tggatatgct   2400
acacaccgtg acgatatgg tccggcttgc tttcacagat gtttcgataa aaaattttga   2460 agagttttttt aacctccaca gaaccgccaa gtccaaaatt gaagacatta gagcagaaca   2520
agagagagaa ggtgagaagc tgatccgcct ccacttccag atggaacaga ttgtctactg   2580
ccaggaccag gtatacaggg gtgcattgca gaaggtcaga gagaaggagc tggaagaaga   2640
aaagaagaag aaatcctggg attttggggc tttccagtcc agctcggcaa cagactcttc   2700
```

```
catggaggag atctttcagc acctgatggc ctatcaccag gaggccagca agcgcatctc    2760
cagccacatc cctttgatca tccagttctt catgctccag acgtacggcc agcagcttca    2820
gaaggccatg ctgcagctcc tgcaggacaa ggacacctac agctggctcc tgaaggagcg    2880
gagcgacacc agcgacaagc ggaagttcct gaaggagcgg cttgcacggc tgacgcaggc    2940
tcggcgccgg cttgcccagt tccccggtta accacactct gtccagcccc gtagacgtgc    3000
acgcacactg tctgcccccg ttcccgggta gccactggac tgacgacttg agtgctcagt    3060
agtcagactg gatagtccgt ctctgcttat ccgttagccg tggtgattta gcaggaagct    3120
gtgagagcag tttggtttct agcatgaaga cagagcccca ccctcagatg cacatgagct    3180
ggcgggattg aaggatgctg tcttcgtact gggaaaggga ttttcagccc tcagaatcgc    3240
tccaccttgc agctctcccc ttctctgtat tcctagaaac tgacacatgc tgaacatcac    3300
agcttatttc ctcatttttta taatgtccct tcacaaaccc agtgttttag gagcatgagt    3360
gccgtgtgtg tgcgtcctgt cggagccctg tctcctctct ctgtaataaa ctcatttcta    3420
gcagacaaaa aaaaaaaaaa aaaa                                           3444
```

<210> SEQ ID NO 42
<211> LENGTH: 662
<212> TYPE: PRT
<213> ORGANISM: Homo sapiens

<400> SEQUENCE: 42

```
Met Val Val Ser Glu Val Asp Ile Ala Lys Ala Asp Pro Ala Ala
1               5                   10                  15

Ser His Pro Leu Leu Asn Gly Asp Ala Thr Val Ala Gln Lys Asn
            20                  25                  30

Pro Gly Ser Val Ala Glu Asn Asn Leu Cys Ser Gln Tyr Glu Glu Lys
            35                  40                  45

Val Arg Pro Cys Ile Asp Leu Ile Asp Ser Leu Arg Ala Leu Gly Val
50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Val Pro Ser Asn Val Asp Ile Ala
    210                 215                 220

Thr Thr Glu Ala Leu Ser Met Ala Gln Glu Val Asp Pro Glu Gly Asp
225                 230                 235                 240
```

```
Arg Thr Ile Gly Ile Leu Thr Lys Pro Asp Leu Val Asp Lys Gly Thr
                245                 250                 255

Glu Asp Lys Val Val Asp Val Arg Asn Leu Val Phe His Leu Lys
        260                 265                 270

Lys Gly Tyr Met Ile Val Lys Cys Arg Gly Gln Gln Glu Ile Gln Asp
            275                 280                 285

Gln Leu Ser Leu Ser Glu Ala Leu Gln Arg Glu Lys Ile Phe Phe Glu
        290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
                340                 345                 350

Ile Thr Glu Glu Leu Gln Lys Tyr Gly Val Asp Ile Pro Glu Asp Glu
                355                 360                 365

Asn Glu Lys Met Phe Phe Leu Ile Asp Lys Val Asn Ala Phe Asn Gln
        370                 375                 380

Asp Ile Thr Ala Leu Met Gln Gly Glu Glu Thr Val Gly Glu Glu Asp
385                 390                 395                 400

Ile Arg Leu Phe Thr Arg Leu Arg His Glu Phe His Lys Trp Ser Thr
                405                 410                 415

Ile Ile Glu Asn Asn Phe Gln Gly His Lys Ile Leu Ser Arg Lys
            420                 425                 430

Ile Gln Lys Phe Glu Asn Gln Tyr Arg Gly Arg Glu Leu Pro Gly Phe
            435                 440                 445

Val Asn Tyr Arg Thr Phe Glu Thr Ile Val Lys Gln Gln Ile Lys Ala
        450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                485                 490                 495

Asn Leu His Arg Thr Ala Lys Ser Lys Ile Glu Asp Ile Arg Ala Glu
                500                 505                 510

Gln Glu Arg Glu Gly Glu Lys Leu Ile Arg Leu His Phe Gln Met Glu
        515                 520                 525

Gln Ile Val Tyr Cys Gln Asp Gln Val Tyr Arg Gly Ala Leu Gln Lys
        530                 535                 540

Val Arg Glu Lys Glu Leu Glu Glu Lys Lys Lys Ser Trp Asp
545                 550                 555                 560

Phe Gly Ala Phe Gln Ser Ser Ser Ala Thr Asp Ser Ser Met Glu Glu
                565                 570                 575

Ile Phe Gln His Leu Met Ala Tyr His Gln Glu Ala Ser Lys Arg Ile
            580                 585                 590

Ser Ser His Ile Pro Leu Ile Ile Gln Phe Phe Met Leu Gln Thr Tyr
            595                 600                 605

Gly Gln Gln Leu Gln Lys Ala Met Leu Gln Leu Leu Gln Asp Lys Asp
        610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                645                 650                 655

Leu Ala Gln Phe Pro Gly
```

<210> SEQ ID NO 43
<211> LENGTH: 1673
<212> TYPE: DNA
<213> ORGANISM: Homo sapiens

<400> SEQUENCE: 43

```
tcccttctga ggaaacgaaa ccaacagcag tccaagctca gtcagcagaa gagataaaag      60
caaacaggtc tgggaggcag ttctgttgcc actctctctc ctgtcaatga tggatctcag     120
aaataccoca gccaaatctc tggacaagtt cattgaagac tatctcttgc cagacacgtg     180
tttccgcatg caaatcaacc atgccattga catcatctgt gggttcctga ggaaaggtg     240
cttccgaggt agctcctacc ctgtgtgtgt gtccaaggtg gtaaagggtg gctcctcagg     300
caagggcacc accctcagag gccgatctga cgctgacctg gttgtcttcc tcagtcctct     360
caccactttt caggatcagt taaatcgccg gggagagttc atccaggaaa ttaggagaca     420
gctggaagcc tgtcaaagag agagagcatt tccgtgaag tttgaggtcc aggctccacg     480
ctggggcaac ccccgtgcgc tcagcttcgt actgagttcg ctccagctcg ggaggggt      540
ggagttcgat gtgctgcctg cctttgatgc cctgggtcag ttgactggcg gctataaacc     600
taacccccaa atctatgtca agctcatcga ggagtgcacc gacctgcaga agagggcga     660
gttctccacc tgcttcacag aactacagag agacttcctg aagcagcgcc ccaccaagct     720
caagagcctc atccgcctag tcaagcactg gtaccaaaat tgtaagaaga agcttgggaa     780
gctgccacct cagtatgccc tggagctcct gacggtctat gcttgggagc gagggagcat     840
gaaaacacat ttcaacacag cccagggatt tcggacggtc ttggaattag tcataaacta     900
ccagcaactc tgcatctact ggacaaagta ttatgacttt aaaaacccca ttattgaaaa     960
gtacctgaga aggcagctca cgaaacccag gcctgtgatc ctggacccgg cggaccctac    1020
aggaaacttg ggtggtggag acccaaaggg ttggaggcag ctggcacaag aggctgaggc    1080
ctggctgaat tacccatgct ttaagaattg ggatgggtcc ccagtgagct cctggattct    1140
gctggctgaa agcaacagtg cagacgatga gaccgacgat cccaggaggt atcagaata     1200
tggttacatt ggaacacatg agtaccctca tttctctcat agacccagca cactccaggc    1260
agcatccacc ccacaggcag aagaggactg gacctgcacc atcctctgaa tgccagtgca    1320
tcttggggga aagggctcca gtgttatctg gaccagttcc ttcattttca ggtgggactc    1380
ttgatccaga gaggacaaag ctcctcagtg agctggtgta aatccagga cagaacccag    1440
gtctcctgac tcctggcctt ctatgccctc tatcctatca tagataacat tctccacagc    1500
ctcacttcat tccacctatt tctgaaaat attccctgag agagaacaga gagatttaga    1560
taagagaatg aaattccagc cttgactttc ttctgtgcac ctgatgggag ggtaatgtct    1620
aatgtattat caataacaat aaaaataaag caaataccat ttaaaaaaaa aaa           1673
```

<210> SEQ ID NO 44
<211> LENGTH: 400
<212> TYPE: PRT
<213> ORGANISM: Homo sapiens

<400> SEQUENCE: 44

```
Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
            20                  25                  30
```

Ala Ile Asp Ile Ile Cys Gly Phe Leu Lys Glu Arg Cys Phe Arg Gly
         35                  40                  45

Ser Ser Tyr Pro Val Cys Val Ser Lys Val Val Lys Gly Gly Ser Ser
     50                  55                  60

Gly Lys Gly Thr Thr Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
                 85                  90                  95

Glu Phe Ile Gln Glu Ile Arg Arg Gln Leu Glu Ala Cys Gln Arg Glu
            100                 105                 110

Arg Ala Phe Ser Val Lys Phe Glu Val Gln Ala Pro Arg Trp Gly Asn
            115                 120                 125

Pro Arg Ala Leu Ser Phe Val Leu Ser Ser Leu Gln Leu Gly Glu Gly
            130                 135                 140

Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Glu Glu
                165                 170                 175

Cys Thr Asp Leu Gln Lys Glu Glu Phe Ser Thr Cys Phe Thr Glu
            180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Lys Leu Gly
            210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Asn Pro Ile Ile Glu Lys Tyr Leu Arg
            275                 280                 285

Arg Gln Leu Thr Lys Pro Arg Pro Val Ile Leu Asp Pro Ala Asp Pro
            290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Ala Glu Ser Asn Ser Ala
            340                 345                 350

Asp Asp Glu Thr Asp Asp Pro Arg Arg Tyr Gln Lys Tyr Gly Tyr Ile
            355                 360                 365

Gly Thr His Glu Tyr Pro His Phe Ser His Arg Pro Ser Thr Leu Gln
            370                 375                 380

Ala Ala Ser Thr Pro Gln Ala Glu Glu Asp Trp Thr Cys Thr Ile Leu
385                 390                 395                 400

<210> SEQ ID NO 45
<211> LENGTH: 976
<212> TYPE: DNA
<213> ORGANISM: Homo sapiens

<400> SEQUENCE: 45
atgaatcaca ctgtccaaac cttcttctct cctgtcaaca gtggccagcc ccccaactat    60

| | |
|---|---|
| gagatgctca aggaggagca cgaggtggct gtgctggggg cgccccacaa ccctgctccc | 120 |
| ccgacgtcca ccgtgatcca catccgcagc gagacctccg tgcccgacca tgtcgtctgg | 180 |
| tccctgttca cacccctctt catgaacccc tgctgcctgg gcttcatagc attcgcctac | 240 |
| tccgtgaagg tgcgtatggc ccagggaat gctcagaggg tgccgctgag cctggagctc | 300 |
| cacctgccca catgctgcct ggggtgggga cttgtgtgtc cctgtgactg tgagtttgtg | 360 |
| tgcacctctg tcccgtgtgt gcccacgtca gtggctttgt ctgtgtgatc tgtgtgtgtg | 420 |
| tgtggcttgg ggaatctgcc cagtgcaggt ttaggaggag ctccaggag ctggctggc | 480 |
| tggctcagag tctgtccccg gctatccact agcccagagc agttctccct atagcccagt | 540 |
| aagaaattac accttcacct tccagactgg cacccacgct ctcccagaaa gtgagaaggg | 600 |
| aactcacagg tgacttcacc ccatggtggg gagaacagcc tgtgctgggg tcaaggcaga | 660 |
| aggaggatga gccccgaggc tcctggagag tctgagccyg ggtgaggaag gggaggaggt | 720 |
| ggtccctgat ctcagggcgg ggagagccaa tgaggagacg gagccatagc acgcggctct | 780 |
| cagctggggg atcctggtcc cctcaccatc tcctctcccc cagtctaggg acaggaagat | 840 |
| ggttggcgac gtgaccgggg cccaggccta tgcctccacc gccaagtgcc tgaacatctg | 900 |
| ggccctgatt ctgggcatcc tcatgaccat tctgctcatc gtcatcccag tgctgatctt | 960 |
| ccaggcctat ggatag | 976 |

<210> SEQ ID NO 46
<211> LENGTH: 133
<212> TYPE: PRT
<213> ORGANISM: Homo sapiens

<400> SEQUENCE: 46

Met Asn His Thr Val Gln Thr Phe Phe Ser Pro Val Asn Ser Gly Gln
1               5                   10                  15

Pro Pro Asn Tyr Glu Met Leu Lys Glu Glu His Glu Val Ala Val Leu
            20                  25                  30

Gly Ala Pro His Asn Pro Ala Pro Pro Thr Ser Thr Val Ile His Ile
        35                  40                  45

Arg Ser Glu Thr Ser Val Pro Asp His Val Val Trp Ser Leu Phe Asn
    50                  55                  60

Thr Leu Phe Met Asn Pro Cys Cys Leu Gly Phe Ile Ala Phe Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
            100                 105                 110

Leu Gly Ile Leu Met Thr Ile Leu Leu Ile Val Ile Pro Val Leu Ile
        115                 120                 125

Phe Gln Ala Tyr Gly
    130

<210> SEQ ID NO 47
<211> LENGTH: 11
<212> TYPE: PRT
<213> ORGANISM: Artificial Sequence
<220> FEATURE:
<223> OTHER INFORMATION: Synthetic peptide

<400> SEQUENCE: 47

Arg Ala Ser Glu Asp Leu Tyr Tyr Asn Leu Ala

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Asp Thr Tyr Arg Leu Ala Asp
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Gln Gln Tyr Tyr Lys Phe Pro Phe Thr
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Gly Phe Ser Ser Thr Asn Tyr His Val His
1               5                   10

<210> SEQ ID NO 51
<211> LENGTH: 16
<212> TYPE: PRT
<213> ORGANISM: Artificial Sequence
<220> FEATURE:
<223> OTHER INFORMATION: Synthetic peptide

<400> SEQUENCE: 51

Val Ile Trp Gly Asp Gly Asp Thr Ser Tyr Asn Ser Val Leu Lys Ser
1               5                   10                  15

<210> SEQ ID NO 52
<211> LENGTH: 10
<212> TYPE: PRT
<213> ORGANISM: Artificial Sequence
<220> FEATURE:
<223> OTHER INFORMATION: Synthetic peptide

<400> SEQUENCE: 52

Gln Leu Thr His Tyr Tyr Val Leu Ala Ala
1               5                   10

<210> SEQ ID NO 53
<211> LENGTH: 107
<212> TYPE: PRT
<213> ORGANISM: Artificial Sequence
<220> FEATURE:
<223> OTHER INFORMATION: Synthetic peptide

<400> SEQUENCE: 53

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Glu Asp Leu Tyr Tyr Asn
            20                  25                  30

Leu Ala Trp Tyr Gln Arg Lys Pro Gly Lys Ala Pro Lys Leu Leu Ile
        35                  40                  45

Tyr Asp Thr Tyr Arg Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln Gln Tyr Tyr Lys Phe Pro Phe
                85                  90                  95

Thr Phe Gly Gln Gly Thr Lys Val Glu Ile Lys
                100                 105

<210> SEQ ID NO 54
<211> LENGTH: 117
<212> TYPE: PRT
<213> ORGANISM: Artificial Sequence
<220> FEATURE:
<223> OTHER INFORMATION: Synthetic peptide

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
        35                  40                  45

Gly Val Ile Trp Gly Asp Gly Asp Thr Ser Tyr Asn Ser Val Leu Lys
    50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
                100                 105                 110

Leu Val Thr Val Ser
        115

<210> SEQ ID NO 55
<211> LENGTH: 214
<212> TYPE: PRT
<213> ORGANISM: Artificial Sequence
<220> FEATURE:
<223> OTHER INFORMATION: Synthetic peptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Leu Tyr Tyr Asn
            20                  25                  30

Leu Ala Trp Tyr Gln Arg Lys Pro Gly Lys Ala Pro Lys Leu Leu Ile
        35                  40                  45

Tyr Asp Thr Tyr Arg Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Ser Tyr Tyr Cys Gln Gln Tyr Tyr Lys Phe Pro Phe
```

```
                85                  90                  95
Thr Phe Gly Gln Gly Thr Lys Val Glu Ile Lys Arg Thr Val Ala Ala
                    100                 105                 110
Pro Ser Val Phe Ile Phe Pro Pro Ser Asp Glu Gln Leu Lys Ser Gly
                    115                 120                 125
Thr Ala Ser Val Val Cys Leu Leu Asn Asn Phe Tyr Pro Arg Glu Ala
                    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                    165                 170                 175
Ser Thr Leu Thr Leu Ser Lys Ala Asp Tyr Glu Lys His Lys Val Tyr
                    180                 185                 190
Ala Cys Glu Val Thr His Gln Gly Leu Ser Ser Pro Val Thr Lys Ser
                    195                 200                 205
Phe Asn Arg Gly Glu Cys
                    210

<210> SEQ ID NO 56
<211> LENGTH: 229
<212> TYPE: PRT
<213> ORGANISM: Artificial Sequence
<220> FEATURE:
<223> OTHER INFORMATION: Synthetic peptide

<400> SEQUENCE: 56

Glu Val Gln Leu Val Glu Ser Gly Gly Gly Leu Val Gln Pro Gly Gly
1               5                   10                  15
Ser Leu Arg Leu Ser Cys Ala Val Ser Gly Phe Ser Ser Thr Asn Tyr
                20                  25                  30
His Val His Trp Val Arg Gln Ala Pro Gly Lys Gly Leu Glu Trp Met
                35                  40                  45
Gly Val Ile Trp Gly Asp Gly Asp Thr Ser Tyr Asn Ser Val Leu Lys
    50                  55                  60
Ser Arg Phe Thr Ile Ser Arg Asp Thr Ser Lys Asn Thr Val Tyr Leu
65                  70                  75                  80
Gln Met Asn Ser Leu Arg Ala Glu Asp Thr Ala Val Tyr Tyr Cys Ala
                85                  90                  95
Arg Gln Leu Thr His Tyr Tyr Val Leu Ala Ala Trp Gly Gln Gly Thr
                    100                 105                 110
Leu Val Thr Val Ser Ser Ala Ser Thr Lys Gly Pro Ser Val Phe Pro
                    115                 120                 125
Leu Ala Pro Ser Ser Lys Ser Thr Ser Gly Gly Thr Ala Ala Leu Gly
                    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                    165                 170                 175
Ser Ser Gly Leu Tyr Ser Leu Ser Ser Val Val Thr Val Pro Ser Ser
                    180                 185                 190
Ser Leu Gly Thr Gln Thr Tyr Ile Cys Asn Val Asn His Lys Pro Ser
                    195                 200                 205
Asn Thr Lys Val Asp Lys Lys Val Glu Pro Lys Ser Cys Asp Lys Thr
                    210                 215                 220
His Thr Cys Ala Ala
```

<210> SEQ ID NO 57
<211> LENGTH: 433
<212> TYPE: DNA
<213> ORGANISM: Homo sapiens

<400> SEQUENCE: 57

```
tacaccctgc cccatcccg ggaggagatg accaagaacc aggtcagcct gacctgcctg    60
gtcaaaggct tctacccag cgacatctcc gtggagtggg agagcaatgg gcagccggag   120
aacaactaca agaccacacc tcccatgctg actccgacg gctccttctt cctctacagc   180
aagctcaccg tggacaagag caggtggcag caggggaacg tcttctcatg ctccgtgatg   240
catgaggctc tgcacaacca ctacacacag aagagcctct ccctgtctcc gggtaaatga   300
gtgccacggc cggcaagccc ccgctcccca ggctctcggg gtcgcgcgag gatgcttggc   360
acgtaccccg tctacatact tcccgggcac ccagcatgga aataaagcac ccagcgctgc   420
cctgggcccc tgc                                                      433
```

<210> SEQ ID NO 58
<211> LENGTH: 99
<212> TYPE: PRT
<213> ORGANISM: Homo sapiens

<400> SEQUENCE: 58

```
Tyr Thr Leu Pro Pro Ser Arg Glu Glu Met Thr Lys Asn Gln Val Ser
1               5                   10                  15
Leu Thr Cys Leu Val Lys Gly Phe Tyr Pro Ser Asp Ile Ser Val Glu
            20                  25                  30
Trp Glu Ser Asn Gly Gln Pro Glu Asn Asn Tyr Lys Thr Thr Pro Pro
        35                  40                  45
Met Leu Asp Ser Asp Gly Ser Phe Phe Leu Tyr Ser Lys Leu Thr Val
    50                  55                  60
Asp Lys Ser Arg Trp Gln Gln Gly Asn Val Phe Ser Cys Ser Val Met
65                  70                  75                  80
His Glu Ala Leu His Asn His Tyr Thr Gln Lys Ser Leu Ser Leu Ser
                85                  90                  95
Pro Gly Lys
```

<210> SEQ ID NO 59
<211> LENGTH: 456
<212> TYPE: DNA
<213> ORGANISM: Homo sapiens

<400> SEQUENCE: 59

```
gggcagcccc gagaaccaca ggtgtacacc ctgcccccat cccgggagga gatgaccaag    60
aaccaggtca gcctgacctg cctggtcaaa ggcttctacc ccagcgacat ctccgtggag   120
tgggagagca atgggcagcc ggagaacaac tacaagacca cacctcccat gctggactcc   180
gacggctcct tcttcctcta cagcaagctc accgtggaca gagcaggtg gcagcagggg   240
aacgtcttct catgctccgt gatgcatgag gctctgcaca accactacac acagaagagc   300
ctctccctgt ctccgggtaa atgagtgcca cggccggcaa gccccgctc cccaggctct   360
cggggtcgcg cgaggatgct tggcacgtac ccgtctaca tacttcccgg gcacccagca   420
tggaaataaa gcacccagcg ctgccctggg ccccctg                            456
```

-continued

```
<210> SEQ ID NO 60
<211> LENGTH: 107
<212> TYPE: PRT
<213> ORGANISM: Homo sapiens

<400> SEQUENCE: 60

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ser Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 61
<211> LENGTH: 331
<212> TYPE: DNA
<213> ORGANISM: Homo sapiens

<400> SEQUENCE: 61
cacctgaact cctgggagga ccgtcagtct tcctcttccc cccaaaaccc aaggatacCC    60
ttatgatttc ccggacccct gaggtcacgt gcgtggtggt ggacgtgagc cacgaagacc   120
ccgaggtcca gttcaagtgg tacgtggacg gcgtggaggt gcataatgcc aagacaaagc   180
cgcgggagga gcagtacaac agcacgttcc gtgtggtcag cgtcctcacc gtcctgcacc   240
aggactggct gaacggcaag gagtacaagt gcaaggtctc caacaaagcc ctcccagccc   300
ccatcgagaa aaccatctcc aaaaccaaag g                                  331

<210> SEQ ID NO 62
<211> LENGTH: 109
<212> TYPE: PRT
<213> ORGANISM: Homo sapiens

<400> SEQUENCE: 62

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Lys Trp Tyr Val
        35                  40                  45

Asp Gly Val Glu Val His Asn Ala Lys Thr Lys Pro Arg Glu Glu Gln
    50                  55                  60

Tyr Asn Ser Thr Phe Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Thr Lys
            100                 105

<210> SEQ ID NO 63
```

<211> LENGTH: 396
<212> TYPE: DNA
<213> ORGANISM: Homo sapiens

<400> SEQUENCE: 63

| | | | | | |
|---|---|---|---|---|---|
| ggagctggcc | ctgaacgagc | tggtgacgct | gacgtgcctg | gcacgtggct | tcagccccaa | 60 |
| ggatgtgctg | gttcgctggc | tgcaggggtc | acaggagctg | ccccgcgaga | agtacctgac | 120 |
| ttgggcatcc | cggcaggagc | ccagccaggg | caccaccacc | ttcgctgtga | ccagcatact | 180 |
| gcgcgtggca | gccgaggact | ggaagaaggg | ggacaccttc | tcctgcatgg | tgggccacga | 240 |
| ggccctgccg | ctggccttca | cacagaagac | catcgaccgc | ttggcgggta | aacccaccca | 300 |
| tgtcaatgtg | tctgttgtca | tggcggaggt | ggacggcacc | tgctactgag | ccgcccgcct | 360 |
| gtccccaccc | ctgaataaac | tccatgctcc | cccaag | | | 396 |

<210> SEQ ID NO 64
<211> LENGTH: 115
<212> TYPE: PRT
<213> ORGANISM: Homo sapiens

<400> SEQUENCE: 64

Glu Leu Ala Leu Asn Glu Leu Val Thr Leu Thr Cys Leu Ala Arg Gly
1               5                   10                  15

Phe Ser Pro Lys Asp Val Leu Val Arg Trp Leu Gln Gly Ser Gln Glu
            20                  25                  30

Leu Pro Arg Glu Lys Tyr Leu Thr Trp Ala Ser Arg Gln Glu Pro Ser
        35                  40                  45

Gln Gly Thr Thr Thr Phe Ala Val Thr Ser Ile Leu Arg Val Ala Ala
    50                  55                  60

Glu Asp Trp Lys Lys Gly Asp Thr Phe Ser Cys Met Val Gly His Glu
65                  70                  75                  80

Ala Leu Pro Leu Ala Phe Thr Gln Lys Thr Ile Asp Arg Leu Ala Gly
                85                  90                  95

Lys Pro Thr His Val Asn Val Ser Val Val Met Ala Glu Val Asp Gly
            100                 105                 110

Thr Cys Tyr
        115

<210> SEQ ID NO 65
<211> LENGTH: 360
<212> TYPE: DNA
<213> ORGANISM: Homo sapiens

<400> SEQUENCE: 65

| | | | | | |
|---|---|---|---|---|---|
| tacaccctgc | ccccatcccg | ggaggagatg | accaagaacc | aggtcagcct | gacctgcctg | 60 |
| gtcaaaggct | tctaccccag | cgacatcgcc | gtggagtggg | agagcagcgg | gcagccggag | 120 |
| aacaactaca | acaccacgcc | tcccatgctg | gactccgacg | gctccttctt | cctctacagc | 180 |
| aagctcaccg | tggacaagag | caggtggcag | caggggaaca | tcttctcatg | ctccgtgatg | 240 |
| catgaggctc | tgcacaaccg | cttcacgcag | aagagcctct | ccctgtctcc | gggtaaatga | 300 |
| gtgcgacggc | cggcaagccc | ccgctccccg | ggctctcggg | gtcgcgcgag | gatgcttggc | 360 |

<210> SEQ ID NO 66
<211> LENGTH: 60
<212> TYPE: PRT
<213> ORGANISM: Homo sapiens

<400> SEQUENCE: 66

```
Thr Ala Cys Ala Cys Cys Thr Gly Cys Cys Cys Cys Ala Thr
1               5               10              15

Cys Cys Cys Gly Gly Ala Gly Gly Ala Gly Ala Thr Gly Ala Cys
            20              25              30

Cys Ala Ala Gly Ala Ala Cys Cys Ala Gly Gly Thr Cys Ala Gly Cys
        35                  40                  45

Cys Thr Gly Ala Cys Cys Thr Gly Cys Cys Thr Gly
    50              55              60
```

MOLECULAR SIGNATURES FOR USE IN DIAGNOSIS AND RESPONSE TO TREATMENT ANALYSIS OF AUTOIMMUNE DISEASES

CROSS-REFERENCE TO RELATED APPLICATIONS

This application is the U.S. national stage application of International Patent Application No. PCT/EP2016/073677, filed Oct. 4, 2016, which claims the benefit of U.S. Provisional Patent Application No. 62/237,148, filed Oct. 5, 2015.

The Sequence Listing for this application is labeled "2LY0815.txt" which was created on May 10, 2018, and is 184 KB. The entire content of the sequence listing is incorporated herein by reference in its entirety.

FIELD OF THE INVENTION

The present invention relates to molecular signatures that can be used to identify patients diagnosed with an autoimmune disease, in particular with systemic lupus erythematosus for treatment with a CD40L antagonist such as anti-CD40L antibody or a binding fragment thereof. The present invention further relates to methods of monitoring patients diagnosed with an autoimmune disease, in particular with systemic lupus erythematosus which are undergoing treatment with a CD40L antagonist such as anti-CD40L antibody or a binding fragment thereof.

BACKGROUND OF THE INVENTION

Autoimmune diseases classically comprise more than 80 chronic diseases that affect about 5%-8% of the general population. There has been considerable progress made in understanding the immune system during recent decades, resulting in a better appreciation of the role of costimulatory molecules such as CD40 and its ligand CD154/CD40L which is also known as CD40 Ligand (CD40L). Furthermore, a role for such molecules in the pathogenesis of much commoner diseases such as atherosclerosis is also emerging, which could greatly expand the applicability of therapies targeting this molecule.

CD154/CD40L is expressed on activated T lymphocytes and, through interactions with its receptor CD40, plays a pivotal role in regulating the interplay between T cells and other cell types. The CD154/CD40L-CD40 pair is known to mediate cognate T cell help for B cells, resulting in increased B-cell proliferation and differentiation, antibody production and isotype class switching. CD154/CD40L also promotes the formation of germinal centers in lymph nodes and B-cell survival. CD154/CD40L therefore contributes to the potentiation of autoimmune diseases and holds significant promise as a therapeutic target in autoimmune disease such as systemic lupus erythematosus (SLE), rheumatoid arthritis, ankylosing spondylitis, lupus nephritis, Goodpasture's disease, Sjögren's syndrome, polymyositis, dermatomyositis, psoriasis, temporal arteritis, Churg-Strauss syndrome, multiple sclerosis, Guillain-Barré syndrome, transverse myelitis, myasthenia gravis, Addison's disease, thyroiditis, coeliac disease, ulcerative colitis, sarcoidosis, hemolytic anemia, idiopathic thrombocytopenic purpura, Behçet's disease, primary biliary cirrhosis and autoimmune diabetes, and blockade of CD154/CD40L has been shown to be highly efficacious in several inflammatory and autoimmune model systems. CD154/CD40L has also been suggested to play a role in the inflammatory aspects of atherosclerosis and neurodegenerative disorders.

CD154/CD40L, previously referred to as gp39, TRAP, or TBAM, is a 39 kDa type II membrane glycoprotein of the TNF family. CD154/CD40L is a polypeptide of 261 amino acids, consisting of a 215 amino acids extracellular domain, a 24 amino acids transmembrane region, and a 22 amino acids cytoplasmic tail. Like other members of the TNF-family, CD154/CD40L forms a trimeric structure and promotes as such trimerization of the receptor, namely, CD40. The CD154/CD40L-CD40 interaction is stabilized by charged residues, namely, the basic chains on CD154/CD40L and the acidic ones on CD40.

Hu5c8 (also known as BG-9588, or replizumab), a humanized monoclonal IgG1 antibody against human CD154/CD40L, was evaluated in clinical trials for a range of autoimmune diseases. Results from a phase 2 study in patients with systemic lupus erythematosus (SLE) were encouraging, with significant reductions in disease biomarkers, including circulating levels of autoantibodies, as well as marked increases in C3 levels. However, despite this promising evidence of clinical effect, further development of hu5c8 was discontinued because of an increased incidence of treatment-emergent cardiovascular thrombotic events. Hu5c8 was administered intravenously at a dose of 20 mg/kg given every 2 weeks for three doses, and then every 4 weeks for a further four doses (total seven doses) (Boumpas et al, Arthritis Rheum. 2003 March; 48(3):719-27) The mechanism by which hu5c8 induces thrombotic effects in humans remains unclear, although increased platelet activation has been demonstrated following exposure to hu5c8 in vitro (Meyer et al., Blood (ASH Annual Meeting Abstracts) 2006 108: Abstract 1516).

Systemic lupus erythematosus (SLE) has been classified as an autoimmune disease that may involve many organ systems, as an inflammatory multisystem rheumatic disorder, or as a collagen vascular disease. In Europe and the United States of America, estimates of the number of affected individuals range from 24 to 65 cases per 100,000 population in some studies. Predisposing factors for lupus include Asian or African race, and female gender. 90% of patients with lupus are female and the onset of symptoms usually occurs between the ages of 15 and 50 years. Systemic lupus erythematosus appears not to be a homogeneous disease, but a group of related syndromes, with widely varying presentations, degrees of body system involvement, and clinical course. Clinical features commonly seen in SLE are blood and lymphatic disorders (lymphadenopathy), cardiac disorders (e.g. cardiomyopathy, pericardial effusion, pericarditis), eye disorders (e.g. keratoconjunctivitis sicca), gastrointestinal disorders (e.g. mouth ulceration, pancreatitis, peritonitis, pharyngitis), general disorders (e.g. malaise, fatigue, pyrexia, weight decrease), nervous system disorders (e.g. cerebrovascular accident, cognitive disorder, migraine, headache, peripheral neuropathy), musculoskeletal and connective tissue disorders (e.g. arthralgia, arthritis (not erosive or destructive), fibromyalgia, fracture, myositis, osteonecrosis, osteoporosis, osteopenia), psychiatric disorders (e.g. affective disorder, anxiety, depression, psychosis, neurosis, mental disorder due to a general medical condition, psychotic disorder), renal and urinary disorders (e.g. lupus nephritis, nephrotic syndrome), respiratory, thoracic, and mediastinal disorders (e.g. pleurisy, pneumonitis, pulmonary hypertension), skin and subcutaneous tissue disorders (e.g. alopecia, cutaneous lupus erythematosus, dermatitis, generalized erythema, livedo reticularis, panniculitis, rash maculo-papular, systemic lupus erythematosus rash, urticaria) and vascular disorders (e.g. hypertension, Raynaud's phenomenon, telangiectasis, thrombocytopenia, thrombophlebitis, vasculitis). Additionally, most SLE patients present with abnormal antibody patterns, including the presence of anti-nuclear-(ANA) and anti-double stranded DNA (anti-dsDNA) antibodies.

The clinical course of SLE is episodic, with flares recurring upon increasing underlying disability and organ damage. Corticosteroids are the cornerstone of treatment but are associated with an extensive number of side effects most frequently seen during long-term use. Other drugs used in the setting of lower-level activity include analgesics, non-steroidal anti-inflammatory drugs (NSAIDs), local steroids, and antimalarial drugs (e.g., chloroquine or hydroxychloroquine), with common supportive medications including vasodilators (calcium channel blockers, angiotensin-converting enzyme [ACE] inhibitors) for renal hypertension or Raynaud's syndrome, local treatments for rashes or sicca syndromes, transfusions, intravenous (i.v.) globulin for cytopenias, anticonvulsants, antimigraine medications, anticoagulants for recurrent thromboses, and antidepressants. High-dose corticosteroids, e.g., 0.5 to 1.0 mg/kg/day oral prednisone (or equivalent) or 500 mg to 1 g daily pulse i.v. methylprednisolone, are used to manage acute SLE flares, with immunosuppressants (e.g., azathioprine, cyclophosphamide, methotrexate, mycophenolate mofetil, leflunomide) generally used in moderate and severe cases when other treatments are ineffective or to limit or prevent long-term major organ damage from the disease or corticosteroid use ('steroidsparing'). This present therapeutic armamentarium is inadequate because of limited efficacy and/or adverse events profile. Despite the high medical need for new effective therapies of SLE with good safety profile the development of such therapies has proven to be particularly difficult and many therapeutic candidates have failed. In 2011 belimumab the first drug for the treatment of SLE in 50 years was approved by the FDA, however the proportion of patients that respond to this treatment is relatively low. Furthermore, earlier this year a further candidate, epratuzumab failed a Phase III clinical trial in SLE.

The CD40-CD154/CD40L costimulatory pathway has also been implicated in the pathogenesis of neurodegenerative and neuromuscular disorders and treatment with compounds that interfere with the pathway appear to be useful for treatment of neurodegenerative and neuromuscular disorders (WO 2010/065819, the content of which is incorporated herein in its entirety). Neurodegenerative and neuromuscular disorders include Alzheimers Disease, Parkinson's Disease, amyotrophic lateral sclerosis, myasthenia gravis, multifocal motor neuropathy, primary lateral sclerosis, spinal muscular atrophy, Kennedy's Disease, and spinocerebellar ataxia. Amyotrophic lateral sclerosis (ALS), sometimes called Lou Gehrig's Disease, is a progressive, fatal, neurological disorder characterized by muscle fiber atrophy resulting from the degeneration of motor neurons in the spinal column and brain. ALS affects approximately 30,000 US citizens with only about 10% of the cases being classified as the familial form of ALS. Although ALS is characterized by loss of motor neurons in the spinal cord resulting in muscle atrophy, the disease also manifests itself with changes in axon transport, protein aggregation, excitotoxicity, astrocytosis, mitochondrial dysfunction, microglial activation, and synaptic remodeling. Microglial activation, astrocytosis and the presence of infiltrating inflammatory cells from the periphery has been well described. There is accumulation of IgG immunoreactive deposits in the spinal cord of ALS patients, infiltration of lymphocytes, dendritic cells, monocytes, and macrophages into the spinal cord in ALS. Although the role of infiltrating immune cells is poorly understood, recent work would suggest that infiltrating T cell populations are neuroprotective and not cytotoxic. Although ALS has an immune component mediated by activation of microglia and astrocytes it is not considered to be an autoimmune disorder.

There is a need in the art for new effective treatments of autoimmune, inflammatory, neurodegenerative and neuromuscular disorders. The CD40-CD40L (CD154) interaction pathway has been demonstrated to be relevant for the pathophysiology of autoimmune, inflammatory, neurodegenerative and neuromuscular disorders. A PEGylated anti-CD40L Fab' antibody fragment (CDP7657, also known as dapirolizumab pegol (DZP) is currently in development for inflammatory and autoimmune conditions such as systemic lupus erythematosus. It has been tested in Phase I trials in healthy individuals and patients (Tocoian, A et al., *Lupus* (2015) Vol 24: pages 1045-56).

There is a need for new treatments of autoimmune, inflammatory, neurodegenerative and neuromuscular disorders that block the CD40/CD40L interaction pathway, such as with antibodies or antibody fragments binding specifically to CD154/CD40L or to CD40 administered at a safe and effective dose. There is also a need for methods of identifying patients suffering from autoimmune, inflammatory, neurodegenerative and neuromuscular disorders which will respond to a treatment that targets the CD40/CD40L pathway.

OBJECTIVES AND SUMMARY OF THE INVENTION

It is an objective of the present invention to inter alia provide methods for identifying patients diagnosed with autoimmune, inflammatory, neurodegenerative or neuromuscular disorders which will show an increased likelihood for responding to a treatment that targets the CD40/CD40L pathway. It is another objective of the present invention to provide methods for monitoring patients which are diagnosed with autoimmune, inflammatory, neurodegenerative or neuromuscular disorders and which undergo a treatment that targets the CD40/CD40L pathway with the intention that the results obtained by such monitoring can be used for example for deciding on further development of a drug candidate or therapeutic intervention and/or to indicate early response to treatment and, therefore, whether or not treatment with a disease modifying therapy, e.g., a CD40/CD40L pathway blocker is indicated and/or should be continued because it is of benefit to that subject.

These and other objectives as they will become apparent from the ensuing description hereinafter are attained by the subject matter of the independent claims. Some of the specific aspects and embodiments thereof contemplated by the present disclosure form the subject matter of the dependent claims. Yet other aspects and embodiments thereof as contemplated by the present disclosure may be taken from the ensuing description.

In a first aspect, the disclosure pertains to a method for monitoring treatment of an autoimmune disease in a patient with a CD40 or CD40L antagonist comprising at least the steps of
 a) determining the expression of at least 2 biomarkers as defined in Table 2; the expression of at least 2 biomarkers as defined in Table 3; or the expression of at least 2 biomarkers as defined in Table 4 in a nucleic acid sample obtained from a patient which has been diagnosed with said autoimmune disease, b) determining the expression for said at least 2 biomarkers in a control nucleic acid sample, and deciding on whether said patient responds to treatment with a CD40 or CD40L antagonist by comparing the expression levels determined in steps a) and b), wherein if the level of expression of at least 2 biomarkers as defined in Table 2 or Table 4 is in the control range post treatment with the CD40 of CD40L antagonist it indicates that the patient is responsive to therapy and wherein if the level of expression of at least 2 biomarkers as defined in Table 3 is transiently increased as compared to the control level in the patient prior to therapy it indicates that the patient is responsive to therapy.

In a second aspect, the disclosure pertains to a method for monitoring treatment of an autoimmune disease in a patient with a CD40 or CD40L antagonist comprising at least the steps of a) determining the expression of at least 2 biomarkers as defined in Table 2; and the expression of at least 2 biomarkers as defined in Table 3 in a nucleic acid sample obtained from a patient which has been diagnosed with said autoimmune disease, b) determining the expression for said at least 4 biomarkers in a control nucleic acid sample, and deciding on whether said patient responds to treatment with a CD40 or CD40L antagonist by comparing the expression levels determined in steps a) and b) wherein if the level of expression of at least 2 biomarkers as defined in Table 2 is in the control range post treatment with the CD40 of CD40L antagonist it indicates that the patient is responsive to therapy and wherein if the level of expression of at least 2 biomarkers as defined in Table 3 is transiently increased as compared to the control level in the patient prior to therapy it indicates that the patient is responsive to therapy.

In a third aspect, the disclosure pertains to a method for monitoring treatment of an autoimmune disease in a patient with a CD40 or CD40L antagonist comprising at least the steps of a) determining the expression of at least 2 biomarkers as defined in Table 3; and the expression of at least 2 biomarkers as defined in Table 4 in a nucleic acid sample obtained from a patient which has been diagnosed with said autoimmune disease, b) determining the expression for said at least 4 biomarkers in a control nucleic acid sample, and deciding on whether said patient responds to treatment with a CD40 or CD40L antagonist by comparing the expression levels determined in steps a) and b) wherein if the level of expression of at least 2 biomarkers as defined in Table 4 is in the control range post treatment with the CD40 of CD40L antagonist it indicates that the patient is responsive to therapy and wherein if the level of expression of at least 2 biomarkers as defined in Table 3 is transiently increased as compared to the control level in the patient prior to therapy it indicates that the patient is responsive to therapy.

In a fourth aspect, the disclosure pertains to a method for monitoring treatment of an autoimmune disease in a patient with a CD40 or CD40L antagonist comprising at least the steps of a) determining the expression of at least 2 biomarkers as defined in Table 2; and the expression of at least 2 biomarkers as defined in Table 4 in a nucleic acid sample obtained from a patient which has been diagnosed with said autoimmune disease, b) determining the expression for said at least 4 biomarkers in a control nucleic acid sample, and deciding on whether said patient responds to treatment with a CD40 or CD40L antagonist by comparing the expression levels determined in steps a) and b) wherein if the level of expression of at least 2 biomarkers as defined in Table 2 or Table 4 is in the control range post treatment with the CD40 of CD40L antagonist it indicates that the patient is responsive to therapy.

In a fifth aspect, the disclosure pertains to a method for monitoring treatment of an autoimmune disease in a patient with a CD40 or CD40L antagonist comprising at least the steps of a) determining the expression of a at least 2 biomarkers as defined in Table 2; and the expression of at least 2 biomarkers as defined in Table 3; and the expression of at least 2 biomarkers as defined in Table 4 in a nucleic acid sample obtained from a patient which has been diagnosed with said autoimmune disease, b) determining the expression for said at least 6 biomarkers in a control nucleic acid sample, and deciding on whether said patient responds to treatment with a CD40 or CD40L antagonist by comparing the expression levels determined in steps a) and b) wherein if the level of expression of at least 2 biomarkers as defined in Table 2 or Table 4 is in the control range post treatment with the CD40 of CD40L antagonist it indicates that the patient is responsive to therapy and wherein if the level of expression of at least 2 biomarkers as defined in Table 3 is transiently increased as compared to the control level in the patient prior to therapy it indicates that the patient is responsive to therapy.

In one embodiment of these aspects, the disclosure contemplates to preferably determine the expression of at least 3, 4, 5, 6 or 7 biomarkers as defined in Table 2; the expression of at least 3, 4, or 5 biomarkers as defined in Table 3; and/or the expression of at least 3, or 4 biomarker as defined in Table 4 depending on which aspect the respective method refers to.

For all embodiments of the first to fifth aspect, the disclosure considers that an at least transient decrease of the expression of at least 2, 3, 4, 5, 6 or 7 biomarkers as defined in Table 2 is indicative of a response to treatment by the CD40 or CD40L antagonist; that an at least transient increase of the expression of at least 2, 3, 4, or 5 biomarkers as defined in Table 3 is indicative of a favorable response to treatment (i.e., target engagement) by the CD40 or CD40L antagonist; and that an at least transient decrease of the expression of at least 2, 3, or 4 biomarkers as defined in Table 4 is indicative of a response to treatment by the CD40 or CD40L antagonist. Such transient increased or decreased expression, i.e., expression that is increased or decreased for a duration of between 1 to 20 weeks can be measured at any point within about 1 to about 20 weeks after start of treatment.

In a sixth aspect, the present disclosure contemplates to use methods for monitoring in accordance with the first to fifth aspect including the embodiments thereof for guiding treatment of an autoimmune disease in a patient with a CD40 or CD40L antagonist. During treatment with a CD40 or CD40L antagonist expression of biomarkers of Table 2, Table 3, and/or Table 4 can be monitored as described for the first to fifth aspect hereinafter and on the basis of the results it can then be decided whether treatment with the CD40 or CD40L antagonist is continued or discontinued.

In a seventh aspect, the disclosure pertains to a method of identifying a patient suffering from an autoimmune disease likely to benefit from therapy with a CD40 or CD40L antagonist, comprising at least the steps:
  a) determining the expression of at least one biomarker as defined in Table 1; or the expression of at least one biomarker as defined in Table 5; in a nucleic acid sample obtained from a patient which has been diagnosed with said autoimmune disease,
  b) determining the expression for said at least one biomarker in a control nucleic acid sample, and
deciding on whether said patient responds to treatment with a CD40 or CD40L antagonist by comparing the expression levels determined in steps a) and b) wherein if the level of expression of at least 1 biomarker as defined in Table 1 or Table 5 is higher than that of a control (e.g., a non-responder patient) prior to therapy it indicates that the patient is likely to be responsive to therapy.

In an eighth aspect, the disclosure pertains to a method of identifying a patient suffering from an autoimmune disease likely to benefit from a therapy with a CD40 or CD40L antagonist, comprising at least the steps:
  a) determining the expression of at least one biomarker as defined in Table 1; and the expression of at least one biomarker as defined in Table 5 in a nucleic acid sample obtained from a patient which has been diagnosed with said autoimmune disease,
  b) determining the expression for said at least one biomarker in a control nucleic acid sample, and
  c) deciding on whether said patient will respond with an increased likelihood to treatment with a CD40 or CD40L antagonist by comparing the expression levels determined in steps a) and b) wherein if the level of expression of at least 1 biomarker as defined in Table 1 or Table 5 is higher than that of a control (e.g., a non-responder patient) prior to therapy it indicates that the patient is likely to be responsive to therapy.

In one embodiment of this seventh and eighth aspect, the disclosure contemplates to preferably determine the expression of at least 1, 2, 3, 4, or 5 biomarkers as defined in Table 1; and/or the expression of at least 1, 2, 3, 4, 5, 6, 7, 8, 9 or 10 biomarkers as defined in Table 5 depending on which aspect the respective method refers to.

For all embodiments of the seventh and eighth aspect, the disclosure considers that an increased or higher level of expression at baseline (prior to treatment) of at least 1, 2, 3, 4, or 5 biomarkers as defined in Table 1 as compared to a control non-responder or a healthy volunteer sample indicates that a patient will show a clinical response to treatment with a CD40 or CD40L antagonist with a higher likelihood than a patient which shows a level of expression essentially the same as that seen in a non-responder control; similarly the disclosure considers that an increased or higher level of expression at baseline of at least 1, 2, 3, 4, 6, 7, 8, 9 or 10 biomarkers as defined in Table 5 as compared to a control non-responder or a healthy volunteer sample indicates that a patient will show a clinical response to treatment with a CD40 or CD40L antagonist with a higher likelihood than a patient which shows a level of expression essentially the same as a healthy or non-responder control.

For all embodiments of the first to eighth, the disclosure preferably considers patients suffering from systemic lupus erythematosus. Systemic lupus erythematosus may have been diagnosed in such patients according to the American College of Rheumatology classification criteria (Ines, L. et al., *Arthritis Care & Research* (2015), 67 (8), 1180-1185).

Another ninth aspect of the disclosure relates to a group of biomarkers for use in identifying patients suffering from systemic lupus erythematosus eligible for treatment with a CD40 or CD40L antagonist comprising 1, 2, 3, 4, or 5 biomarkers of Table 1; and/or 1, 2, 3, 4, 5, 6, 7, 8, 9 or 10 biomarkers of Table 5. Systemic lupus erythematosus may have been diagnosed in such patients according to the American College of Rheumatology classification criteria.

For all embodiments of the first to ninth aspect, the change in expression of sample is referenced to expression of the respective biomarkers in control samples. Such control samples may reflect expression levels of the respective biomarkers in healthy subjects or in patients which have also been diagnosed with the respective autoimmune disease such as SLE and are known to be responders to treatment with anti-CD40 pathway antagonists (known responder controls) or are known to be non-responders to treatment with anti-CD40 antagonists (known non-responder controls). Such samples are particularly useful when measuring the level of expression of a biomarker in a patient prior to treatment to determine whether their expression levels are higher or lower than a suitable control.

In another embodiment, control samples reflect the expression levels of the respective biomarkers in patients which have also been diagnosed with the respective autoimmune disease such as SLE but which show a different expression profile either before the onset of treatment or which receive no therapeutically active substance or which receive placebo. Such control samples are particularly suited to measurement of biomarkers in Tables 2 and 3 and are used as controls when patient samples are being tested for the ability of an antagonist to inhibit the pathway.

A change in expression may be considered to occur if the difference in expression vs the control sample is at least about 30%, at least about 40%, at least about 50%, at least about 60%, at least about 80%, at least about 100%, at least about 200%, at least about 300% or even more pronounced. Among the afore-mentioned values, changes of at least about 200% or more are preferred.

In a tenth aspect, the present disclosure relates to a CD40 or CD40L antagonist for use in treating a patient suffering from an autoimmune disease by administering to said patient a CD40 or CD40L antagonist and
  a) wherein said patient has been subject to any of the methods according to the seventh or eighth aspect and their embodiments, or
  b) wherein said patient is subject to any of the methods according to first to fifth aspect and their embodiments.

In an eleventh aspect, the present disclosure relates to a CD40 or CD40L antagonist for use in treating a patient suffering from an autoimmune disease by administering to said patient a CD40 or CD40L antagonist and
  a) wherein said patient has been subject to any of the methods according to the seventh or eighth aspect and their embodiments, and
  b) wherein said patient is subject to any of the methods according to first to fifth aspect and their embodiments.

In a twelfth aspect, the present disclosure relates to a kit, diagnostic composition or device for conducting any of the methods of the first to eighth aspects and their embodiments comprising at least primers and/or probes selective for determining the expression of any of the biomarkers of Tables 1, 2, 3, 4, or 5 and optionally a CD40 or CD40L antagonist.

For all embodiments of the first to twelfth aspect, the disclosure preferably considers anti-CD40L antibodies or binding fragments thereof as CD40L antagonist and most preferably the PEGylated anti-CD40L antibody fragment CDP7657.

For all embodiments of the first to twelfth aspect, the disclosure preferably considers anti-CD40 antibodies or binding fragments thereof as CD40 antagonist.

In all embodiments of all aspects described herein the sample can be outside the human or animal body.

FIGURE LEGENDS

FIG. 1: Illustration of how significance of changes in molecular signatures were identified. Individual genes were grouped together at a 'Functional level' based upon their cell of origin or their biological function e.g. plasma cells, B-cells, interferon (IFN)-responsive genes. This approach was then used to enable the identification of 'consistent patterns' over the profiles, and to ignore isolated, but statistically significant, effects. Expression levels for each gene following CDP7657 or placebo treatment were compared at each time point to baseline. Then the difference in fold change (FC) between treated and placebo groups was evaluated for statistical significance. Nominally statistically-significant P-values of <0.0894 were highlighted. The P-value of 0.0894 was derived in order to achieve a 5% false positive rate across each of the functional groups. Colored p-values indicate a statistically significant change in expression as described in Example 1.

FIG. 2: Plasma cell genes: depiction of the arithmetic mean (+/−SEM) of log fold change of expression from baseline during the 12 week treatment period. Upper line is Placebo group, lower line is CDP7657 treated group.

Figure 3:
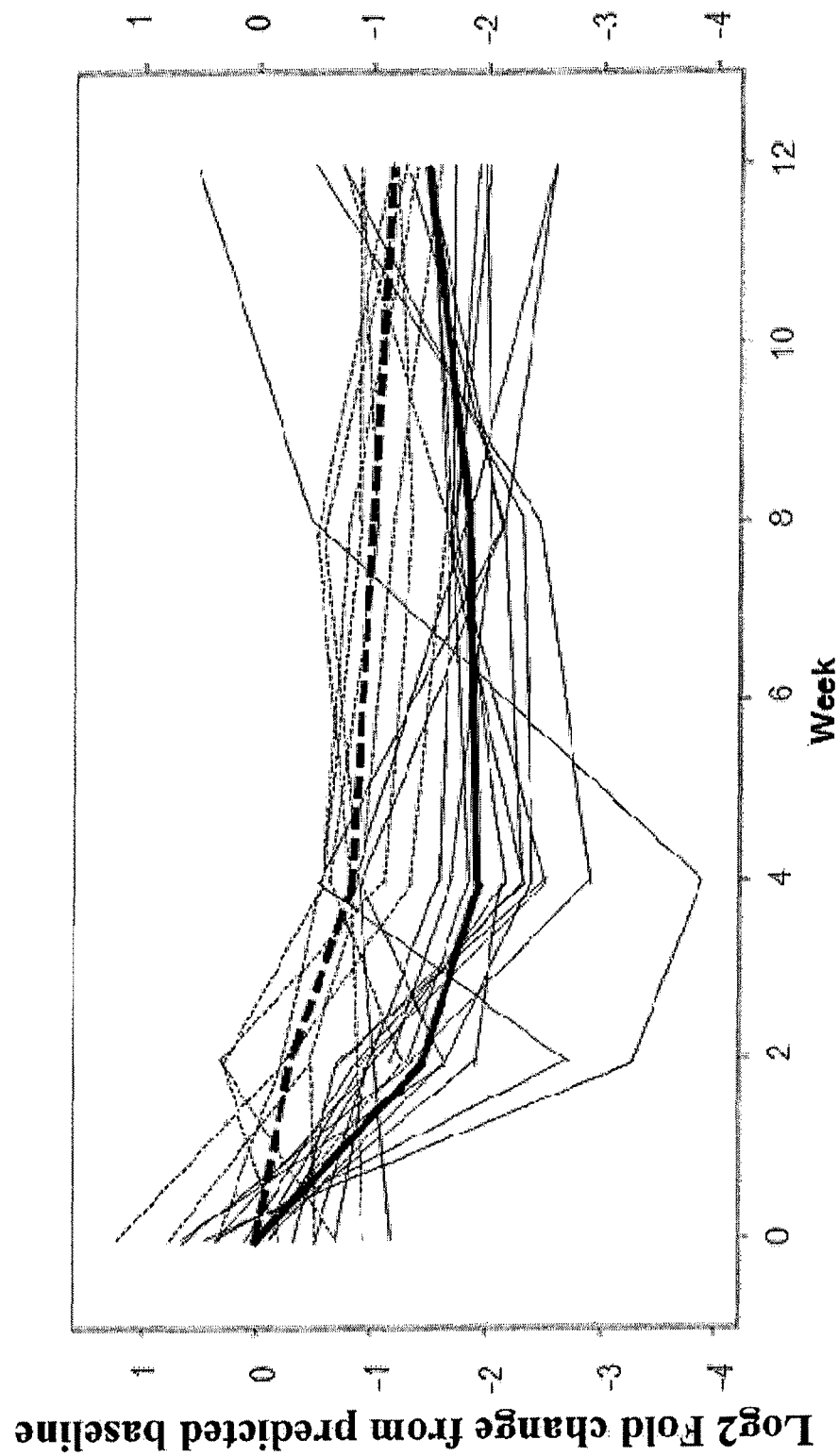

FIG. 3: Plasma cell signature (Table 2) was determined by consensus clustering: illustration of the average log 2 fold change (PC) of expression from predicted baseline for 7 plasma cell genes during 12 week treatment. Thick solid line indicates CDP7657. Thick dashed line indicates placebo. Individual subjects are indicated with narrow solid (treated) and dashed (placebo) lines.

Figure 4:
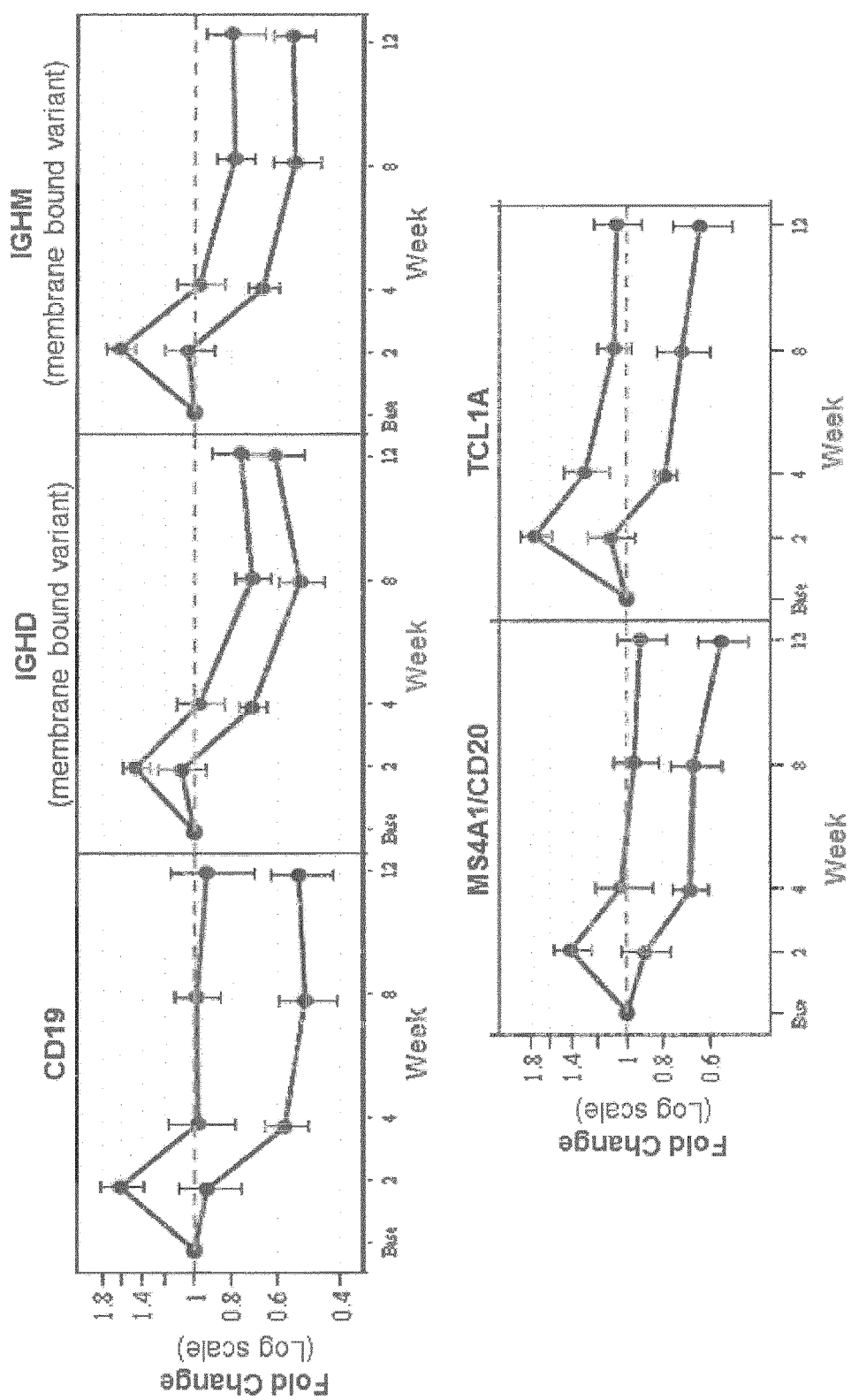

FIG. 4: B cell genes: depiction of the arithmetic mean (+/−SEM) of log fold change of expression from baseline during the 12 week treatment period. Lower line is placebo, upper line is CDP7657.

Figure 5:
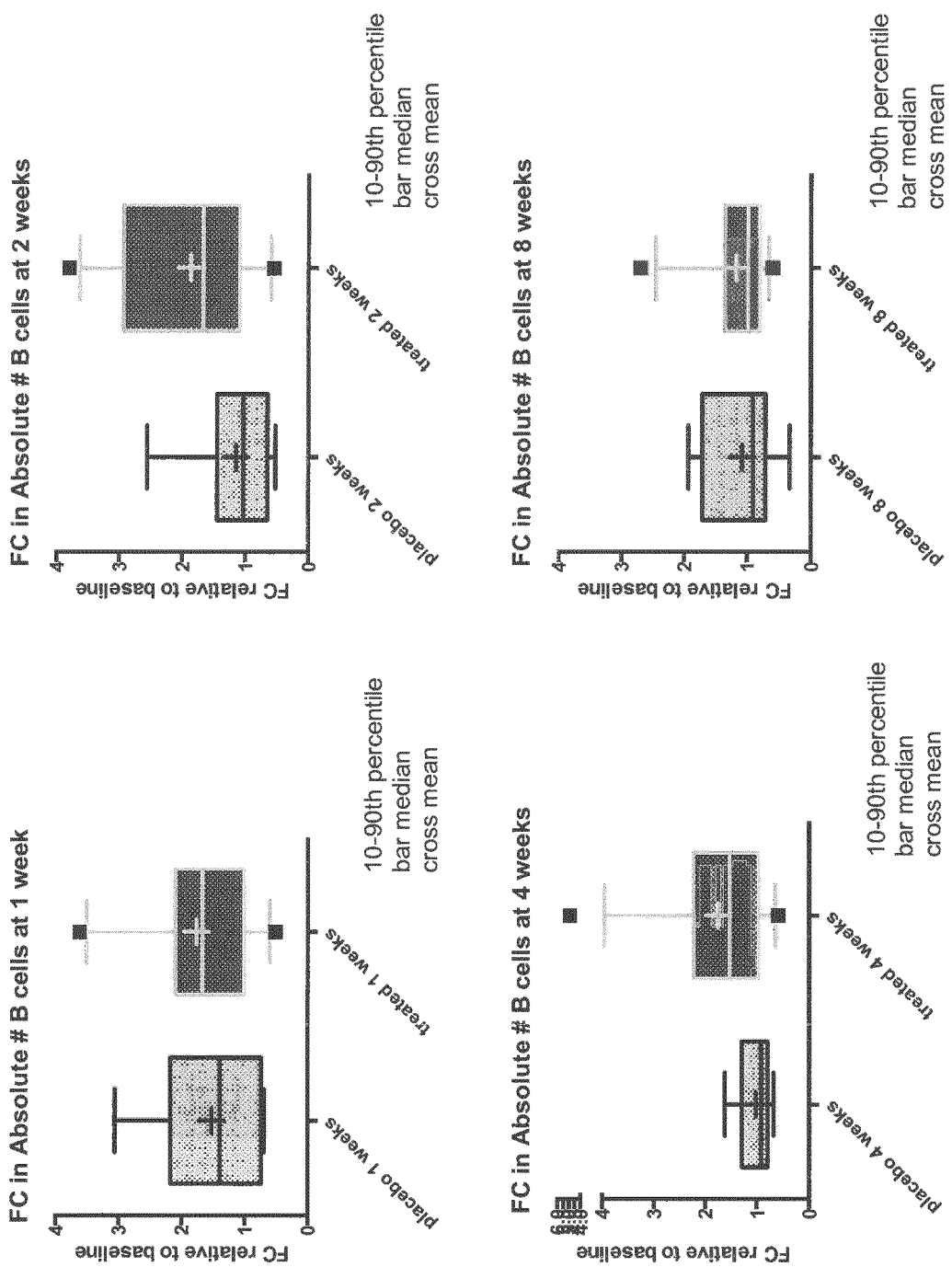

FIG. 5: B cell numbers: depicts fold change (FC) from baseline in absolute B cell number in blood at week 1, 2, 4, and 8.

Figure 6:
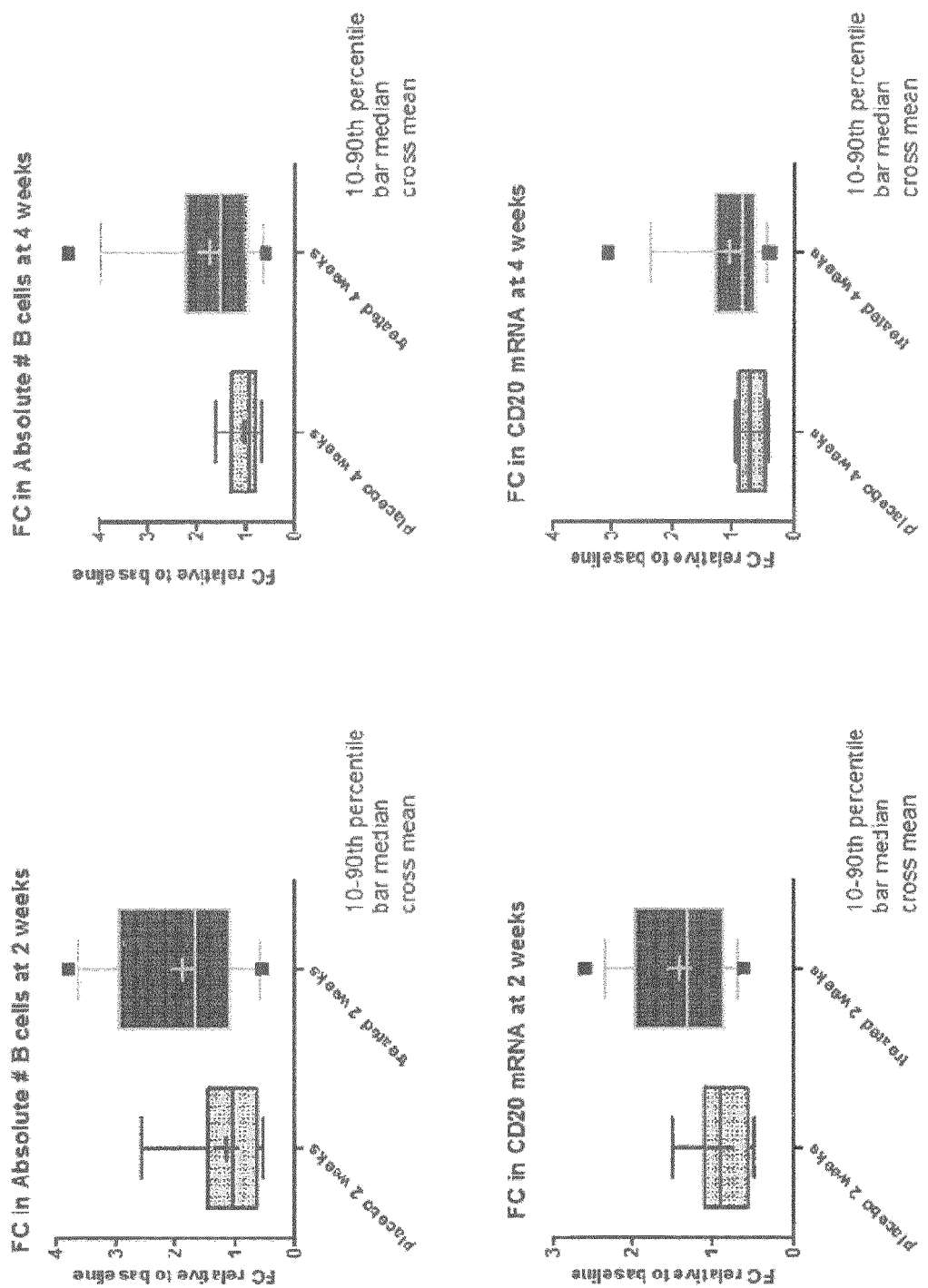

FIG. 6: Correlation of changes in B cell numbers with CD20 (MS4A1) RNA: depicts fold change (PC) in absolute B cell number (#) at week 2 and 4 and fold change (FC) of CD20 transcript level (CD20 mRNA) at weeks 2 and 4 relative to baseline.

Figure 7:
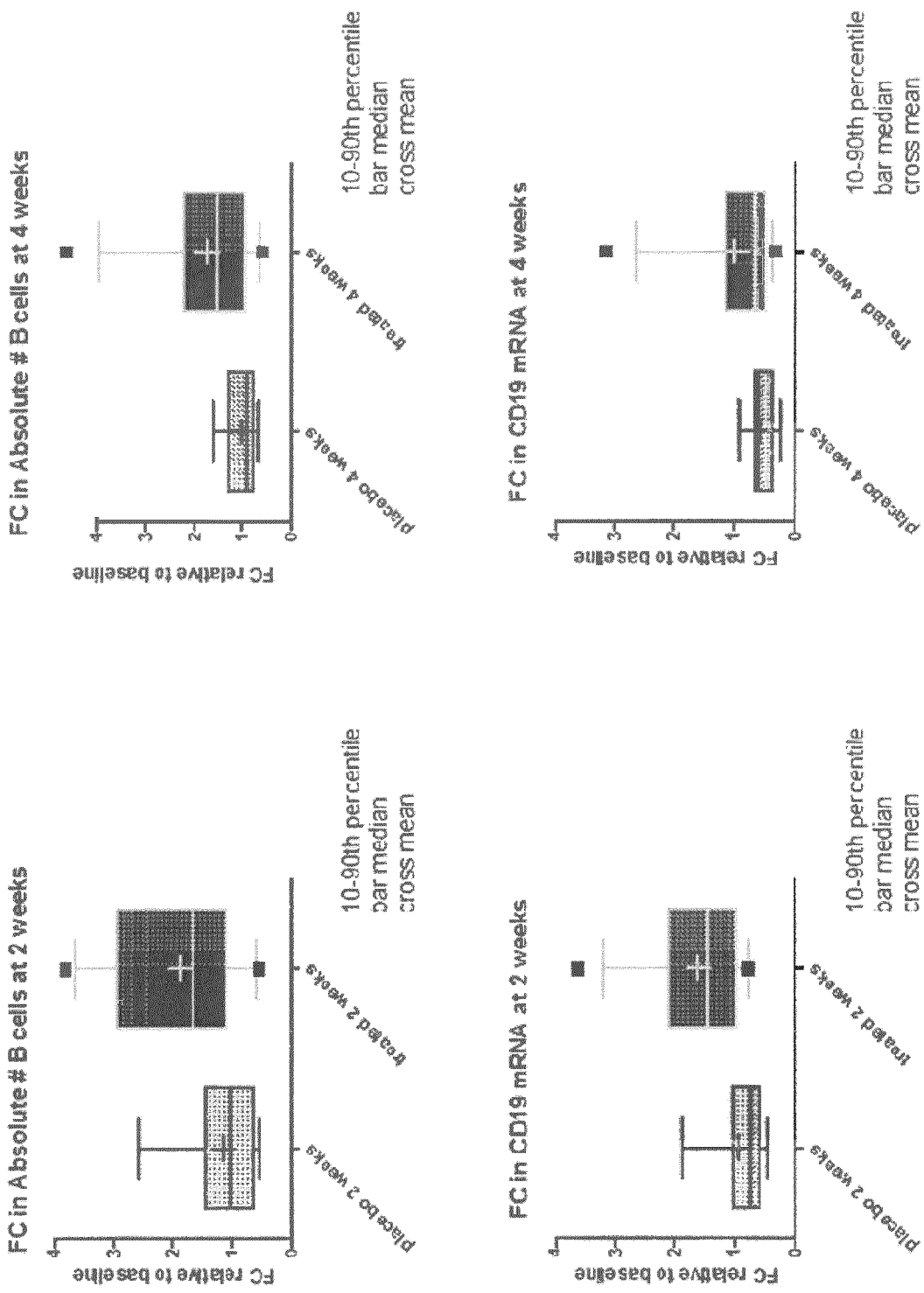

FIG. 7: Correlation of changes in B cell numbers with CD19 RNA: depicts fold change (FC) in absolute B cell number (#) and fold change (FC) of CD19 transcript level (CD19) at weeks 2 and 4 relative to baseline.

Figure 8:
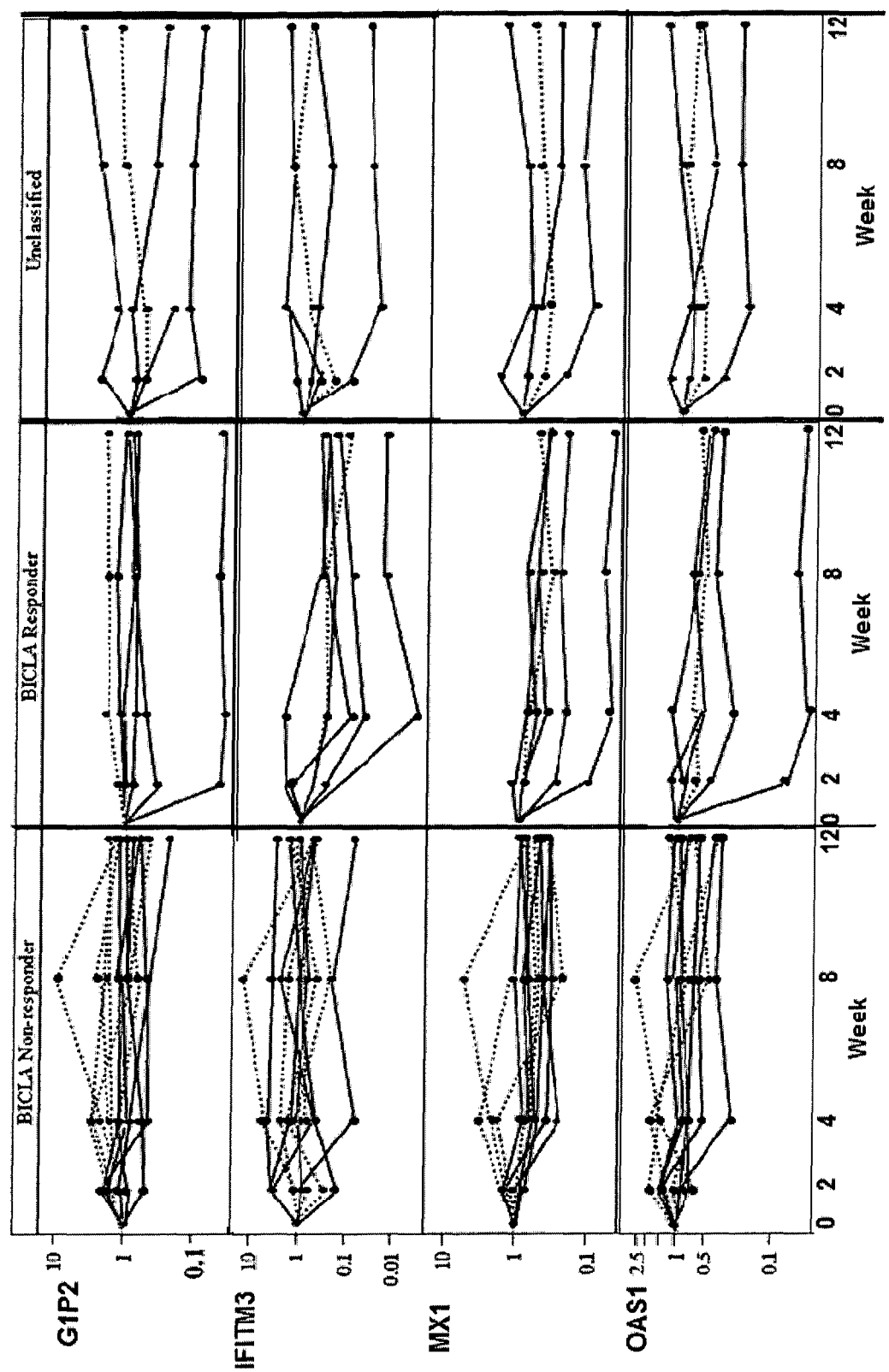

FIG. 8: Interferon response genes: depicts changes of expression from baseline of interferon-responsive genes for each individual stratified by clinical response criteria during the 12 week treatment period. Dark solid line is Placebo, and the light line is CDP7657 treated. In some patients it was not possible to determine a BICLA score (unclassified).

Figure 9:
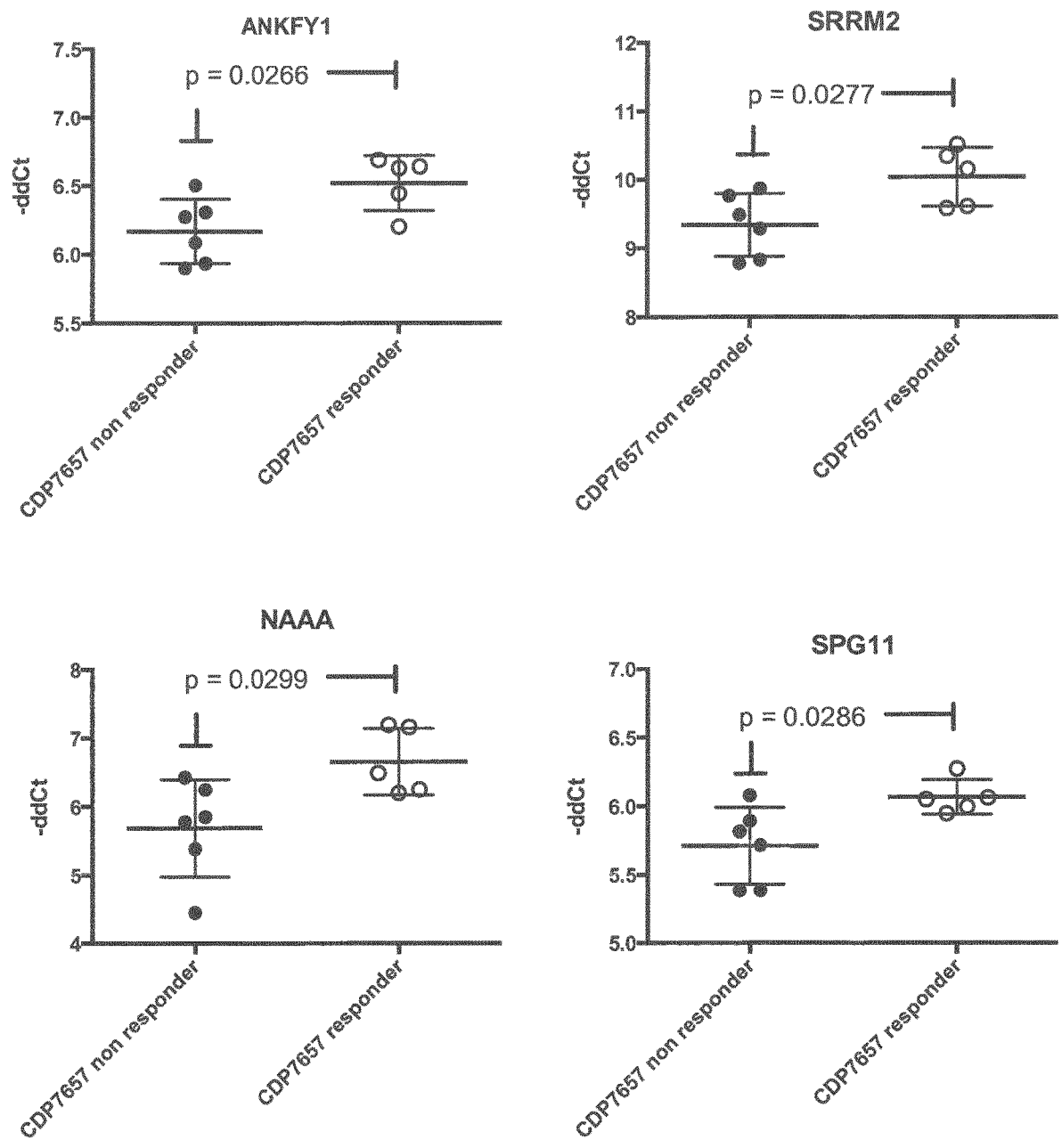

FIG. 9: Baseline predictors of clinical response: depicts difference in expression levels before treatment in patients which were treated with CDP7657 and which were classified as BICLA responders or non-responders. In some patients it was not possible to determine a BICLA score (unclassified).

Figure 10:
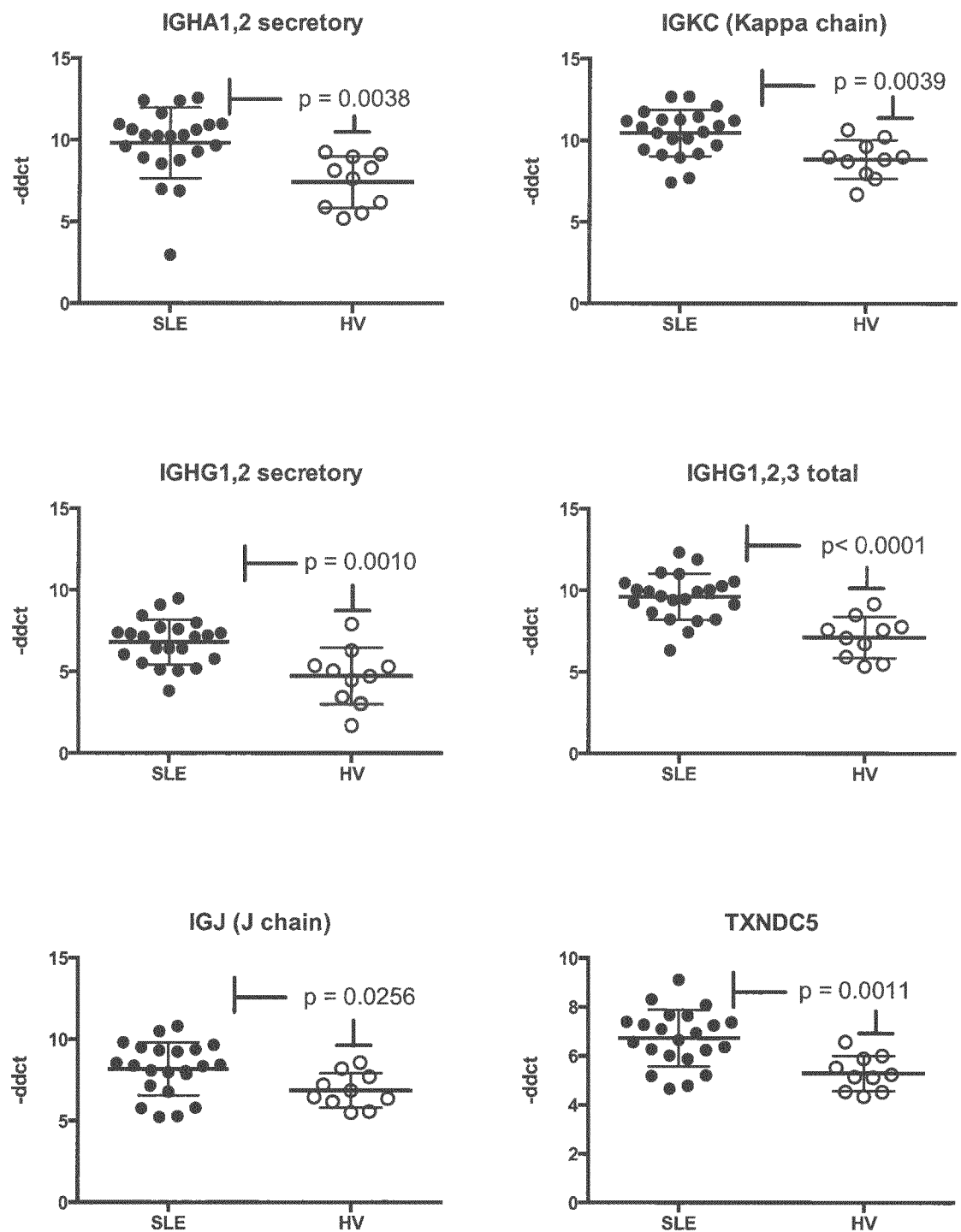
Figure 10:
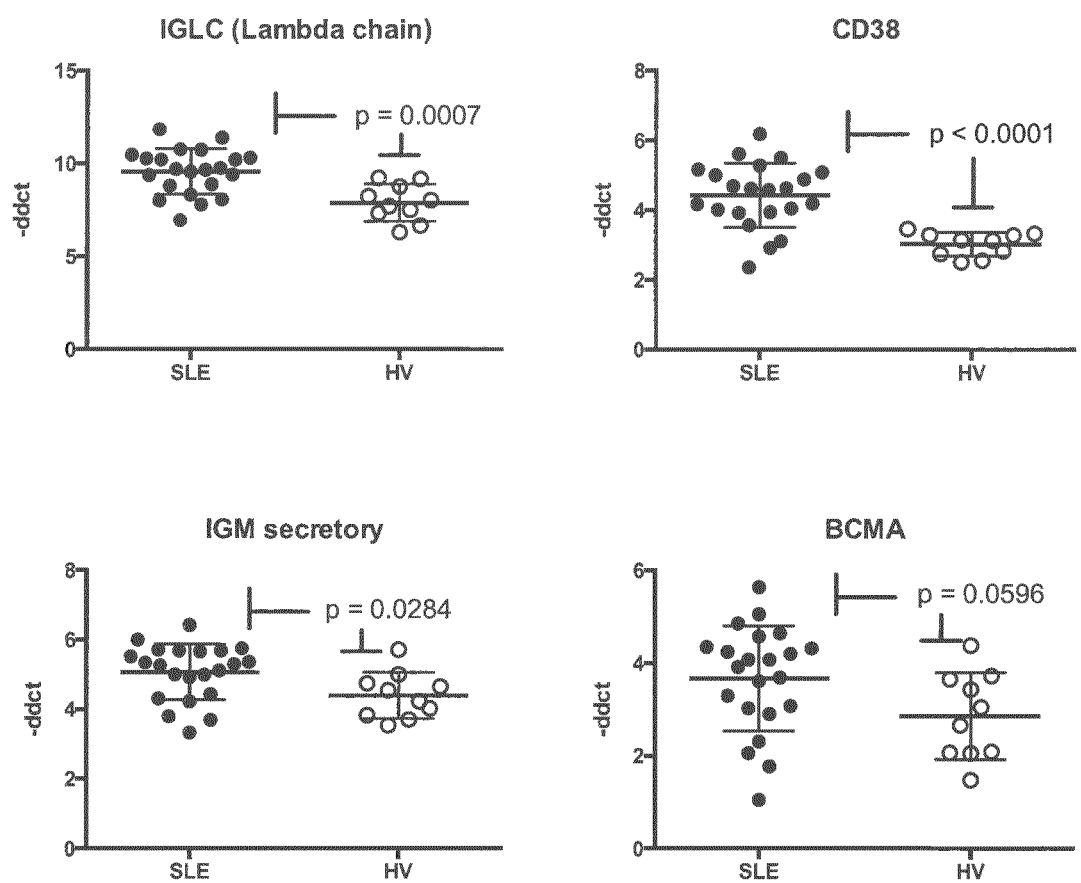

FIG. 10: Elevation in plasma cell genes in SLE subjects at baseline relative to HV: depicts difference in expression levels before treatment in patients (SLE) vs healthy volunteers (HV). P value derived by unpaired t-test.

Figure 11:
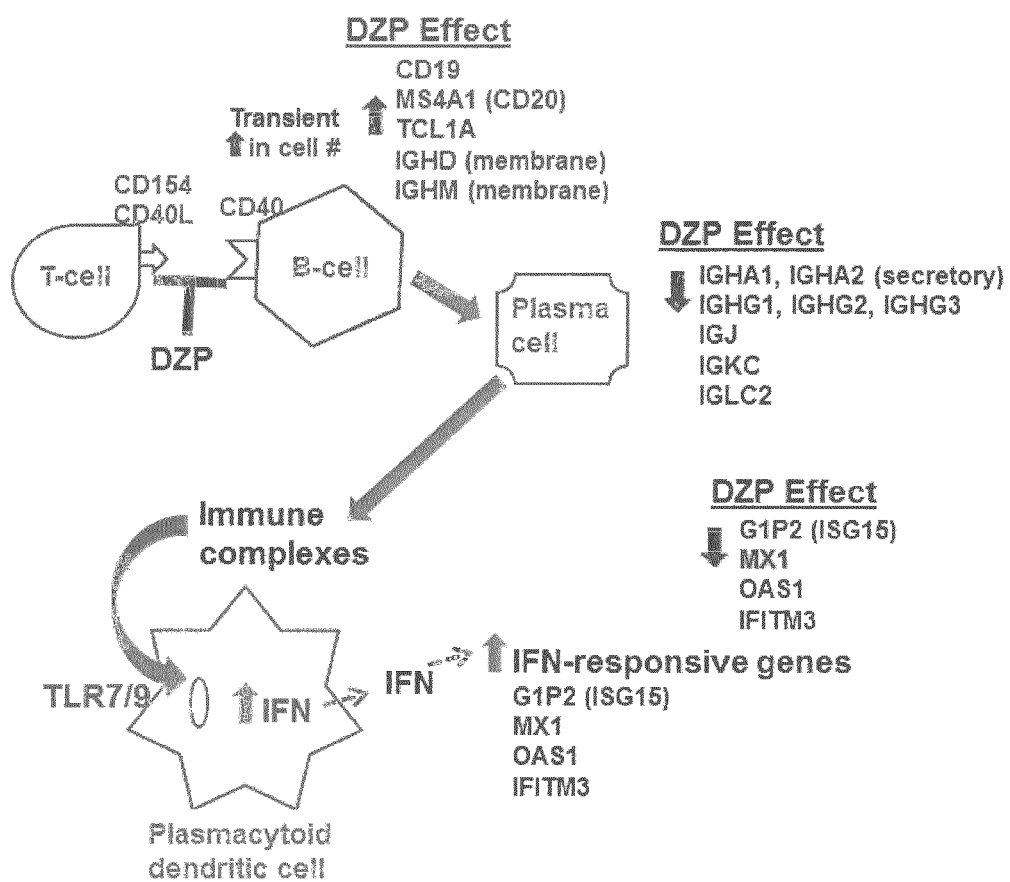

FIG. 11: schematic categorization of observed effects.

DETAILED DESCRIPTION OF THE INVENTION

The following summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. The present disclosure as illustratively described in the following may suitably be practiced in the absence of any element or elements, limitation or limitations, not specifically disclosed herein.

Technical terms are used by their common sense unless indicated otherwise. If a specific meaning is conveyed to certain terms, definitions of terms will be given in the following in the context of which the terms are used.

Where the term "comprising" is used in the present description and claims, it does not exclude other elements. For the purposes of the present disclosure, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

The terms "about" or "approximately" denote an interval of accuracy that the person skilled in the art will understand to still ensure the technical effect of the feature in question. The term typically indicates deviation from the indicated numerical value of ±10%, and preferably of ±5%. Where the term "about" is used the application also discloses employing the exact value specified. Where point values are referred to, the application also discloses about such values being employed, the same being the case for endpoints of ranges.

As used herein, the terms "treatment", "treating" and the like, refer to obtaining a desired pharmacologic and/or physiologic effect. The effect may therapeutic in terms of a partial or complete cure for a disease and/or adverse effect attributable to the disease. Treatment thus covers any treatment of a disease in a mammal, particularly in a human, and includes inhibiting the disease, i.e., arresting its development; and relieving the disease, i.e., causing regression of the disease.

A "therapeutically effective amount" refers to the amount of a CD40 or CD40L antagonist such as anti-CD40 or anti-CD40L antibodies or binding fragments thereof that, when administered to a mammal or other subject for treating a disease, is sufficient to effect such treatment for the disease. The therapeutically effective amount will vary depending on the CD40 or CD40L antagonist such as anti-CD40 or anti-CD40L antibodies or binding fragments thereof the disease and its severity and the age, weight, etc., of the subject to be treated.

The term "antibody" or "antibodies" as used herein, refers to immunoglobulin molecules typically comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. A heavy chain constant region can also have a fourth constant domain, CH4. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino terminus to carboxy-terminus in the following order FR1, CDR1, FR2, CDR2, FR3, CDR3, FR4. The exact boundaries of these CDRs have been defined differently according to different systems. The system described by Kabat not only provides an unambiguous residue numbering system applicable to any variable region of an antibody, but also provides precise residue boundaries defining the three CDRs. These CDRs may be referred to as Kabat CDRs. Chothia et al. found that certain sub-portions within Kabat CDRs adopt nearly identical peptide backbone conformations, despite having great diversity at the level of amino acid sequence (Chothia et al. (1987) Mol. Biol. 196:901-917; Chothia et al. (1989) Nature 342:877-883). These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 62(5):732-45. Still other CDR boundary definitions may not strictly follow one of the herein described systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. The term immunoglobulin or immunoglobulins is used synonymously with "antibody" or "antibodies", respectively. The term "antibody" or "antibodies" as used herein includes but is not limited to recombinant antibodies that are generated by recombinant technologies as known in the art. An "antibody" or "antibodies" can be of any origin including from mammalian species such as human, non-human primate (e.g. human such as from chimpanzee, baboon, rhesus or cynomolgus monkey), rodent (e.g. from mouse, rat, rabbit or guinea pig), goat, bovine or horse species; or of bird species such as chicken antibodies or of fish species such as shark antibodies. "Antibody" or "antibodies" include antibodies' of any isotype, including human isotypes IgA1, IgA2, IgD, IgG1, IgG2a, IgG2b, IgG3, IgG4, IgE and IgM and modified variants thereof. The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens are also contemplated. Where the antigen is a polypeptide, it may be a transmembrane molecule (e.g. receptor) or ligand such as a growth factor or cytokine.

The term "antibody fragment" or "antibody fragments" as used herein, refers to a naturally occurring antibody which lacks one or more domains or one or more amino acids. Typically, antibody fragment contains the entire antigen binding or variable region thereof of such naturally occurring antibody. Examples of antibody fragments include any antibody that has no Fc portion. Examples of antibody fragments include also Fab, Fab', F(ab), Fv and scFv fragments, Fab-Fv, Fab-dsFv, Fab-scFv, Fab-scFc, disulphide stabilised Fab-scFv, scFv, scFv-scFc, dsscFv, dsscFv-scFc; diabodies; triabodies; tetrabodies; minibodies; antibodies consisting essentially of a single, two or three immunoglobulin domain(s) such as Domain Antibodies™; single-chain antibodies, VHH and VNAR fragments; bispecific, trispecific, tetraspecific or multispecific variants of any of the above (see for example Holliger and Hudson, 2005, Nature Biotech. 23(9):1126-1136; Adair and Lawson, 2005, Drug Design Reviews—Online 2(3), 209-217). The term "antibody fragment" or "antibody fragments" as used herein also refers to camelid antibodies (e.g. from camels or llamas such as Nanobodies™) and derivatives thereof. Antibodies fragments are well known in the art (Holliger and Hudson, 2005). Various techniques have been developed for the production of antibody fragments and are known in the art (Glover and Humphreys, 2004). The Fab-Fv format was first disclosed in WO2009/040562 and the disulphide stabilised versions thereof, the Fab-dsFv was first disclosed in WO2010/035012. A disulphide stabilized form of Fab-scFv was described in WO2013/068571. Antibody formats comprising scFc formats were first described in WO2008/012543. Other antibody fragments for use in the present invention include the Fab and Fab' fragments described in International patent applications WO2005/003169, WO2005/003170 and WO2005/003171. Multi-valent antibodies may comprise multiple specificities e.g. bispecific or may be monospecific (see for example WO92/22583 and WO05/113605). One such example of the latter is a Tri-Fab (or TFM) as described in WO92/22583.

The term "antibody fragment" or "antibody fragments" as used herein, comprises human, humanized, primatized and chimeric antibody fragments.

The term "CD40 antagonist" as used herein refers to a compound which is able to interfere with the CD40L-CD40 signaling pathway. It can include small inhibitory molecules, siRNAs, antisense RNA, etc. Anti-CD40 antibodies or binding fragments thereof are preferred CD40 antagonists.

The term "anti-CD40 antibody", as used herein (or an "antibody that neutralized CD40 activity"), is intended to refer to an antibody whose binding to CD40 results in attenuation, such as for example a 50% reduction of activity, or inhibition of the biological activity of CD40. This inhibition of the biological activity of CD40 can be assessed by measuring one or more indicators of CD40 biological activity. These indicators of CD40 biological activity can be assessed by one or more of several standard in vitro or in vivo assays known in the art. Examples of anti-CD40 antibodies are available in the art, such as for example lucatumumab currently under clinical development in multiple myeloma.

The term "CD40L antagonist" as used herein refers to a compound which is able to interfere with the CD40L-CD40 signaling pathway. It can include small inhibitory molecules, siRNAs, antisense RNA, etc. Anti-CD40L antibodies or binding fragments thereof are preferred CD40L antagonists.

The term "anti-CD40L antibody", as used herein (or an "antibody that neutralized CD40L activity"), is intended to refer to an antibody whose binding to CD40L results in attenuation, such as for example a 50% reduction of activity, or inhibition of the biological activity of CD40L. This inhibition of the biological activity of CD40L can be assessed by measuring one or more indicators of CD40L biological activity. These indicators of CD40L biological activity can be assessed by one or more of several standard in vitro or in vivo assays known in the art. For example, in vitro assays could measure the capacity of antibodies to inhibit the binding of a purified CD40 protein to CD40L-expressing cells or cell lines or an assay of T-cell-dependent B-cell activation, involving co-culture of CD40L-expressing T-cell or T-cell line with B cells or a B cell line and monitoring intercellular adhesion molecule 1 (ICAM-1) expression on the latter cells. In vivo assays could include investigating the immune response to an antigen such as tetanus toxin or keyhole limpet hemocyanin in a suitable species such as the non-human primate if the antibody recognizes this species or in mice if the antibody recognizes this species. If the antibody does recognize mouse CD40L, then it could be assessed in a mouse model of SLE such as the NZB/W or MRL/1pr mice. Such antibodies are also designated as neutralizing antibodies.

An anti-CD40L antibody or binding fragment thereof may have a dissociation constant for monovalent binding to CD40L of $K_D \leq 4.55$ pM or lower such as $\leq 4$ pM, $\leq 3$ pM, or $\leq 2$ pM. The term "KD", as used herein, is intended to refer to the dissociation constant of a particular antibody-antigen interaction. The dissociation constant can refer to monovalent binding or bivalent binding. Preferably, the dissociation constant is determined by surface plasmon resonance. The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnsson, B., et al. (1991) Anal. Biochem. 198:268-277.

One anti-CD40L antibody which is most preferred throughout all aspects and embodiments described hereinafter unless otherwise indicated is CDP7657 which is also designated as dapirolizumab pegol or DZP. It is to be understood that CD7657 is a PEGylated Fab' antibody fragment.

The term "PEGylation", "polyethylene glycol" or "PEG", as used herein, refers to the attachment, e.g. through covalent bonding, of a polyalkylene glycol compound or a derivative thereof, with or without coupling agents or derivatization with coupling or activating moieties (e.g., with thiol, triflate, tresylate, azirdine, oxirane, or preferably with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types: dextran, colominic acids, or other carbohydrate based polymers, polymers of amino acids, and biotin and other affinity reagent derivatives.

CDP7657 is disclosed in WO 2008/118356 (incorporated herein in its entirety). CDP7657 has a light chain variable region (LCVR) with the CDR1, CDR2 and CDR3 having the amino acid sequence of SEQ ID NOs: 47, 48 and 49, respectively, and a heavy chain variable region (HCVR) with the CDR1, CDR2 and CDR3 having the amino acid sequence of SEQ ID NOs: 50, 51 and 52, respectively. CDP7657 has the VL chain sequence shown in SEQ ID NO: 53 and the VH chain sequence shown in SEQ ID NO: 54 CDP7657 has the light chain sequence shown in SEQ ID NO: 55 and the heavy chain sequences shown in SEQ ID NO: 56. CDP7657 is PEGylated at a cysteine in the modified hinge region as described in WO 2008/118356. A maleimide group is covalently linked to a single thiol group in a cysteine in the modified hinge region; a lysine residue is covalently linked to the maleimide group; and a methoxy-poly(ethyleneglycol) polymer having a molecular weight of approximately 20 KDa is attached to each of the amine groups on the lysine residue. The total molecular weight of the entire PEG covalently linked to the monovalent Fab' is therefore approximately 40 KDa.

Alternatively said anti-CD40L antibody fragment is a Fab-Fv format, wherein said Fab binds CD40L and has a light chain variable region (LCVR) with the CDR1, CDR2 and CDR3 having the amino acid sequence of SEQ ID NOs: 47, 48 and 49, respectively, and a heavy chain variable region (HCVR) with the CDR1, CDR2 and CDR3 having the amino acid sequence of SEQ ID NOs: 50, 51 and 52, respectively. In a further embodiment said Fab binds CD40L and has the VL chain sequence shown in SEQ ID NO: 53 and the VH chain sequence shown in SEQ ID NO: 54, alternatively said Fab binds CD40L and has the light chain sequence shown in SEQ ID NO: 55 and the heavy chain sequences shown in SEQ ID NO: 56. In a further particular embodiment said anti-CD40L FabFv has a Fv region that binds serum albumin.

Whenever reference is made to an anti-CD40L antibody or binding fragment thereof, this thus preferably refers to an isolated anti-CD40L antibody or binding fragment thereof; wherein said anti-CD40L antibody or binding fragment thereof comprises a light chain variable region comprising a CDR1 selected from SEQ ID No.: 47 or sequences at least 90% identical thereto, a CDR2 selected from SEQ ID No.: 48 or sequences at least 90% identical thereto, and a CDR3 selected from SEQ ID No.: 49 or sequences at least 90% identical thereto; and/or a heavy chain variable region comprising a CDR1 selected from SEQ ID No.: 50 or sequences at least 90% identical thereto, a CDR2 selected from SEQ ID No.: 51 or sequences at least 90% identical thereto, and/or a CDR3 selected from SEQ ID No.: 52 or sequences at least 90% identical thereto.

"Identity", as used herein, indicates that at any particular position in the aligned sequences, the amino acid residue is identical between the sequences. Degrees of Identity can be readily calculated e.g. using the BLAST™ software available from NCBI (Altschul, S. F. et al., 1990, J. Mol. Biol. 215:403-410; Gish, W & States, D. J. 1993, Nature Genet. 3.266-272. Madden, T. L. et al., 1996, Meth. Enzymol. 266:131-141; Altschul, S. F. et al., 1997, Nucleic Acids Res. 25:3389-3402; Zhang, J. k Madden, T. L. 1997, Genome Res. 7:649-656).

The identity of CDRL1, CDRL2, CDRL3, CDRH1, CDRH2, and CDRH3 to SEQ ID Nos.: 47, 48, 49, 50, 51, and 52 respectively may be at least 90%, but may also be higher such as at least 95%, 96%, 97%, 98% or 99% with an optional preference for higher identities. Positions of different identity may be selected according to similarity considerations.

An anti-CD40L antibody or binding fragment thereof may also comprise a light chain variable region comprising SEQ ID No.: 53 or sequences at least 80% identical thereto, and/or a heavy chain variable region comprising SEQ ID No.: 54 or sequences at least 80% identical thereto.

The identity of VL and VH to SEQ ID Nos.: 53 and 54 respectively may be at least 80%, but may also be higher such as at least 80%, 85%, 90%, 95%, 96%, 97%, 98% or 99% with an optional preference for higher identities. Positions of different identity may be selected according to similarity considerations. It will be appreciated that in term of identity there may be more flexibility for the framework regions vs. the CDRs.

An anti-CD40L antibody or binding fragment thereof may also comprise a light chain comprising SEQ ID No.: 55 or sequences at least 70% identical thereto, and/or a heavy chain comprising SEQ ID No.: 56 or sequences at least 70% identical thereto.

The identity of the light chain and heavy chain to SEQ ID Nos.: 55 and 56 respectively may be at least 70%, but may also be higher such as at least 70%, 75%, 80%, 85%, 90%, 95%, 96%, 97%, 98% or 99% with an optional preference for higher identities. Positions of different identity may be selected according to similarity considerations. It will be appreciated that in terms of identity there may be more flexibility for the framework regions vs. the CDRs and even more flexibility for the constant regions.

The above described anti-CD40L antibodies or binding fragments thereof can be PEGylated (as defined by CDRs, variable regions or complete chain sequences) at a cysteine in the modified hinge region, as for described in WO 2008/118356. For example, a maleimide group can be covalently linked to a single thiol group in a cysteine in the modified hinge region; a lysine residue can then be covalently linked to the maleimide group; and a methoxypoly(ethyleneglycol) polymer having a molecular weight of approximately 20 KDa can be attached to each of the amine groups on the lysine residue. The total molecular weight of the entire PEG covalently linked to the anti-CD40L antibody or binding fragment thereof is thus approximately 40 KDa.

Antibodies will preferably be monoclonal antibodies or binding fragments thereof.

The term "BILAG index" or "BILAG score" as used herein, refers to the British Isles Lupus Assessment Group score and index, respectively (Symmons D P et al. Q J Med. 1988 November; 69(259):927-37). The BILAG index was used to assess efficacy of treatment in patients with SLE in study SL0007. It is a comprehensive index for measuring SLE disease activity. The 2004 version of the BILAG index was used for the studies. This version consists of 86 questions in 8 body systems (general, mucocutaneous, neurological, musculoskeletal, cardiovascular and respiratory, vasculitis, renal, and hematological). Some of the questions were based on the patient's history, some on examination findings, and others on laboratory results. Each body system score ranges from E to A, with A being the most severe disease activity. The interpretation of body system scores are as follows: A ("Active")=severely active disease (sufficient to require disease-modifying treatment, for example, greater than 20 mg/day of prednisone, immunosuppressants, cytoxics); B ("Beware")=moderately active disease (requires only symptomatic therapy, for example, less than or equal to 20 mg/day of prednisone or antimalarial drugs; C ("Contentment")=mild stable disease (no indication for changes in treatment); D=previously active disease—but none currently; E=no prior disease activity. When the BILAG alphabetic organ body system scores are converted to numeric values and summed (using the rule where each BILAG A=9, each BILAG B=3, each BILAG C=1, and each BILAG D or E is worth 0), this is referred to as a Total BILAG score.

The term "SLEDAI score" or "SLEDAI" index refers to the Systemic Lupus Erythematosus Disease Activity score/index, respectively (Hawker et al., J Rheumatol. 1993).

The term "SRI score" or "SRI" index refers to the Systemic Lupus Erythematosus Responder Indexscore/index (Furie R A et al., Arthritis Rheum. 2009).

The term "BICLA" is a BILAG-based Combined Lupus Assessment (BICLA) composite endpoint (Wallace at al, Arthritis Rheum 2011; 63 (S10):S885).

BICLA was developed based on input from an expert panel that evaluated the characteristics of disease activity indices (DAIs) commonly used in SLE trials and previous experience with DAIs.

It requires patients to meet response criteria across three assessment tools:

(1) the BILAG-2004 index (2) the SLEDAI index and (3) a physician's global assessment (PGA).

BICLA responders must achieve BILAG disease activity improvement across all eight body systems with no worsening in BILAG or other disease activity indexes at the same time point, and no treatment failure at any time point.

A clinical phase I study (SL0014) was performed with CDP7657 in serologically-positive patients afflicted with systemic lupus erythematosus (SLE), see Example 1 for details. During the study ribonucleic acid samples were taken from whole blood, and expression of genes analyzed.

This analysis revealed that the following group of genes shows an increase at baseline in SLE patients which were classified as BICLA clinical responders to treatment with CDP7657 after 12 weeks (see also FIG. 9) compared to BICLA non-responders to treatment with CDP7657:

TABLE 1

| No | Gene | Genbank ID/ Ensembl ID (where Genbank unavailable) | nucleic acid sequence (SEQ ID No) | amino acid sequence (SEQ ID No) |
| --- | --- | --- | --- | --- |
| 1 | ANKFY1 | NM_016376 | 1 | 2 |
| 2 | SRRM2 | NM_016333 | 3 | 4 |
| 3 | SPG11 | NM_025137 | 5 | 6 |
| 4 | NAAA | NM_014435 | 7 | 8 |
| 5 | NAA20 | NM_016100 | 9 | 10 |

Therefore, in one embodiment, the invention pertains to a method of predicting the ability of a subject having an autoimmune disease (e.g., SLE) to respond to treatment with an agent that blocks the CD40/CD40L pathway (e.g., CDP7657) by measuring the expression of at least one of ANKYF1, SRRM2, SPG11, NAAA, or NAA20 and comparing that level of expression with a suitable control. If the level of expression of one or more of these genes in the subject is higher than the level in the control sample, the subject is identified as one that is likely to respond to treatment with the agent that blocks the CD40/CD40L pathway. In one embodiment, the patient so identified is treated with the agent (e.g., CDP7657) at an effective dose, e.g., as described herein.

The analysis also revealed that the following group of plasma cell related genes shows a decreased expression in SLE patients being treated with CDP7657 vs Placebo (see also FIGS. 2 and 3):

TABLE 2

| No | Gene | Genbank ID/Ensembl ID (where Genbank unavailable) | nucleic acid sequence (SEQ ID No) | amino acid sequence (SEQ ID No) |
|---|---|---|---|---|
| 1 | IGHA1 secretory | CHR_HSCHR14_3_CTG1 | 11 | 12 |
| 2 | IGHG1 total | chromosome:GRCh38:14 | 21 | 22 |
| 3 | IGHG1 secretory | chromosome:GRCh38:14 | 13 | 14 |
| 4 | IGJ | NM_144646 | 15 | 16 |
| 5 | IGKC | AH002839S3 | 17 | 18 |
| 6 | IGLC2 | HUMIGLCB2 | 19 | 20 |
| 7 | TXNDC5 | NM_030810 | 23 | 24 |

It is pointed out that the primer-based RT-PCR approach which was chosen to detect changes in expression following administration of CDP7657 (see example section) did not differentiate between IGHA1 secretory (see Table 2, SEQ ID No: 11 and 12) or IGHA2 secretory (Genbank symbol: CHR_HSCHR14_3_CTG1, SEQ ID No: 63 and 64). Thus, a change in expression of IGHA1 secretory may also indicate a change in expression of IGHA2 secretory and whenever reference is made in the context of this disclosure to a change in expression of IGHA1 secretory this is understood to refer a change in expression of IGHA2 secretory as well.

Similarly, the primer-based RT-PCR approach which was chosen to detect changes in expression following administration of CDP7657 (see example section) with IGHG1_total primers was designed to detect transcript levels from IGHG1, IGHG2 and IGHG3. Thus, it did not differentiate between IGHG1 secretory (see Table 2, SEQ ID No: 13 and 14) or IGHG2 secretory (Genbank symbol: CHR_HSCHR14_3_CTG1, SEQ ID No: 57 and 58), IGHG3 secretory (SEQ ID No.:65 and 66), or membrane bound forms thereof. Thus, a change in expression of for example secretory IGHG1 may also result in a change in expression of IGHG1 total, although a change in total IGHG1 would not necessarily indicate a change in IGHG1 secretory and whenever reference is made in the context of this disclosure to a change in expression of IGHG1 total, this is understood to refer a change in expression IGHG1 total, of IGHG2 total and IGHG3 total as well. The sequences provided in SEQ ID No. 21, SEQ ID No.: 59 and SEQ ID No.: 61 encompass the exon from which primer sets were selected for amplification of RNAs representing IGHG1 total, IGHG2 total and IGHG3 total, respectively.

Similarly, the primer-based RT-PCR approach which was chosen to detect changes in expression following administration of CDP7657 (see example section) with IGHG1_Secretory primers did not differentiate between IGHG1 secretory (see Table 2, SEQ ID No: 13 and 14) and IGHG2 secretory (Genbank symbol: CHR_HSCHR14_3_CTG1, SEQ ID No: 57 and 58. Thus, a change in expression of secretory IGHG1 may also indicate a change in expression of secretory IGHG2.

The analysis also revealed that the following group of B cell related genes shows a transient increased expression in SLE patients being treated with CDP7657 vs Placebo (see also FIG. 4):

TABLE 3

| No | Gene | Genbank ID/Ensembl ID (where Genbank unavailable) | nucleic acid sequence (SEQ ID No) | amino acid sequence (SEQ ID No) |
|---|---|---|---|---|
| 1 | CD19 | NM_001178098 | 30 | 31 |
| 2 | IGHD membrane | CHR_HSCHR14_3_CTG1 | 32 | 33 |
| 3 | IGHM membrane | CHR_HSCHR14_3_CTG1 | 34 | |
| 4 | MS4A1 (CD20) | NM_152866 | 35 | 36 |
| 5 | TCL1A | NM_021966 | 37 | 38 |

The analysis also revealed that the following group of interferon (IFN) related genes shows a decreased expression in SLE patients being treated with CDP7657 versus placebo and showing some clinical response (see also FIG. 8):

TABLE 4

| No | Gene | Genbank ID/Ensembl ID (where Genbank unavailable) | nucleic acid sequence (SEQ ID No) | amino acid sequence (SEQ ID No) |
|---|---|---|---|---|
| 1 | G1P2 | NM_005101 | 39 | 40 |
| 2 | MXI | NM_001144925 | 41 | 42 |
| 3 | OAS1 | NM_016816 | 43 | 44 |
| 4 | IFITM3 | JQ610601 | 45 | 46 |

The analysis also revealed that the following group of plasma cell related genes shows an increased expression in SLE patients vs healthy volunteers before treatment (see also FIG. 10):

TABLE 5

| No | Gene | Genbank ID/Ensembl ID (where Genbank unavailable) | nucleic acid sequence (SEQ ID No) | amino acid sequence (SEQ ID No) |
|---|---|---|---|---|
| 1 | IGHA1 secretory | CHR_HSCHR14_3_CTG1 | 11 | 12 |
| 2 | IGHG1 total | chromosome:GRCh38:14 | 21 | 22 |
| 3 | IGHG1 secretory | chromosome:GRCh38:14 | 13 | 14 |
| 4 | IGJ | NM_144646 | 15 | 16 |
| 5 | IGKC | AH002839S3 | 17 | 18 |
| 6 | IGLC2 | HUMIGLCB2 | 19 | 20 |
| 7 | TXNDC5 | NM_030810 | 23 | 24 |
| 8 | IGM secretory | CHR_HSCHR14_3_CTG1 | 25 | |
| 9 | CD38 | D84276 | 26 | 27 |
| 10 | BCMA | AB052772 | 28 | 29 |

These findings open the door for various applications in the context of treatment for autoimmune disease such as systemic lupus erythematosus (SLE).

For example, the group of genes which may also be referred to as signatures of biomarkers which are shown in Table 2, 3, and 4 show a change of expression as a consequence of treatment with an anti-CD40L antibody or binding fragment thereof, namely CDP7657. For example, the genes of the plasma cell signature, i.e. genes of Table 2 are down regulated within two to four weeks after treatment. The genes of the B cell signature, i.e. genes of Table 3 are transiently up regulated within two to four weeks after treatment commences. The genes of the IFN-responsive signature, i.e. genes of Table 4 show a decreased expression throughout twelve weeks after treatment commences.

These data also show that the group of genes which may also be referred to as signatures of biomarkers which are shown in Table 1 and 5 are expressed at a higher level at baseline (prior to treatment) in patients that are likely to respond to treatment with an anti-CD40L antibody or binding fragment thereof namely CDP7657 than is the case in subjects that are non-responders to treatment with an anti-CD40L antibody.

If one is developing a CD40 or CD40L antagonist for use in treating autoimmune diseases such as SLE, one can thus use these biomarkers for testing early on whether the compound in question actually engages the target, CD40 or CD40L, in a manner suggestive of potential efficacy. One may thus start a trial with such a putative CD40 or CD40L antagonist and check whether any or all of the biomarkers of the plasma cell signature, i.e. Table 2 are down-regulated within the first four weeks after treatment commences. Similarly one may start a trial with such a putative CD40 or CD40L antagonist and check whether any or all of the biomarker of the B cell signature, i.e. Table 3 are transiently up-regulated within the first four weeks after treatment commences. If such effects occur this can be taken as an indication of proper target engagement and the trial can be continued and the CD40 or CD40L antagonist and the compound can be further developed. If not, one may stop the trial early on. Given that the genes of the IFN signature, i.e. Table 4 seem to be down regulated over the course of treatment in patients which show a clinical response, some or all of these genes may be used to check whether a CD40 or CD40L antagonist is effective in patients. Depending on the outcome of the analysis one may thus continue treatment (if there is a reduced expression of genes of Table 4) or stop treatment if this was not the case.

In a first aspect, the disclosure thus pertains to a method for monitoring treatment of an autoimmune disease in a patient with a CD40 or CD40L antagonist comprising at least the steps of
  a) determining the expression of at least 2 biomarkers as defined in Table 2; the expression of at least 2 biomarkers as defined in Table 3; or the expression of at least 2 biomarkers as defined in Table 4 in a nucleic acid sample obtained from a patient which has been diagnosed with said autoimmune disease,
  b) determining the expression for said at least 2 biomarkers in a control nucleic acid sample, and
  c) deciding on whether said patient responds to treatment with a CD40 or CD40L antagonist by comparing the expression levels determined in steps a) and b).

The results of such monitoring may be used for running and evaluating clinical trials of CD40 or CD40L antagonists such as anti-CD40 or anti-CD40L antibodies or binding fragments thereof or guiding treatment with CD40 or CD40L antagonists such as anti-CD40 or anti-CD40L antibodies or binding fragments thereof as described above.

The reliability of the results of such methods of monitoring and guiding therapy will generally increase with the number of genes analyzed within a biomarker signature. It is therefore preferred to determine the expression of at least 3, 4, 5, 6 or 7 biomarkers as defined in Table 2; the expression of at least 3, 4, or 5 biomarkers as defined in Table 3; and/or the expression of at least 3, or 4 biomarkers as defined in Table 4. In general it is preferred to determine the expression of all genes within the signatures of Tables 2, 3, or 4. However, as regards the plasma cell signature determining expression for no. 1 to 5 of Table 2 may already be sufficient. Similarly for the IFN signature determining expression for no. 1 to 3 of Table 4 may already be sufficient.

The disclosure considers that an at least transient decrease of the expression of at least 2, 3, 4, 5, 6 or 7 biomarkers as defined in Table 2 is indicative of a response to treatment by the CD40 or CD40L antagonist; that an at least transient increase of the expression of at least 2, 3, 4, or 5 biomarkers as defined in Table 3 is indicative of a response to treatment by the CD40 or CD40L antagonist; and that an at least transient decrease of the expression of at least 2, 3, or 4 biomarkers as defined in Table 4 is indicative of a response to treatment by the CD40 or CD40L antagonist.

Such increased or decreased expression is to be measured within about 1 to about 20 weeks after start of treatment such as within about 1 to about 16 weeks after start of treatment. Depending on which biomarkers are analyzed, measurement may preferably take place within about 1 to about 12 weeks after start of treatment.

If one considers the biomarkers of Table 2, a decrease in expression could indicate target engagement as early as about 1 to about 6 weeks such as about 2 to about 4 weeks. Similarly if one considers the biomarkers of Table 3, a transient increase in expression could indicate target engagement as early as about 1 to about 6 weeks such as about 2 to about 4 weeks. Thus, these biomarkers could be used to decide early on and well before a clinical response would be detected whether treatment should continue or not. Alternatively or additionally, a decrease in expression of biomarkers of Table 4 could indicate target engagement and even first signs of clinical response over a treatment period of about 12 weeks or longer.

Such monitoring may take place at selected time points after treatment commences such as 2 weeks, 4 weeks, 6 weeks, 8 weeks, 12 weeks, 16 weeks or 20 weeks or it may be performed over parts of or the entire duration of administration.

The change in expression in a subject prior to and after treatment or the difference in expression between that seen in a patient sample and that seen in a suitable control are both referenced to expression of the respective biomarkers in control samples. For all aspects and embodiments thereof as they form part of the present disclosure such control samples may reflect expression levels of the respective biomarkers in healthy subjects or in patients which have also been diagnosed with the respective auto-immune disease such as SLE and for whom responsiveness or non-responsiveness status has been determined. In one embodiment, control samples reflect the expression levels of the respective biomarkers in patients which have also been diagnosed with the respective auto-immune disease such as SLE but which show a different expression profile either before the onset of treatment or which receive no therapeutically active substance substances, e.g. which receive placebo.

In one embodiment, relative to the first to fifth aspect, expression levels are referenced to expression levels of control samples from patients which have been diagnosed with the respective auto-immune disease such as SLE and which receive no treatment at all or receive placebo treatment.

The analytical or predictive strengths of the methods of monitoring and guiding therapy as mentioned above not only determines the signatures of Table 2, Table 3, or Table 4, but measures the expression levels for these signatures in combination, e.g. the signatures of Table 2 and 3, of Table 2 and 4, of Table 3 and 4, or of Table 2, 3, and 4. In general, one will focus on signatures of Table 2 (plasma cell markers) and/or Table 3 (B cell markers) if one is particularly interested in an early read out while one may consider the signature of Table 4 (IFN responsive markers) if one wants to monitor the entire trial and/or is additionally interested in clinical response effects.

As an example, the fifth aspect as mentioned above pertains to a method for monitoring treatment of an autoimmune disease in a patient with a CD40 or CD40L antagonist comprising at least the steps of
- a) determining the expression of at least 2 biomarkers as defined in Table 2; and the expression of at least 2 biomarkers as defined in Table 3; and the expression of at least 2 biomarkers as defined in Table 4 in a nucleic acid sample obtained from a patient which has been diagnosed with said autoimmune disease,
- b) determining the expression for said at least 6 biomarkers in a control nucleic acid sample, and
- c) deciding on whether said patient responds to treatment with a CD40 or CD40L antagonist by comparing the expression levels determined in steps a) and b).

Samples may be from patients which have been diagnosed with the respective auto-immune disease and which receive no treatment at all or receive placebo treatment. The respective autoimmune disease may be SLE.

As pointed out in the context of the first aspect, the analytical or predictive force of the results may increase the more genes are analyzed for each group with one embodiment considering that all genes within each group, i.e. all genes of Tables 2, 3, and 4 are analyzed. However, as regards the plasma cell signature determining expression for no. 1 to 5 of Table 2 may already be sufficient. Similarly for the IFN signature determining expression for no. 1 to 3 of Table 4 may already be sufficient.

As mentioned these read outs can be used to guide therapy. If for example a patient has been diagnosed with an autoimmune disease such as SLE and if treatment with a CD40 or CD40L antagonist such as an anti-CD40 or anti-CD40L antibody or binding fragment, e.g. CDP7657 thereof is considered, measuring the biomarkers of Tables 2, 3, and/or 4 as described above can help assisting whether therapy should be continued or not. For example, if the analysis reveals that the at least two plasma cell markers of Table 2 are not down-regulated and/or that the at least two B cell markers of Table 3 are not up regulated, one can discontinue treatment as early as two to four weeks because that's when any effects should become observable. However, if the analysis reveals that the at least two plasma cell markers of Table 2 are down-regulated and/or that the at least two B cell markers of Table 3 are transiently up regulated, one can continue treatment as these early reactions will indicate target engagement. One can then continue monitoring the IFN signature of Table 4 which can be considered to be indicative of early clinical response. If no down-regulation occurs one can discontinue therapy and do not have to await a complete clinical response analysis. If however down-regulation occurs, one may continue with therapy.

The same considerations apply correspondingly to the first, second, third, and fourth aspect For the sixth aspect it can be preferred that expression levels are referenced to expression levels of control samples from patients which have been diagnosed with the respective auto-immune disease such as SLE and which receive no treatment at all or receive placebo treatment.

The results as presented in the examples further reveal that patients with a diagnosed autoimmune disease which receive anti-CD40L antibody therapy and which show clinical responses seem to show an increased level of expression of the biomarkers of Table 1 before treatment commences. If a patient is diagnosed with an autoimmune disease such as SLE and CD40L antagonist therapy such as therapy with an anti-CD40L antibody or binding fragment thereof, e.g. CDP7657 is considered, one can determine the expression of these markers and administer the antibodies to such patients which show an increased expression for these markers compared to other patients or healthy volunteers, e.g., to those patients found to be in the top 25% of expressors of one or more of these genes.

Interestingly, the results also reveal that patients diagnosed with an autoimmune disease such as SLE and receiving anti-CD40L antibody therapy show increased expression of the plasma cell markers of Table 2 and of some additional plasma cell-related markers compared to healthy volunteers before treatment commences. These additional plasma-cell biomarkers are listed in Table 5 as numbers 8, and 9 and 10. Further analysis may reveal that not all patients diagnosed with an autoimmune disease such as SLE will show increased expression of these markers, Thus similarly as the biomarkers of Table 1, the biomarkers of Table 5 may be useful in identifying sub-populations of patients with a diagnosed autoimmune disease such as SLE which may have an increased likelihood for treatment success with CD40L antagonist therapy such as anti-CD40L antibodies or binding fragments thereof.

In the seventh aspect as described herein, the disclosure pertains to a method of identifying a patient suffering from an autoimmune disease likely to benefit from a therapy with a CD40 or CD40L antagonist, comprising at least the steps:
- a) determining the expression of at least one biomarker as defined in Table 1; or the expression of at least one biomarker as defined in Table 5; in a nucleic acid sample obtained from a patient which has been diagnosed with said autoimmune disease,
- b) determining the expression for said at least one biomarker in control nucleic acid samples, and
- c) deciding on whether said patient responds to treatment with a CD40 or CD40L antagonist by comparing the expression levels determined in steps a) and b).

As for the above discussed methods of monitoring and guiding therapy, the predictive power of the methods of identifying may increase the more biomarkers are analyzed. It is therefore preferred to determine the expression of at least 1, 2, 3, 4, or 5 biomarkers as defined in Table 1; and/or the expression of at least 1, 2, 3, 4, 5, 6, 7, 8, 9 or 10 biomarkers as defined in Table 5 depending on the which aspect the respective method refers to. In a further embodiment the expression of all markers of Table 1 and/or Table 5 is determined. However, for biomarkers of Table 5, determining expression of markers no 1 to 7 of Table 5 may be sufficient.

An increased expression of at least 1, 2, 3, 4, or 5 biomarkers as defined in Table 1 indicates that a patient will show a clinical response to treatment with a CD40 or CD40L antagonist with a higher likelihood than a patient which shows no increased expression of these biomarkers; similarly the disclosure considers that an increased expression of at least 1, 2, 3, 4, 6, 7, 8, 9 or 10 biomarkers as defined in Table 5 indicates that a patient will show a clinical response to treatment with a CD40 or CD40L antagonist with a higher likelihood than a patient which shows no increased expression of these biomarkers.

The same considerations apply correspondingly to the eighth aspect.

In an eighth aspect, the disclosure pertains to a method of identifying a patient suffering from an autoimmune disease likely to benefit from a therapy with a CD40 or CD40L antagonist, comprising at least the steps:
- a) determining the expression of at least one biomarker as defined in Table 1; and the expression of at least one biomarker as defined in Table 5 in a nucleic acid sample obtained from a patient which has been diagnosed with said autoimmune disease,
- b) determining the expression for said at least one biomarker in a control nucleic acid sample, and
- c) deciding on whether said patient will respond with an increased likelihood to treatment with a CD40 or CD40L antagonist by comparing the expression levels determined in steps a) and b), wherein a level of expression that is higher than that in the control sample indicates that the patient is likely to respond to the anti-CD40 or CD40L antagonist.

For the seventh and eighth aspect as described herein it is preferred that expression levels are referenced to expression levels of control samples from patients which have been diagnosed with the respective auto-immune disease such as SLE and where the respective expression levels have been previously established to not be indicative of a likely response to therapy with CD40 or CD40L antagonist. This applies in particular to the biomarkers of Table 1.

The skilled person will understand that an increased or decreased expression will typically be determined by comparing expression in samples obtained from patients versus control samples which will be normalized by standard approaches.

A change in expression may be considered to occur if the difference in expression vs the control sample is at least about 30%, at least about 40/%, at least about 50%, at least about 60%, at least about 80%, at least about 100%, at least about 200%, at least about 300% or even more pronounced. Among the afore-mentioned values, changes of at least about 200% or more are preferred. For the purposes of clarity said change in expression may be an increase or a decrease in expression vs the control sample.

The skilled person will understand that a change in expression vs the control sample may or may not be maintained over a period of time. In cases where the change in expression vs the control sample is not maintained over a period of time, the change in expression is considered to be a transient increase or transient decrease in expression vs the control sample. A transient change in expression may be considered to occur if the difference in expression vs the control sample is no longer observable after at least 2 weeks, at least 4 weeks, at least 6 weeks, 8 weeks, at least after 10 weeks, at least after 12 weeks, at least after 16 weeks, or after 20 weeks.

Expression of biomarkers in the respective samples (including control samples) can be determined as described in the examples, for example by referencing expression of the biomarkers to housekeeping genes such as GAPDH, ACTB, YWHAZ and UBC.

For the expression analysis a nucleic acid sample from a patient or healthy individuals may be used. Ribonucleic acid samples such as RNA samples are preferred. The nucleic acid or RNA sample can be a blood sample of the patient. Any other sample obtainable from the patient and containing patient blood cell ribonucleic acid or RNA can also be used. The sample can be collected from the patient by any method known in the art. For example, a blood sample can be taken from a patient by use of a sterile needle.

Usually, the ribonucleic acid or RNA is extracted or isolated or purified from the sample prior to gene transcription analysis. Any method known in the art may be used for ribonucleic acid or RNA extraction or isolation or purification. Suitable methods comprise inter alia steps such as centrifugation steps, precipitation steps, chromatography steps, dialyzing steps, heating steps, cooling steps and/or denaturation steps. For some embodiments, a certain ribonucleic acid or RNA content in the sample may be reached. Ribonucleic acid or RNA content can be measured for example via UV spectrometry as described in the literature. The RNA contained in such samples can then be converted to DNA by e.g. reverse transcription and subsequently amplified by e.g. PCR for expression analysis.

As mentioned the disclosure considers for all aspects and embodiments thereof that the sample can be outside the human or animal body.

Patients that may be considered for the methods of monitoring and guiding therapy or the methods of identifying treatment eligible may be diagnosed for autoimmune diseases by common methods known in the art. Such autoimmune disease(s) or "inflammatory disease(s) include but are not limited to systemic lupus erythematosus (SLE), rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemiphigus vulgaris, psoriasis, asthma, allergy, systemic sclerosis, multiple sclerosis, Guillain-Barré syndrome, transverse myelitis, chronic immune polyneuropathy, myasthenia gravis, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, interstitial lung disease.

In addition to the above conditions—for which an autoimmune- or cross-reactive immune-mediated inflammation is established as the primary pathological process—inflammation is also seen as one of a combination of contributory processes in many diseases. Among these are neurodegenerative disease(s) that can be treated with an antibody or antibody fragment binding specifically to CD40L according to the method or use of the invention, such diseases are hereditary or sporadic conditions which are characterized by progressive nervous system dysfunction. These disorders are often associated with atrophy of the affected central or peripheral structures of the nervous system. For example, neurodegenerative diseases include but are not limited to Alzheimer's disease, Parkinson's disease, Friedreich's ataxia, Huntington's disease, amyotrophic lateral sclerosis, myasthenia gravis, multifocal motor neuropathy, primary lateral sclerosis, spinal muscular atrophy, Kennedy's disease, and spinocerebellar ataxia. Similarly, conditions such as atherosclerosis, heart failure, osteoarthritis, nonalcoholic steatohepatitis, irritable bowel syndrome, Crohn's disease, diabetic complications (nephropathy, neuropathy, arteriopathy, retinopathy), asthma, cystic fibrosis, chronic obstructive airway disease, epilepsy, glaucoma, age-related macular degeneration, psychiatric disorders (anxiety, depression, psychosis), chronic fatigue syndrome, enthesiopathies/tendinopathies, prematurity/prenatal infection, obesity/metabolic syndrome, dermatological conditions (acne vulgaris, acne rosacea, solar keratosis), abnormal wound healing (keloid scarring), urogenital disorders (prostatism/prostatitis, overactive bladder syndrome) and cancer development are all amenable to treatment with a CD40L antagonist such as an antibody or antibody fragment binding specifically to CD40L according to the method or use of the invention.

The invention throughout all aspects and embodiments thereof considers patients diagnosed with systemic lupus erythematosus. There are different classification criteria for diagnosing SLE which are discussed in Ines, L. et al., *Arthritis Care & Research* (2015), 67 (8), 1180-1185 including the classification system by the Systemic Lupus International Collaborating Clinics (SLICC) or American College of Rheumatology (ACR). Patients may be diagnosed with SLE if they meet for example at least 4 criteria of the American College of Rheumatology classification criteria (see also Tocoian, A et al., *Lupus* (2015) Vol 24: pages 1045-56).

Exemplary aspects of the invention, in addition to those described supra are listed below:

1. Method for monitoring treatment of an autoimmune disease in a patient with a CD40 or CD40L antagonist comprising at least the steps of
   a) determining the expression of at least 2 biomarkers as defined in Table 2; the expression of at least 2 biomarkers as defined in Table 3; or the expression of at least 2 biomarkers as defined in Table 4 in a nucleic acid sample obtained from a patient which has been diagnosed with said autoimmune disease,
   b) determining the expression for said at least 2 biomarkers in a control nucleic acid sample, and
   c) deciding on whether said patient responds to treatment with a CD40 or CD40L antagonist by comparing the expression levels determined in steps a) and b).

2. Method for monitoring in accordance with embodiment 1,
   wherein the expression of at least 3, 4, 5, or 6 biomarkers as defined in Table 2; the expression of at least 3, 4, or 5 biomarker as defined in Table 3; or the expression of at least 3, or 4 biomarker as defined in Table 4 is determined in steps a) and b).

3. Method for monitoring in accordance with any of embodiments 1, or 2,
   wherein an at least transient decrease of the expression of at least 2, 3, 4, 5, 6 or 7 biomarkers as defined in Table 2 is indicative of a response to treatment by the CD40 or CD40L antagonist; an at least transient increase of the expression of at least 2, 3, 4, or 5 biomarkers as defined in Table 3 is indicative of a response to treatment by the CD40 or CD40L antagonist; or an at least transient decrease of the expression of at least 2, 3, or 4 biomarkers as defined in Table 4 is indicative of a response to treatment by the CD40 or CD40L antagonist.

4. Method for monitoring in accordance with any of embodiments 1, 2, or 3,
   wherein an at least transient decrease of the expression of at least 2, 3, 4, 5, 6 or 7 biomarkers as defined in Table 2 during 1 to 12 weeks after start of treatment is indicative of a response to treatment by the CD40 or CD40L antagonist; an at least transient increase of the expression of at least 2, 3, 4, or 5 biomarkers as defined in Table 3 during 1 to 6 weeks after start of treatment is indicative of a response to treatment by the CD40 or CD40L antagonist; or an at least transient decrease of the expression of at least 2, 3, or 4 biomarkers as defined in Table 4 during 1 to 20 weeks after start of treatment is indicative of a response to treatment by the CD40 or CD40L antagonist.

5. Method for monitoring in accordance with embodiment 4,
   wherein an at least transient decrease of the expression of at least 2, 3, 4, 5, 6 or 7 biomarkers as defined in Table 2 during 1 to 8 weeks after start of treatment is indicative of a response to treatment by the CD40 or CD40L antagonist; an at least transient increase of the expression of at least 2, 3, 4, or 5 biomarkers as defined in Table 3 during 1 to 4 weeks after start of treatment is indicative of a response to treatment by the CD40 or CD40L antagonist; or an at least transient decrease of the expression of at least 2, 3, or 4 biomarkers as defined in Table 4 during 1 to 10 weeks after start of treatment is indicative of a response to treatment by the CD40 or CD40L antagonist.

6. Method for monitoring in accordance with any of embodiments 1, 2, 3, 4, or 5,
   wherein said autoimmune disease is systemic lupus erythematosus, rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemphigus vulgaris, psoriasis, asthma, allergy, systemic sclerosis, multiple sclerosis, Guillain-Barré syndrome, transverse myelitis, chronic immune polyneuropathy, myasthenia gravis, amyotrophic lateral sclerosis, Crohn's disease, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, or interstitial lung disease.

7. Method for monitoring in accordance with any of embodiments 1, 2, 3, 4, 5, or 6,
   wherein said control sample reflects expression levels of the respective biomarkers in patients which have also been diagnosed with the respective auto-immune disease and which receive no treatment or receive placebo.

8. Method for monitoring in accordance with any of embodiments 1, 2, 3, 4, 5, 6, or 7,
   wherein said autoimmune disease is systemic lupus erythematosus (SLE).

9. Method for monitoring in accordance with any of embodiments 1, 2, 3, 4, 5, 6, 7, or 8,
   wherein said CD40 or CD40L antagonist is an anti-CD40 antibody, an anti-CD40L antibody or binding fragment thereof 10. Method for monitoring in accordance with embodiment 9,
    wherein said CD40L antagonist is a PEGylated anti-CD40L antibody or binding fragment thereof.

11. Method for monitoring in accordance with embodiment 1, 2, 3, 4, 5, 6, 7, 9, or 10,
    wherein said CD40L antagonist is the PEGylated anti-CD40L antibody fragment CDP7657.

12. Method for monitoring treatment of an autoimmune disease in a patient with a CD40 or CD40L antagonist comprising at least the steps of
    a) determining the expression of at least 2 biomarkers as defined in Table 2; and the expression of at least

27

2 biomarkers as defined in Table 3 in a nucleic acid sample obtained from a patient which has been diagnosed with said autoimmune disease, b) determining the expression for said at least 4 biomarkers in a control nucleic acid sample, and c) deciding on whether said patient responds to treatment with a CD40 or CD40L antagonist by comparing the expression levels determined in steps a) and b).

13. Method for monitoring in accordance with embodiment 12, wherein the expression of at least 3, 4, 5, 6 or 7 biomarkers as defined in Table 2; and the expression of at least 3, 4, or 5 biomarkers as defned in Table 3 is determined in steps a) and b).

14. Method for monitoring in accordance with any of embodiments 12, or 13, wherein an at least transient decrease of the expression of at least 2, 3, 4, 5, 6 or 7 biomarkers as defined in Table 2 is indicative of a response to treatment by the CD40 or CD40L antagonist; and an at least transient increase of the expression of at least 2, 3, 4, or 5 biomarkers as defined in Table 3 is indicative of a response to treatment by the CD40 or CD40L antagonist.

15. Method for monitoring in accordance with any of embodiments 12, 13, or 14, wherein an at least transient decrease of the expression of at least 2, 3, 4, 5, 6 or 7 biomarkers as defined in Table 2 during 1 to 12 weeks after start of treatment is indicative of a response to treatment by the CD40 or CD40L antagonist; and an at least transient increase of the expression of at least 2, 3, 4, or 5 biomarkers as defined in Table 3 during 1 to 6 weeks after start of treatment is indicative of a response to treatment by the CD40 or CD40L antagonist.

16. Method for monitoring in accordance with embodiment 15, wherein an at least transient decrease of the expression of at least 2, 3, 4, 5, 6 or 7 biomarkers as defined in Table 2 during 1 to 8 weeks after start of treatment is indicative of a response to treatment by the CD40 or CD40L antagonist; and an at least transient increase of the expression of at least 2, 3, 4, or 5 biomarkers as defined in Table 3 during 1 to 4 weeks after start of treatment is indicative of a response to treatment by the CD40 or CD40L antagonist.

17. Method for monitoring in accordance with any of embodiments 12, 13, 14, 15 or 16, wherein said autoimmune disease is systemic lupus erythematosus, rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemphigus vulgaris, psoriasis, asthma, allergy, systemic sclerosis, multiple sclerosis, Guillain-Barré syndrome, transverse myelitis, chronic immune polyneuropathy, myasthenia gravis, amyotrophic lateral sclerosis, Crohn's disease, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, or interstitial lung disease.

18. Method for monitoring in accordance with any of embodiments 12, 13, 14, 15, 16, or 17, wherein said control sample reflects expression levels of the respective biomarkers in patients which have also been diagnosed with the respective auto-immune disease and which receive no treatment or receive placebo.

19. Method for monitoring in accordance with any of embodiments 12, 13, 14, 15, 16, 17, or 18, wherein said autoimmune disease is systemic lupus erythematosus (SLE).

20. Method for monitoring in accordance with any of embodiments 12, 13, 14, 15, 16, 17, 18, or 19, wherein said CD40 or CD40L antagonist is an anti-CD40 antibody, an anti-CD40L antibody or binding fragment thereof.

21. Method for monitoring in accordance with embodiment 20, wherein said CD40L antagonist is a PEGylated anti-CD40L antibody or binding fragment thereof.

22. Method for monitoring in accordance with embodiment 12, 13, 14, 15, 16, 17, 18, 19, 20, or 21, wherein said CD40L antagonist is the PEGylated anti-CD40L antibody fragment CDP7657.

23. Method for monitoring treatment of an autoimmune disease in a patient with a CD40 or CD40L antagonist comprising at least the steps of a) determining the expression of at least 2 biomarkers as defined in Table 3; and the expression of at least 2 biomarkers as defined in Table 4 in a nucleic acid sample obtained from a patient which has been diagnosed with said autoimmune disease, b) determining the expression for said at least 4 biomarkers in a control nucleic acid sample, and c) deciding on whether said patient responds to treatment with a CD40 or CD40L antagonist by comparing the expression levels determined in steps a) and b).

24. Method for monitoring in accordance with embodiment 23, wherein the expression of at least 3, 4, or 5 biomarker as defined in Table 3; and the expression of at least 3, or 4 biomarker as defined in Table 4 is determined in steps a) and b).

25. Method for monitoring in accordance with any of embodiments 23, or 24, wherein an at least transient increase of the expression of at least 2, 3, 4, or 5 biomarkers as defined in Table 3 is indicative of a response to treatment by the CD40 or CD40L antagonist; and an at least transient decrease of the expression of at least 2, 3, or 4 biomarkers as defined in Table 4 is indicative of a response to treatment by the CD40 or CD40L antagonist.

26. Method for monitoring in accordance with any of embodiments 23, 24, or 25, wherein an at least transient increase of the expression of at least 2, 3, 4, or 5 biomarkers as defined in Table 3 during 1 to 6 weeks after start of treatment is indicative of a response to treatment by the CD40 or CD40L antagonist; and an at least transient decrease of the expression of at least 2, 3, or 4 biomarkers as defined in Table 4 during 1 to 20 weeks after start of treatment is indicative of a response to treatment by the CD40 or CD40L antagonist.

27. Method for monitoring in accordance with embodiment 26,
wherein an at least transient increase of the expression of at least 2, 3, 4, or 5 biomarkers as defined in Table 3 during 1 to 4 weeks after start of treatment is indicative of a response to treatment by the CD40 or CD40L antagonist; or an at least transient decrease of the expression of at least 2, 3, or 4 biomarkers as defined in Table 4 during 1 to 12 weeks after start of treatment is indicative of a response to treatment by the CD40 or CD40L antagonist.

28. Method for monitoring in accordance with any of embodiments 23, 24, 25, 26, or 27,
wherein said autoimmune disease is systemic lupus erythematosus, rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemphigus vulgaris, psoriasis, asthma, allergy, systemic sclerosis, multiple sclerosis, Guillain-Barré syndrome, transverse myelitis, chronic immune polyneuropathy, myasthenia gravis, amyotrophic lateral sclerosis, Crohn's disease, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, interstitial lung disease.

29. Method for monitoring in accordance with any of embodiments 23, 24, 25, 26, 27, or 28,
wherein said control sample reflects expression levels of the respective biomarkers in patients which have also been diagnosed with the respective auto-immune disease and which receive no treatment or receive placebo.

30. Method for monitoring in accordance with any of embodiments 23, 24, 25, 26, 27, 28, or 29,
wherein said autoimmune disease is systemic lupus erythematosus (SLE).

31. Method for monitoring in accordance with any of embodiments 23, 24, 25, 26, 27, 28, 29, or 30,
wherein said CD40 or CD40L antagonist is an anti-CD40 antibody, an anti-CD40L antibody or binding fragment thereof.

32. Method for monitoring in accordance with embodiment 32,
wherein said CD40L antagonist is a PEGylated anti-CD40L antibody or binding fragment thereof.

33. Method for monitoring in accordance with embodiment 23, 24, 25, 26, 27, or 28, 29, 30, 31, or 32,
wherein said CD40L antagonist is the PEGylated anti-CD40L antibody fragment CDP7657.

34. Method for monitoring treatment of an autoimmune disease in a patient with a CD40 or CD40L antagonist comprising at least the steps of
a) determining the expression of at least 2 biomarkers as defined in Table 2; and the expression of at least 2 biomarkers as defined in Table 4 in a nucleic acid sample obtained from a patient which has been diagnosed with said autoimmune disease,
b) determining the expression for said at least 4 biomarkers in a control nucleic acid sample, and
c) deciding on whether said patient responds to treatment with a CD40 or CD40L antagonist by comparing the expression levels determined in steps a) and b).

35. Method for monitoring in accordance with embodiment 34,
wherein the expression of at least 3, 4, 5, 6 or 7 biomarkers as defined in Table 2; and the expression of at least 3, or 4 biomarkers as defined in Table 4 is determined in steps a) and b).

36. Method for monitoring in accordance with any of embodiments 34, or 35,
wherein an at least transient decrease of the expression of at least 2, 3, 4, 5, 6 or 7 biomarkers as defined in Table 2 is indicative of a response to treatment by the CD40 or CD40L antagonist; and an at least transient decrease of the expression of at least 2, 3, or 4 biomarkers as defined in Table 4 is indicative of a response to treatment by the CD40 or CD40L antagonist.

37. Method for monitoring in accordance with any of embodiments 34, 35, or 36,
wherein an at least transient decrease of the expression of at least 2, 3, 4, 5, 6 or 7 biomarkers as defined in Table 2 during 1 to 12 weeks after start of treatment is indicative of a response to treatment by the CD40 or CD40L antagonist; and an at least transient decrease of the expression of at least 3, or 4 biomarkers as defined in Table 4 during 1 to 20 weeks after start of treatment is indicative of a response to treatment by the CD40 or CD40L Antagonist.

38. Method for monitoring in accordance with embodiment 37,
wherein an at least transient decrease of the expression of at least 2, 3, 4, 5, 6 or 7 biomarkers as defined in Table 2 during 1 to 8 weeks after start of treatment is indicative of a response to treatment by the CD40 or CD40L antagonist; and an at least transient decrease of the expression of at least 3, or 4 biomarkers as defined in Table 3 during 1 to 12 weeks after start of treatment is indicative of a response to treatment by the CD40 or CD40L antagonist.

39. Method for monitoring in accordance with any of embodiments 34, 35, 36, 37, or 38,
wherein said autoimmune disease is systemic lupus erythematosus, rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemphigus vulgaris, psoriasis, asthma, allergy, systemic sclerosis, multiple sclerosis, Guillain-Barré syndrome, transverse myelitis, chronic immune polyneuropathy, myasthenia gravis, amyotrophic lateral sclerosis, Crohn's disease, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, or interstitial lung disease.

40. Method for monitoring in accordance with any of embodiments 34, 35, 36, 37, 38, or 39,
wherein said control sample reflects expression levels of the respective biomarkers in patients which have also been diagnosed with the respective auto-immune disease and which receive no treatment or receive placebo.

41. Method for monitoring in accordance with any of embodiments 34, 35, 36, 37, 38, 39, or 40,
wherein said autoimmune disease is systemic lupus erythematosus (SLE).

42. Method for monitoring in accordance with any of embodiments 34, 35, 36, 37, 38, 39, 40, or 41,
wherein said CD40 or CD40L antagonist is an anti-CD40 antibody, an anti-CD40L antibody or binding fragment thereof.

43. Method for monitoring in accordance with embodiment 42,
wherein said CD40L antagonist is a PEGylated anti-CD40L antibody or binding fragment thereof 44. Method for monitoring in accordance with embodiment 34, 35, 36, 37, 38, 39, 40, 41, 42, or 44,
wherein said CD40L antagonist is the PEGylated anti-CD40L antibody fragment CDP7657.

45. Method for monitoring treatment of an autoimmune disease in a patient with a CD40 or CD40L antagonist comprising at least the steps of
a) determining the expression of a at least 2 biomarkers as defined in Table 2; and the expression of at least 2 biomarkers as defined in Table 3; and the expression of at least 2 biomarkers as defined in Table 4 in a nucleic acid sample obtained from a patient which has been diagnosed with said autoimmune disease,
b) determining the expression for said at least 6 biomarkers in a control nucleic acid sample, and
c) deciding on whether said patient responds to treatment with a CD40 or CD40L antagonist by comparing the expression levels determined in steps a) and b).

46. Method for monitoring in accordance with embodiment 45,
wherein the expression of at least 3, 4, 5, 6 or 7 biomarkers as defined in Table 2; and the expression of at least 3, 4, or 5 biomarkers as defined in Table 3; and the expression of at least 3, or 4 biomarker as defined in Table 4 is determined in steps a) and b).

47. Method for monitoring in accordance with any of embodiments 45, or 46,
wherein an at least transient decrease of the expression of at least 2, 3, 4, 5, 6 or 7 biomarkers as defined in Table 2 is indicative of a response to treatment by the CD40 or CD40L antagonist; and an at least transient increase of the expression of at least 2, 3, 4, or 5 biomarkers as defined in Table 3 is indicative of a response to treatment by the CD40 or CD40L antagonist; and an at least transient decrease of the expression of at least 2, 3, or 4 biomarkers as defined in Table 4 is indicative of a response to treatment by the CD40 or CD40L antagonist.

48. Method for monitoring in accordance with any of embodiments 45, 46, or 47,
wherein an at least transient decrease of the expression of at least 2, 3, 4, 5, 6 or 7, biomarkers as defined in Table 2 during 1 to 12 weeks after start of treatment is indicative of a response to treatment by the CD40 or CD40L antagonist; and an at least transient increase of the expression of at least 2, 3, 4, or 5 biomarkers as defined in Table 3 during 1 to 6 weeks after start of treatment is indicative of a response to treatment by the CD40 or CD40L antagonist; and an at least transient decrease of the expression of at least 2, 3, or 4 biomarkers as defined in Table 4 during 1 to 20 weeks after start of treatment is indicative of a response to treatment by the CD40 or CD40L antagonist.

49. Method for monitoring in accordance with embodiment 48,
wherein an at least transient decrease of the expression of at least 2, 3, 4, 5, 6 or 7 biomarkers as defined in Table 2 during 1 to 8 weeks after start of treatment is indicative of a response to treatment by the CD40 or CD40L antagonist; and an at least transient increase of the expression of at least 2, 3, 4, or 5 biomarkers as defined in Table 3 during 1 to 4 weeks after start of treatment is indicative of a response to treatment by the CD40 or CD40L antagonist; and an at least transient decrease of the expression of at least 2, 3, or 4 biomarkers as defined in Table 4 during 1 to 12 weeks after start of treatment is indicative of a response to treatment by the CD40 or CD40L antagonist.

50. Method for monitoring in accordance with any of embodiments 45, 46, 47, 48, or 49,
wherein said autoimmune disease is systemic lupus erythematosus, rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemphigus vulgaris, psoriasis, asthma, allergy, systemic sclerosis, multiple sclerosis, Guillain-Barré syndrome, transverse myelitis, chronic immune polyneuropathy, myasthenia gravis, amyotrophic lateral sclerosis, Crohn's disease, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, interstitial lung disease.

51. Method for monitoring in accordance with any of embodiments 45, 46, 47, 48, 49, or 50,
wherein said control sample reflects expression levels of the respective biomarkers in patients which have also been diagnosed with the respective auto-immune disease and which receive no treatment or receive placebo.

52. Method for monitoring in accordance with any of embodiments 45, 46, 47, 48, 49, 50, or 51,
wherein said autoimmune disease is systemic lupus erythematosus (SLE).

53. Method for monitoring in accordance with any of embodiments 45, 46, 47, 48, 49, 50, 51, or 52,
wherein said CD40 or CD40L antagonist is an anti-CD40 antibody, an anti-CD40L antibody or binding fragment thereof.

54. Method for monitoring in accordance with embodiment 53,
wherein said CD40L antagonist is a PEGylated anti-CD40L antibody or binding fragment thereof.

55. Method for monitoring in accordance with embodiment 45, 46, 47, 48, 49, 50, 51, 52, 53, or 54,
wherein CD40L antagonist said is the PEGylated anti-CD40L antibody fragment CDP7657.

56. Method for guiding treatment of an autoimmune disease in a patient with a CD40 or CD40L antagonist comprising at least the steps of
a) monitoring treatment of an autoimmune disease in a patient with a CD40 or CD40L antagonist as in any of claims 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 44, 45, 46, 47, 48, 49, 50, 51, 52, 53, 54, or 55,
b) deciding to continue treatment with said CD40 or CD40L antagonist in patients responding to treatment with said CD40 or CD40L antagonist.

57. Method for guiding treatment of an autoimmune disease in a patient with a CD40L antagonist comprising at least the steps of
a) monitoring treatment of an autoimmune disease in a patient with a CD40 or CD40L antagonist as in any of claims 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 44, 45, 46, 47, 48, 49, 50, 51, 52, 53, 54, or 55,
b) deciding to discontinue treatment with said CD40 or CD40L antagonist in patients not responding to treatment with said CD40 or CD40L antagonist.

58. Method for guiding treatment in accordance with any of embodiments 56, or 57,
wherein said autoimmune disease is systemic lupus erythematosus, rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemphigus vulgaris, psoriasis, asthma, allergy, systemic sclerosis, multiple sclerosis, Guillain-Barré syndrome, transverse myelitis, chronic immune polyneuropathy, myasthenia gravis, amyotrophic lateral sclerosis, Crohn's disease, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, interstitial lung disease.

59. Method for guiding treatment in accordance with any of embodiments 56, 57, or 58,
wherein said control sample reflects expression levels of the respective biomarkers in patients which have also been diagnosed with the respective auto-immune disease and which receive no treatment or receive placebo.

60. Method for monitoring in accordance with any of embodiments 56, 57, 58, or 59,
wherein said autoimmune disease is systemic lupus erythematosus (SLE).

61. Method for guiding treatment in accordance with any of embodiments 56, 57, 58, 59, or 60,
wherein said CD40 or CD40L antagonist is an anti-CD40 antibody, an anti-CD40L antibody or binding fragment thereof.

62. Method for guiding treatment in accordance with embodiment 61,
wherein said CD40L antagonist is a PEGylated anti-CD40L antibody or binding fragment thereof.

63. Method for guiding treatment in accordance with any of embodiments 56, 57, 58, 59, 60, 61, or 62,
wherein CD40L antagonist said is the PEGylated anti-CD40L antibody fragment CDP7657.

64. Method of identifying a patient suffering from an autoimmune disease as likely to benefit from a therapy with a CD40 or CD40L antagonist, comprising at least the steps:
a) determining the expression of a at least one biomarker as defined in Table 1; or the expression of at least one biomarker as defined in Table 5; in a nucleic acid sample obtained from a patient which has been diagnosed with said autoimmune disease,
b) determining the expression for said at least one biomarker in a control nucleic acid sample, and
c) deciding on whether said patient is likely to respond to treatment with a CD40 or CD40L antagonist by comparing the expression levels determined in steps a) and b).

65. Method of identifying in accordance with embodiment 64,
wherein the expression of at least 2, 3, 4, or 5 biomarkers as defined in Table 1; or the expression of at least 2, 3, 4, 5, 6, 7, 8, 9 or 10 biomarkers as defined in Table 5; is determined in steps a) and b).

66. Method of identifying in accordance with any of embodiments 64, or 65,
wherein an increased expression of at least 1, 2, 3, 4, or 5 biomarkers as defined in Table 1 is indicative of a response to treatment by the CD40 or CD40L antagonist; or an increased expression of at least 1, 2, 3, 4, 5, 6, 7, 8, 9 or 10 biomarkers as defined in Table 5 is indicative of a response to treatment by the CD40 or CD40L antagonist.

67. Method of identifying a patient suffering from an autoimmune disease as likely to benefit from a therapy with a CD40 or CD40L antagonist, comprising at least the steps:
a) determining the expression of a at least one biomarker as defined in Table 1; and the expression of at least one biomarker as defined in Table 5 in a nucleic acid sample obtained from a patient which has been diagnosed with said autoimmune disease,
b) determining the expression for said at least one biomarker in a control nucleic acid sample, and
c) deciding on whether said patient is likely to respond to treatment with a CD40 or CD40L antagonist by comparing the expression levels determined in steps a) and b).

68. Method of identifying in accordance with embodiment 67,
wherein the expression of at least 2, 3, 4, or 5 biomarkers as defined in Table 1; and the expression of at least 2, 3, 4, 5, 6, 7, 8, 9 or 10 biomarkers as defined in Table 5; is determined in steps a) and b).

69. Method of identifying in accordance with any of embodiments 67, or 68,
wherein an increased expression of at least 1, 2, 3, 4, or 5 biomarkers as defined in Table 1 is indicative of a response to treatment by the CD40 or CD40L antagonist; and an increased expression of at least 1, 2, 3, 4, 5, 6, 7, 8, 9 or 10 biomarkers as defined in Table 5 is indicative of a response to treatment by the CD40 or CD40L antagonist.
70. Method of identifying in accordance with any of embodiments 64, 65, 66, 67, 68, or 69,
wherein said autoimmune disease is systemic lupus erythematosus, rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemphigus vulgaris, psoriasis, asthma, allergy, systemic sclerosis, multiple sclerosis, Guillain-Barré syndrome, transverse myelitis, chronic immune polyneuropathy, myasthenia gravis, amyotrophic lateral sclerosis, Crohn's disease, Addison's disease, thyroiditis, autoimmune gastritis, pernicious anaemia, celiac disease, ulcerative colitis, sarcoidosis, hemolytic anemia, idiopathic thrombocytopenic purpura, Behçt's disease, primary biliary cirrhosis, autoimmune diabetes, Lyme neuroborreliosis, or interstitial lung disease.
71. Method of identifying in accordance with any of embodiments 64, 65, 66, 67, 68, 69, or 70,
wherein said control sample reflects expression levels of the respective biomarkers in patients which have also been diagnosed with the respective auto-immune disease and which receive no treatment or receive placebo.
72. Method for monitoring in accordance with any of embodiments 64, 65, 66, 67, 68, 69, 70, or 71,
wherein said autoimmune disease is systemic lupus erythematosus (SLE).
73. Method of identifying in accordance with any of embodiments 64, 65, 66, 67, 68, 69, 70, 71, or 72,
wherein said CD40 or CD40L antagonist is an anti-CD40 antibody, an anti-CD40L antibody or binding fragment thereof
74. Method of identifying in accordance with embodiment 73,
wherein said CD40L antagonist is a PEGylated anti-CD40L binding antibody or binding fragment thereof.
75. Method of identifying in accordance with any of embodiments 64, 65, 66, 67, 68, 69, 70, 71, 72, 73, or 74,
wherein CD40L antagonist said is the PEGylated anti-CD40L antibody fragment CDP7657.
76. A CD40 or CD40L antagonist for use in treating a patient suffering from an autoimmune disease by administering to said patient a CD40 or CD40L antagonist and
a) wherein said patient has been subject to any of the methods according to any of embodiments 64, 65, 66, 67, 68, 69, 70, 71, 72, 73, 74, or 75, or
b) wherein said patient is subject to any of the methods according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 44, 45, 46, 47, 48, 49, 50, 51, 52, 53, 54, 55, 56, 57, 58, 59, 60, 61, 62 or 63.
77. A CD40 or CD40L antagonist for use in treating a patient suffering from an autoimmune disease by administering to said patient a CD40 or CD40L antagonist and
a) wherein said patient has been subject to any of the methods according to any of embodiments 64, 65, 66, 67, 68, 69, 70, 71, 72, 73, 74, or 75, and
b) wherein said patient is subject to any of the methods according to any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 44, 45, 46, 47, 48, 49, 50, 51, 52, 53, 54, 55, 56, 57, 58, 59, 60, 61, 62 or 63.
78. A CD40 or CD40L antagonist for use of any of embodiments 76 or 77,
wherein said autoimmune disease is systemic lupus erythematosus, rheumatoid arthritis, ankylosing spondylitis, lupus nephritis, Sjögren's syndrome, polymyositis, dermatomyositis, temporal arteritis, ANCA-associated vasculitis, Churg-Strauss syndrome, antiphospholipid syndrome, membranous glomerulonephropathy, Goodpasture's disease, immunoglobulin A nephropathy, Henoch-Schönlein purpura, chronic graft rejection, atopic dermatitis, pemphigus vulgaris, psoriasis, asthma, allergy, systemic sclerosis, multiple sclerosis, Guillain-Barré syndrome, transverse myelitis, chronic immune polyneuropathy, myasthenia gravis, amyotrophic lateral sclerosis, Crohn's disease, Addison's disease, thyroiditis, autoimmune gastritis, pernicious anaemia, celiac disease, ulcerative colitis, sarcoidosis, hemolytic anemia, idiopathic thrombocytopenic purpura, Behçet's disease, primary biliary cirrhosis, autoimmune diabetes, Lyme neuroborreliosis, or interstitial lung disease.
79. A CD40 or CD40L antagonist for use of any of embodiments 76, 77, or 78, wherein said autoimmune disease is systemic lupus erythematosus (SLE).
80. A CD40 or CD40L antagonist for use of any of embodiments 76, 77, 78, or 79, wherein said CD40 or CD40L antagonist is an anti-CD40 antibody, an anti-CD40L antibody or binding fragment thereof.
81. A CD40 or CD40L antagonist for use of embodiment 80,
wherein said CD40L antagonist is a PEGylated anti-CD40L binding antibody or binding fragment thereof.
82. A CD40 or CD40L antagonist for use of any of embodiments 76, 77, 78, 79, 80, or 81,
wherein CD40L antagonist said is the PEGylated anti-CD40L antibody fragment CDP7657.
83. A CD40 or CD40L antagonist for use of any of embodiments 80, 81, or 82, wherein said use comprises:
(a) administering an initial loading dose of about 20-60 mg/kg of antibody or antibody fragment binding specifically to CD40 or CD40L to a subject in need of such treatment; and
(b) about 2 weeks after the initial loading dose administering a further dose or doses of about half of the initial loading dose with a frequency of about once every other week of antibody or antibody fragment binding specifically to CD40 or CD40L to the subject in need of such treatment.
84. A CD40 or CD40L antagonist for use of embodiment 83
wherein, the initial loading dose can be about 20 mg/kg, 25 mg/kg, 30 mg/kg, 35 mg/kg, 40 mg/kg, 45 mg/kg, 50 mg/kg, 55 mg/kg or 60 mg/kg.
85. A CD40 or CD40L antagonist for use of any of embodiments 83 or 84, wherein the further dose can be about 10 mg/kg, 12.5 mg/kg, 15 mg/kg, 17.5 mg/kg, 20 mg/kg, 22.5 mg/kg, 25 mg/kg, 27.5 mg/kg or 30 mg/kg.
86. A CD40 or CD40L antagonist for use of any of embodiments 80, 81, 82, 83, 84, or 85,
wherein the antibody or antibody fragment binding specifically to CD40 or CD40L is administered to the patient in need thereof at least for 12 weeks.
87. A group of biomarkers for use in identifying patients suffering from systemic lupus erythematosus eligible for treatment with a CD40 or CD40L antagonist comprising 1, 2, 3, 4, or 5 biomarkers of Table 1; and/or 1, 2, 3, 4, 5, 6, 7, 8, 9 or 10 biomarkers of Table 5.
88. Kit, diagnostic composition or device for conducting any of the methods of embodiments of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75, comprising at least primers and/or probes selective for determining the expression of any of the biomarkers of Tables 1, 2, 3, 4, or 5 and optionally a CD40 or CD40L antagonist.
89. Kit, diagnostic composition or device of embodiment 88,
wherein said CD40 or CD40L antagonist is an anti-CD40 antibody, an anti-CD40L antibody or binding fragment thereof.
90. Kit, diagnostic composition or device of embodiment 89,
wherein said CD40L antagonist is a PEGylated anti-CD40L binding antibody or binding fragment thereof.
91. Kit, diagnostic composition or device of any of embodiment 88, 89, or 90,
wherein CD40L antagonist said is the PEGylated anti-CD40L antibody fragment CDP7657.

The invention is now described with respect to some examples which are however not be construed as limiting.

EXPERIMENTS

Study SL0014

A clinical study in which patients with an established diagnosis of SLE were randomized in a double-blind fashion to receive six intravenous doses of CDP7657 (n=16) or matching placebo (n=8) over a period of 10 weeks. The dosing regimen under test (in those receiving active drug) comprised a single loading dose of 30 mg/kg followed by a maintenance dose of 15 mg/kg every 2 weeks thereafter, for a total of 6 doses of CDP7657. In addition to assessing the safety, tolerability and pharmacokinetic profiles of CDP7657 versus placebo, the study explored the immunogenicity (both anti-CD154/CD40L and PEG components), effects on various disease markers and effects on clinical disease parameters during and for 18 weeks after treatment. In this way the safety, tolerability and ability of the dosing regimen to deliver disease-modifying effects were established.

Data Analysis

A 96 gene panel was selected for analysis. PAXgene blood RNA tubes were collected in SL0014 and gene expression analysis was performed on each sample by quantitative RT-PCR using the Fluidigm instrument. Raw gene expression levels were normalized using a combination of housekeeping genes (GAPDH, ACTB, YWHAZ and UBC) and a set of oligonucleotide standards.

Fold change from baseline was determined for each subject and at each time point. Statistical analysis compared gene expression levels found in CDP7657 treated patients to placebo treated patients. Resulting p-values were recorded as a heat map and were colored according to those meeting pre-specified decision criteria. Individual spaghetti plots and mean fold change from baseline graphs were generated.

The decision criteria were designed to identify consistent expression changes within a domain, and ignore isolated, but statistically significant effects (see FIG. 1). A change in expression between CDP7657-treated patients and placebo-treated patients should be significant at <0.0894. The p-value was derived to achieve a 5% false positive rate at the domain level rather than adjusting p-values for multiple comparisons, as the types of changes were known from an earlier clinical study (SL0013). A change on the functional group level (e.g. plasma cells, B cells, etc.) required 2 positive, i.e. up- or down-regulated genes within a functional domain. A change on the transcriptomic domain level required a single positive functional group.

Further, patients which were considered as responders by BICLA to CDP7657 treatment were analyzed as to whether they showed increased expression for certain genes before treatment. Patients vs healthy volunteers were also analyzed as to expression pattern for genes identified during treatment.

Results

Treatment of SLE patients with CDP7657 resulted in transcriptional changes of certain genes commensurate with the inhibition of CD40L:CD40 signaling. These gene expression changes met pre-defined, internal decision-criteria to indicate a positive response on gene transcription in this SLE study.

It was found that plasma cell markers IGHA1 secretory, IGHG1 total, IGJ, IGKC and IGLC2 (see also Table 2) showed a decreased expression for patients treated with CDP7657 vs placebo starting within two weeks after treatment (see FIG. 2). FIG. 3 depicts the overall decrease in expression if the additional plasma cell markers IGHG1 secretory and TXNDC5 (see also Table 2) are additionally considered. The plasma cell signature was analyzed in more detail. Patients with SLE showed an increased expression of IGHA1 secretory, IGHG1 total, IGJ, IGKC, IGLC2, IGHG1 secretory and TXNDC5 when compared to healthy volunteers. This also applied to CD38, IGM secretory and BCMA (see Table 5 and FIG. 10).

It was further found that B cell markers CD19, IGHD membrane IGHM membrane, MS4A1, and TCL1A (See also Table 3) showed a transient increased expression for patients treated with CDP7657 vs placebo within two to four weeks after treatment (see FIG. 4). This was mirrored by a transient increase in the number of circulating B cells that mirrored the CD19 and CD20 transcript increases for patients treated with CDP7657 vs placebo within two to four weeks after treatment (see FIGS. 4, 5, 6, and 7).

It was further found that patients which according to BICLA had a clinical response showed a decreased expression of IFN related markers G1P2, MX1 IFITM3 and OAS1 (see Table 4) starting within two weeks after treatment and persisting to week 12. Among BICLA responders reduced expression was more pronounced for patients treated with CDP7657 vs placebo (see FIG. 8).

Among patients receiving CDP7657 and showing a clinical response by BICLA expression of ANKYF1, SRRM2, SPG11 and NAAA (see Table 1) was increased before treatment in comparison to patients receiving CDP7657 and not showing clinical response (see FIG. 9).

The invention claimed is:

1. A method for monitoring treatment of systemic lupus erythematosus (SLE) or lupus nephritis in a patient with a CD40L antagonist comprising administering said CD40L antagonist to said patient and, subsequently:
   a) determining the expression levels of IGHA1 and IGLC2 in a nucleic acid sample obtained from said patient,
   b) determining the expression levels for IGHA1 and IGLC2 in a control nucleic acid sample, and
   c) administering said CD40L antagonist to a patient in which the expression levels of IGHA1 and IGLC2 are transiently decreased relative to the expression levels of IGHA1 and IGLC2 in said control sample, wherein:
      said CD40L antagonist is an anti-CD40L antibody or fragment thereof comprising a light chain variable region comprising a light chain CDR1 comprising SEQ ID NO: 47, a light chain CDR2 comprising SEQ ID NO: 48, and a light chain CDR3 comprising SEQ ID NO: 49 and a heavy chain variable region comprising a heavy chain CDR1 comprising SEQ ID NO: 50, a heavy chain CDR2 comprising SEQ ID NO: 51, and a heavy chain CDR3 comprising SEQ ID NO: 52.

2. The method according to claim 1, further comprising determining the expression levels of one or more biomarker selected from IGJ, IGKC, total IGHG1, secretory IGHG1 and TXNDC5 in steps a) and b).

3. The method according to claim 1, wherein said transient decrease in expression levels occurs 1 to 12 weeks after the administration of said CD40L antagonist.

4. The method according to claim 1, wherein said control sample provides the expression levels of IGHA1 and IGLC2 in patients which have also been diagnosed with SLE and which receive no treatment or receive placebo.

5. The method according to claim 1, wherein said anti-CD40L antibody or a fragment thereof comprises a light chain comprising SEQ ID NO: 55 and a heavy chain comprising SEQ ID NO: 56.

6. A method of identifying and treating a patient suffering from systemic lupus erythematosus (SLE) or lupus nephritis with a CD40L antagonist comprising at least the steps of:
   a) determining the expression level of IGHA1 and IGLC2 in a nucleic acid sample obtained from a patient which has been diagnosed with said autoimmune disease,
   b) determining the expression level of IGHA1 and IGLC2 in a control nucleic acid sample, and
   c) treating a patient having an increased expression level of IGHA1 and IGLC2 relative to the expression level of IGHA1 and IGLC2 in the control sample with a CD40L antagonist, wherein:
      said CD40L antagonist is an anti-CD40L antibody or fragment thereof comprising a light chain variable region comprising a light chain CDR1 comprising SEQ ID NO: 47, a light chain CDR2 comprising SEQ ID NO: 48, and a light chain CDR3 comprising SEQ ID NO: 49 and a heavy chain variable region comprising a heavy chain CDR1 comprising SEQ ID NO: 50, a heavy chain CDR2 comprising SEQ ID NO: 51, and a heavy chain CDR3 comprising SEQ ID NO: 52.

7. The method according to claim 6, wherein said anti-CD40L antibody or fragment thereof is PEGylated.

8. The method according to claim 7, wherein said anti-CD40L antibody or fragment thereof is dapirolizumab pegol.

9. The method according to claim 6, wherein said an anti-CD40L antibody or fragment thereof comprises a light chain comprising SEQ ID NO: 55 and a heavy chain comprising SEQ ID NO: 56.

10. The method according to claim 6, wherein said anti-CD40L antibody or fragment thereof comprises a light chain variable region comprising SEQ ID NO: 53 and a heavy chain variable region comprising SEQ ID NO: 54.

11. The method according to claim 1, wherein said anti-CD40L antibody or fragment thereof is PEGylated.

12. The method according to claim 11, wherein said anti-CD40L antibody or fragment thereof is dapirolizumab pegol.

13. The method according to claim 1, wherein said anti-CD40L antibody or fragment thereof comprises a light chain variable region comprising SEQ ID NO: 53 and a heavy chain variable region comprising SEQ ID NO: 54.

14. The method according to claim 6, wherein the patient suffers from lupus nephritis.

15. The method according to claim 6, wherein the patient suffers from SLE.

16. The method according to claim 1, wherein the patient suffers from lupus nephritis.

17. The method according to claim 1, wherein the patient suffers from SLE.

18. The method according to claim 6, further comprising determining the expression levels of one or more biomarker selected from IGHG1 total, IGHG1 secretory, IGJ, IGKC, TXNDC5, IGM secretory, CD38, BCMA in steps a) and b).

* * * * *

UNITED STATES PATENT AND TRADEMARK OFFICE
CERTIFICATE OF CORRECTION

PATENT NO. : 11,142,794 B2
APPLICATION NO. : 15/763890
DATED : October 12, 2021
INVENTOR(S) : Geoffrey Johnston et al.

It is certified that error appears in the above-identified patent and that said Letters Patent is hereby corrected as shown below:

In the Specification

Column 9,
Line 31, "(PC) of" should read --(FC) of--.
Line 44, "(PC) in" should read --(FC) in--.

Column 12,
Line 3, "F(ab)" should read --$F(ab')_2$--.

Column 21,
Line 58, "aspect" should read --aspect.--.

Column 26,
Line 54, "thereof" should read --thereof.--.

Column 31,
Line 30, "thereof" should read --thereof.--.

Signed and Sealed this
Twenty-fourth Day of May, 2022

*Katherine Kelly Vidal*
Katherine Kelly Vidal
*Director of the United States Patent and Trademark Office*